(12) United States Patent
Masternak et al.

(10) Patent No.: US 8,137,671 B2
(45) Date of Patent: Mar. 20, 2012

(54) ANTI-IL-17F ANTIBODIES

(75) Inventors: Krzysztof Masternak, Mollens (CH); Francois Rousseau, Collonges sous Saleve (FR)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 12/774,188

(22) Filed: May 5, 2010

(65) Prior Publication Data

US 2010/0285019 A1    Nov. 11, 2010

Related U.S. Application Data

(60) Provisional application No. 61/175,512, filed on May 5, 2009.

(51) Int. Cl.
*A61K 39/00* (2006.01)

(52) U.S. Cl. .................. 424/142.1; 424/133.1; 530/351

(58) Field of Classification Search .................. None
See application file for complete search history.

(56) References Cited

U.S. PATENT DOCUMENTS

| | | | |
|---|---|---|---|
| 4,738,681 A | 4/1988 | Koeneman et al. | |
| 5,273,033 A | 12/1993 | Hoffman | |
| 5,370,870 A | 12/1994 | Wong et al. | |
| 5,444,047 A | 8/1995 | DiPasquale | |
| 5,536,637 A | 7/1996 | Jacobs et al. | |
| 5,605,690 A | 2/1997 | Jacobs et al. | |
| 5,688,681 A | 11/1997 | Kim | |
| 5,716,805 A | 2/1998 | Srinivasan et al. | |
| 5,830,877 A | 11/1998 | Carson et al. | 514/44 |
| 5,837,241 A | 11/1998 | Ferrara et al. | |
| 6,043,344 A | 3/2000 | Jacobs et al. | 530/351 |
| 6,054,559 A | 4/2000 | Young | |
| 6,074,849 A | 6/2000 | Jacobs et al. | 435/69.5 |
| 6,075,181 A | 6/2000 | Kucherlapati et al. | |
| 6,083,906 A | 7/2000 | Troutt | |
| 6,197,525 B1 | 3/2001 | Yao | |
| 6,274,711 B1 | 8/2001 | Golstein et al. | 530/389.2 |
| 6,562,333 B1 | 5/2003 | Golstein et al. | 424/85.2 |
| 6,562,578 B1 | 5/2003 | Gorman et al. | |
| 6,569,645 B2 | 5/2003 | Chen et al. | |
| 6,579,520 B2 | 6/2003 | Chen et al. | |
| 6,689,747 B2 | 2/2004 | Filvaroff et al. | |
| 6,706,870 B2 | 3/2004 | Golstein et al. | 536/23.5 |
| 6,902,735 B1 | 6/2005 | Jacobs et al. | 424/145.1 |
| 7,094,566 B2 | 8/2006 | Medlock et al. | |
| 7,115,398 B2 | 10/2006 | Chen et al. | |
| 7,217,412 B2 | 5/2007 | Chen et al. | |
| 7,256,264 B2 | 8/2007 | Goddard et al. | |
| 7,268,112 B2 | 9/2007 | Filvaroff et al. | |
| 7,790,163 B2 | 9/2010 | Jaspers | |
| 2002/0165348 A1 | 11/2002 | Presnell | |
| 2002/0177168 A1 | 11/2002 | Ikematsu | |
| 2002/0177188 A1 | 11/2002 | Chen et al. | |
| 2003/0003545 A1 | 1/2003 | Ebner et al. | |
| 2003/0009018 A1 | 1/2003 | Maeda et al. | |
| 2003/0049255 A1 | 3/2003 | Sims et al. | |
| 2003/0082734 A1 | 5/2003 | Dowling et al. | |
| 2003/0092133 A1 | 5/2003 | Ebner et al. | |
| 2003/0124123 A1 | 7/2003 | Gils-Komar et al. | |
| 2003/0157508 A1 | 8/2003 | Ebner et al. | |
| 2003/0186306 A1 | 10/2003 | Chen et al. | |
| 2003/0186387 A1 | 10/2003 | Ebner et al. | |
| 2003/0199041 A1 | 10/2003 | Presnell | |
| 2004/0043397 A1 | 3/2004 | Chen et al. | |
| 2004/0156849 A1 | 8/2004 | Gurney | |
| 2004/0223969 A1 | 11/2004 | Oft et al. | |
| 2004/0258686 A1 | 12/2004 | Chirica et al. | |
| 2005/0004354 A1 | 1/2005 | Salfeld et al. | |
| 2005/0100917 A1 | 5/2005 | Chirica et al. | |
| 2005/0100918 A1 | 5/2005 | Chirica et al. | |
| 2005/0147609 A1 | 7/2005 | Filvaroff | 424/145.1 |
| 2005/0158750 A1 | 7/2005 | Bazan | |
| 2005/0208052 A1 | 9/2005 | Katsikis et al. | |
| 2005/0250770 A1 | 11/2005 | Ono et al. | |
| 2005/0250774 A1 | 11/2005 | Ono et al. | |
| 2005/0287593 A1 | 12/2005 | Kastelein et al. | |
| 2006/0067936 A1 | 3/2006 | Benson et al. | |
| 2006/0088916 A1 | 4/2006 | Chen et al. | |
| 2006/0134755 A1 | 6/2006 | Chen et al. | |
| 2006/0205038 A1 | 9/2006 | Chen et al. | |
| 2006/0270003 A1 | 11/2006 | Arnott et al. | 435/69.52 |
| 2007/0020735 A1 | 1/2007 | Chen et al. | |
| 2007/0160576 A1 | 7/2007 | Arnott et al. | |
| 2007/0212362 A1 | 9/2007 | Filvaroff | 424/158.1 |
| 2008/0160021 A1 | 7/2008 | Chen et al. | |
| 2008/0161540 A1 | 7/2008 | Arnott et al. | |

(Continued)

FOREIGN PATENT DOCUMENTS

CA         2343569         3/2000

(Continued)

OTHER PUBLICATIONS

Ishigame et al., "Differential roles of interleukin-17A and -17F in host defense against mucoepithelial bacterial infection and allergic responses," Immunity, vol. 30:108-119 (2009).

Kohno et al., "Interleukin-17 gene expression in patients with rheumatoid arthritis," Mod. Rheumatol., vol. 18: 15-22 (2008).

Liang et al., "An IL-17F/A Heterodimer Protein Is Produced by Mouse Th17 Cells and Induces Airway Neutrophil Recruitment," J. Immunol., vol. 179: 7791-7799 (2007).

McAllister et al., "Role of IL-17A, IL-17F, and the IL-17 Receptor in Regulating Growth-Related Oncogene-α and Granulocyte Colony-Stimulating Factor in Bronchial Epithelium: Implications for Airway Inflammation in Cystic Fibrosis," J. Immunol., vol. 175: 404-412 (2005).

Ruddy et al., "Functional Cooperation between Interleukin-17 and Tumor Necrosis Factor-α Is Mediated by CCAAT/Enhancer-binding Protein Family Members," J. Biol. Chem., vol. 279(4): 2559-2567 (2004).

(Continued)

Primary Examiner — Dong Jiang

(74) Attorney, Agent, or Firm — Arnold & Porter LLP; Bonny Yeung; Ginger R. Dreger

(57) ABSTRACT

This invention provides fully human monoclonal antibodies that recognize IL-17F and/or the heterodimeric IL-17A/IL-17F complex, but do not recognize IL-17A. The invention further provides methods of using such monoclonal antibodies as a therapeutic, diagnostic, and prophylactic.

6 Claims, 3 Drawing Sheets

U.S. PATENT DOCUMENTS

| | | | |
|---|---|---|---|
| 2008/0199460 A1 | 8/2008 | Cua et al. | 424/133.1 |
| 2008/0317749 A1 | 12/2008 | Kastelein et al. | 424/133.1 |
| 2009/0028860 A1 | 1/2009 | Kastelein et al. | 434/136.1 |
| 2009/0317400 A1 | 12/2009 | Masternak | |

FOREIGN PATENT DOCUMENTS

| | | |
|---|---|---|
| CA | 2378519 | 1/2001 |
| CA | 2401273 | 9/2001 |
| CA | 2403370 | 9/2001 |
| EP | 1 386 931 | 2/2004 |
| EP | 1 443 055 | 8/2004 |
| EP | 1983000 A2 | 10/2008 |
| JP | 2000186046 | 7/2000 |
| WO | WO 91/19510 | 12/1991 |
| WO | WO 92/13565 | 8/1992 |
| WO | WO 94/01548 | 1/1994 |
| WO | WO 95/18826 | 7/1995 |
| WO | WO 96/29408 | 9/1996 |
| WO | WO 97/04097 | 2/1997 |
| WO | WO 97/20062 | 6/1997 |
| WO | WO 97/25426 | 7/1997 |
| WO | WO 98/23284 | 6/1998 |
| WO | WO 98/49310 | 11/1998 |
| WO | WO 99/03982 | 1/1999 |
| WO | WO 99/05280 | 2/1999 |
| WO | WO 99/14240 | 3/1999 |
| WO | WO 99/31969 | 7/1999 |
| WO | WO 99/32632 | 7/1999 |
| WO | WO 99/35267 | 7/1999 |
| WO | WO 99/46281 | 9/1999 |
| WO | WO 99/51259 | 10/1999 |
| WO | WO 99/60127 | 11/1999 |
| WO | WO 99/61617 | 12/1999 |
| WO | WO 00/15798 | 3/2000 |
| WO | WO 00/20593 | 4/2000 |
| WO | WO 00/42187 | 7/2000 |
| WO | WO 00/42188 | 7/2000 |
| WO | WO 00/53752 | 9/2000 |
| WO | WO 00/55204 | 9/2000 |
| WO | WO 00/56772 | 9/2000 |
| WO | WO 00/70050 | 11/2000 |
| WO | WO 00/73452 | 12/2000 |
| WO | WO 01/04304 | 1/2001 |
| WO | WO 01/12659 | 2/2001 |
| WO | WO 01/16318 | 3/2001 |
| WO | WO 01/18022 | 3/2001 |
| WO | WO 01/40465 | 6/2001 |
| WO | WO 01/46420 | 6/2001 |
| WO | WO 01/48192 | 7/2001 |
| WO | WO 01/49728 | 7/2001 |
| WO | WO 01/54477 | 8/2001 |
| WO | WO 01/57202 | 8/2001 |
| WO | WO 01/68705 | 9/2001 |
| WO | WO 01/68848 | 9/2001 |
| WO | WO 01/68859 | 9/2001 |
| WO | WO 01/79288 | 10/2001 |
| WO | WO 01/85790 | 11/2001 |
| WO | WO 01/90358 | 11/2001 |
| WO | WO 01/93983 | 12/2001 |
| WO | WO 02/00690 | 1/2002 |
| WO | WO 02/08259 | 1/2002 |
| WO | WO 02/08284 | 1/2002 |
| WO | WO 02/08285 | 1/2002 |
| WO | WO 02/08288 | 1/2002 |
| WO | WO 02/12500 | 2/2002 |
| WO | WO 2004/042009 | 5/2004 |
| WO | WO 2005/000897 | 1/2005 |
| WO | WO 2005/010044 | 2/2005 |
| WO | WO 2005/051422 | 6/2005 |
| WO | WO 2005/108616 | 11/2005 |
| WO | WO 2006/013107 | 2/2006 |
| WO | WO 2006/054059 | 5/2006 |
| WO | WO 2006/088833 | 8/2006 |
| WO | WO 2006/132788 | 12/2006 |
| WO | WO 2007/027761 | 3/2007 |
| WO | WO 2007/056470 A2 | 5/2007 |
| WO | WO 2007/070750 | 6/2007 |
| WO | WO 2007/106769 | 9/2007 |
| WO | WO 2007/117749 | 10/2007 |
| WO | WO 2007/147019 | 12/2007 |
| WO | WO 2008/001063 | 1/2008 |
| WO | WO 2008/047134 | 4/2008 |
| WO | WO 2008/067223 | 6/2008 |
| WO | WO 2008/133684 | 11/2008 |
| WO | WO 2008/134659 A2 | 11/2008 |
| WO | WO 2009/015063 | 1/2009 |
| WO | WO 2009/026412 | 2/2009 |
| WO | WO 2009/130459 | 10/2009 |
| WO | WO 2009/136286 A2 | 11/2009 |

OTHER PUBLICATIONS

Seiderer et al., "Role of the Novel Th17 Cytokine IL-17F in Inflammatory Bowel Disease (IBD): Upregulated Colonic IL-17F Expression in Active Crohn's Disease and Analysis of the IL17F p.His161Arg Polymorphism in IBD," Inflamm. Bowel Dis., vol. 14(4): 437-445 (2008).

Wei et al, "IL-21 Is Produced by Th17 Cells and Drives IL-17 Production in a STAT3-dependent Manner," J. Biol. Chem., vol. 282(48): 34605-34610 (2007).

Yusuf-Makagiansar, "Inhibition of LFA-1/ICAM-1 and VLA-4/VCAM-1 as a Therapeutic Approach to Inflammation and Autoimmune Diseases," Medicinal Research & Reviews, vol. 22(2): 146-167 (2002).

Database Uniprot, "Interleukin-17 receptor D precursor (IL-17 receptor D) (IL-17RD) (IL17Rhom) (Interleukin-17 receptor-like protein) (Sef homolog) (hSef)", Accession No. Q8NFM7, Sep. 13, 2005.

Database Uniprot, "Interleukin-17 receptor E precursor (IL-17 receptor E) (IL-17RE)", Accession No. Q8NFR9, Oct. 1, 2002.

Database Uniprot, "Interleukin-17D precursor (IL-17D) (Interleukin-27) (IL-27)", Accession No. Q8TAD2, Jun. 1, 2002.

Database Uniprot, "Uncharacterized protein IL 17RE (Fragment)", Accession No. A6NL85, Jul. 24, 2007.

Fossiez at al., "Interleukin-f7" Int. Rev. Immunol.16(5-6):541-551, (1998).

Gordon et al., "Molecular immunobiology of macrophages: recent progress" Current Opinion in Immunology 7:24-33, (1995).

Hillier et al., "The WashU Merck EST Project" EMBL Database entry HSA33733, Accession No. AA033733 (1986), XP002073848.

Hillier et al., "WashU-NCI Human EST Project" EMBL Database entry AA780147, Accession No. AA780147 (1998), XP002123461.

Kanakura, Y. et al., "Identification of functionally distinct domains of human granulocyte-macrophage colony-stimulating factor using monoclonal antibodies," Blood 77: 1033-1043 (1991).

Kingsley et al.,"Joint destruction in rheumatoid arthritis: biological bases" Clin. Exp. Rheumatol. 15:53-S14, (1997).

Klein et al., "Selection for Genes Encoding Secreted Proteins and Receptors" Proc, Natl. Acad. Sci, USA 93(141:7108-7113, (1996).

Lennon at al., "The I.M.A.G.E. Consortium: An Integrated Molecular Analysis of Genomes and Their Expression" Genomics (Article #0177) 33:151-152, (1996).

Li, et al,, "Identification and functional characterization of a novel interleukin 17 receptor: A possible mitogenic activation through ras/mitogen-activated protein kinase signaling pathway", Cellular Signaling, vol. 18, No. 8, pp. 1287-1298, Aug. 2006.

Lotz et al., "IL-17 Promotes Cartilage Degradation" Cytokines (ACR Abstract Session 10, Oct. 19, 1996, abstract #559) pp. S120 (1996).

Luckow et al., "Trends in the Development of Baculovirus Expression Vectors" Bio/Technoloav 6:47-55 (1988).

March et al., "Cloning, sequence and expression of two distinct human interleukin-1 complementary DNAs" Nature 315:641-647, (Jun. 20, 1985).

Marra et al., The WashU-HHMIMouse EST project, Locus AA763404, Jan. 27, 1998, Accessed Dec. 13, 2000.

Martel-Pelletier et al., "Major Signaling Pathways Involved in the IL-17 Induced Nitric Oxide (NO Production in Human Osteoarthritic Chondrocytes" Orthopaedic Research Society (45th) Annual Meeting, Feb. 1-4, 1999, pt 2) 24:595, (1999).

Nicola, N.A., et al., "Neutralizing and non-neutralizing monoclonal antibodies to the granulocyte-macrophage colony-stimulating factor receptor alpha-chain," Blood 82: 1724-1731 (1993).

Olive, D. et al., "Anti-interleukin 2 receptor monoclonal antibodies: Respective role of epitope mapping and monoclonal antibody-receptor interactions in their antagonist effects on interleukin 2-dependent T cell growth," Eur. J. Immunol. 16: 611-616 (1986).

Parnet et al., J. Biol. Chem. 271: 3967-3970, 1996.

Popkov, M. et al, "Human/mouse cross-reactive anti-VEGF receptor 2 recombinant antibodies selected from an immune b9 allotype rabbit antibody library," J. Immunol. Meth. 288: 149-164 (2004).

Redlich, P.N. et al., "Antibodies that neutralize human 13 interferon biologic activity recognize a linear epitope: Analysis by synthetic peptide mapping," Proc. Natl. Acad. Sci. USA 88: 4040-4044 (1991).

Rogachefsky et al., "Treatment of canine osteoarthritis with insulin-like growth factor-1 (IGF-1) and sodium pentosan polysulfate" Osteoarthritis and Cartilage 1:105-114, (1993).

Schwarzenberger et al., "IL-17 Stimulates Granulopoiesis in Mice: Use of an Alternate, Novel Gene Therapy-Derived Method for In Vivo Evaluation of Cytokines" Journal of Immunology 161:6383-6389 (1998).

Seow, H.F., "Pathogen interactions with cytokines and host defence: an overview" Vet Immunol. Immunopathol. 63(1-2):139-148, (1998).

Shi, "A Novel Cytokine Receptor-Ligand Pair: Identification, Molecular Characterization and In Vivo Immunomodulatory Activity." J. Biological Chemistry, American Society of Biological Chemists, Baltimore 275(25):19167-19176, (Jun. 23, 2000).

Starnes, et al., "Cutting edge: IL-D, a novel member of the IL-17 family, stimulates cytokine production and inhibits hemopoiesis" Journal of Immunology, vol. 169, No. 2, pp. 642-646, (2002).

Subramaniam et al., "Evidence for the Involvement of JAK/STAT Pathway in the Signaling Mechanism of Interleukin-17" Biochem. & Biophys. Res. Comm. 262:14-19, (1999).

Subramaniam et al., "InterleUkin-17 Induces Rapid Tyrosine Phosphorylation and Activation of Raf-1 Kinase in Human Monocytic Progenitor Cell Line 0937" Biochem. & Biophys. Res. Comm. 259:172-177, (1999).

Tartour et al., "Interleukin 17, a T-cell-derived Cytokine, Promotes Tumorigenicity of Human Cervical Tumors in Nude Mice" Cancer Research 59:3698-704, (1999).

Tian, et al., "EVI127 encodes a novel membrane protein with homology to the IL17 receptor", Oncogene, vol. 19, No. 17, pp. 2098-2109, Apr. 20, 2000.

Vukicevic et al., "Induction of nephrongenic mesenchyme by osteogenic protein 1 (bone morphogenetic Protein 7)", Proc. Natl. Acad. Sci. 93:9021-9026, (1996).

Yang, et al., "A novel interleukin-17 receptor-like protein identified in human umbilical vein endothelial cells antagonizes basic fibroblast growth factor-induced signaling", Journal of Biological Chemistry, vol. 278, No. 35, pp. 33232-33238, (2003).

Yone, K. et al., "Epitopic regions for antibodies against tumor necrosis factor a: Analysis by synthethic peptide mapping," J. Biol. Chem. 270: 19509-19515 (1995).

Kennedy et al., "Mouse IL-17: A Cytokine Preferentially Expressed by apTCR+CD4-CD8- T Cells" Journal of Interferon and Cytokine Research 16(8):611-617, (1996).

Kuestner, R.E., et al., The Journal of Immunology—179:5462-5473 (2007).

Kwon et al., "Manipulation of T Cell Costimulatory and Inhibitory Signals for Immunotherapy of Prostate Cancer." Proc. Natl. Acad. Sci. USA 94(15):8099-8103, (1997).

Laan, "Neutrophil Recruitment by Human IL-17 via C-X-C-Chemokine release in the Airways" The Journal of Immunology 162:2347-2352, (1999).

Lee, et al., The journal of Biological Chemistry, vol. 276, No. 2, pp. 1660-1664, (2001).

Li, H., et al., PNAS—97(2):773-778 (2000).

Linden, "Airway neutrophils and interleukin-17" Eur Respir J 15:973-977, (2000).

Linsley and Ledbetter., "The Role of the CD28 Receptor During T Cell Responses to Antigen." Annu. Rev. Immunol. 11:191-212, (1993).

Lock, C., et al., Nature Medicine-8(5):500-508 (2002).

Lubberts, E., et al., The Journal of Immunology-167: 1004-1013 (2001).

Lynch et al., "Flt3 Ligand Induces Tumor Regression and Antitumor Immune Responses In Vivo." Nature Medicine. 3(6):625-631, (1997).

Melero et al., "Monoclonal Antibodies Against the 4-1BB T-cell Activation Molecule Eradicate Established Tumors." Nature Medicine. 3(6):682-685, (1997).

Moseley et al., "Interleukin-17 family and IL-17 receptors" Cytokine And Growth Factor Reviews 4(2):155-174, (2003).

Nakae, S., et al., Immunity—17:375-387 (2002).

Nakae, S., et al., The Journal of Immunology—171:6173-6177 (2003).

Nielsen et al., "Identification of Prokaryotic and Eukaryotic Signal Peptides and Prediction of Their Cleavage Sites" Protein Engineering. 16(1):1-6, (1997).

Okuda, Y., et al., Journal of Neuroimmunology—101:188-196 (1999).

Ozenci, V., et al., Multiple Sclerosis—8:396-404 (2002).

Peterson et al., "Immunnization With Mclan-A Peptide-Pulsed Peripheral Blood Mononuclear Cells Plus Recombinant Human Interleukin-12 Induces Clinical Activity and T-Cell Responses in Advanced Melanoma" Journal of Clinical Oncology 21(12):2342-2348, (2003).

Rickel, et al., The Journal of Immunology, 181: 4299-4310, (2008).

Schwartz, R., "Costimulation of T Lymphocytes: The Role of CD28, CTLA-4, and B7/BB1 in Interleukin-2 Production and Immunotherapy." Cell. 71(7):1065-1068, (1992).

Shalom-Barak et al., "Interleukin-17-induced Gene Expression in Articular Chondrocytes is Associated with Activation of Mitogen-activated Protein Kinases and NF-KB" Journal of Biological Chemistry273(42):27467-27473, (1998).

Singh, V.K., et al., Immunologic Research—20:147-161 (1999).

Starnes et al., "Cutting Edge: IL-17F, a Novel Cytokine Selectively Expressed in Activated T Cells ant Monocytes, Regulates Angiogenesis and Endothelial Cell Cytokine Production" Journal of Immunology167:4137-4140, (2001).

Tarner, I.H., et al., Current Opinion in Immunology—13:676-682 (2001).

Teunissen et al., "Interleukin-17 and Interferon-y Synergize in the Enhancement of Proinflammatory Cytokine Production by Human Keratinocytes" J. Invest. Dermatol. 111:645-649, (1998).

Thurner et al.,."Vaccination with Mage-3A1 Peptide-pulsed Mature, Monocyte-derived Dendritic Cells Expands Specific Cytotoxic T Cells and Induces Regression of Some Metastases in Advanced Stage IV Melanoma" Journal of Experimental Medicine 190:1669-1678 (1999).

Tompkins, S.M., et al., Nature Medicine—8(5):451-453 (2002).

Toy, et al., The journal of Immunology, 177: 36-39, (2006).

Valjakka, J. et al., J.Biol. Chem. 277:44021-44027 (2002).

Van Bezooijen et al., "Interleukin-17: A New Bone Acting Cytokine In Vitro" Journal of Bone and Mineral Research 14(9):1513-1521, (1999).

Van Kooten, C., et al., J. Am Soc Nephrol—9:1526-1534 (1998).

von Heijne, G., "A new method for predicting signal sequence cleavage sites" Nucl. Acids. Res. 14(11):4683-4690, (1986).

Walunas et al., "CTLA-4 Can Function as a Negative Regulator of T Cell Activation." Immunity. 1(5):405-413, (1994).

Wiendl, H., et al., Biodrugs—16(3):183-200 (2002).

Witowski, J., et al., The Journal of Immunology—165:5814-5821 (2000).

Wright, J. F., et al., Journal of Biological Chemistry, 282(18): 13447-13455 (2007).

Xiong et al. Regulation of IL-8 expression by nitric oxide in human pancreatic adenocarcinoma. J. Interferon Cytokine Res., Jul. 2001, 21(7):529-37 (abstract only).

Yamaguchi, Y., et al., The Journal of Immunology—179:7128-7136 (2007).

Yao et al., "Herpesvirus Saimiri Encodes a New Cytokine, IL-17, which Binds to a Novel Cytokine Receptor" Immunity 3:811-821, (1995).

Yao et al., "Human IL-17: A Novel Cytokine Derived from T Cells" Journal of Immunology 155(12):5483-5486, (1995).

Yao et al., "Molecular Characterization of the Human Interleukin (IL)-17 Receptor" Cytokine9(11):794-800, (1997).

Yazaki, P.J., et al., Protein Engineering, Design & Selection—17(5):481-489 (2004).
Zhang, G-X., et al., The Journal of Immunology—170:2153-2160 (2003).
U.S. Appl. No. 60/085,579, filed May 15, 1998, Wood.
"qk39g09.x1 NCI_CGAP_Co8 Homo sapiens cDNA clone Image:1871392 3', mRNA sequence." XP002154807, (1998).
Aarvak et al., IL-17 s Produced by Some Proinflammatory Th1/Th0 Cells but not by Th2 Cells Journal of Immunology 162:1246-1251, (1999).
Abbaszade et al.,"Cloning and characterization of ADAMTS11, an Aggrecanase from the Adamts Family" Journal of Biological Chemistry 274(33):23443-23450, (1999).
Abe et al., "Differentiation-Inducing Factor Purified From Conditioned Medium of Mitogen-Treated Spleen Cell Cultures Stimulated Bone Resorption" Proc. Natl. Acad. Sci. USA 83:5958-5962, (1986).
Albanesi et al., "Interleukin-17 is Produced by Both Th1 and Th2 Lymphocytes, and Modulates Interferon-γ- and Interleukin-4-Induced Activation of Human Keratinocytes" Journal of Investigative Dermatology 115(1):81-87, (2000).
Alderson et al., "Molecular and Biological Characterization of Human 4-1BB and Its Ligand." European Journal of Immunology. 24(9):2219-2227 (1994).
Becher, B., et al., The Journal of Clinical Investigation—112(8):1186-1191 (2003).
Boder, E.T. et al., Proc. Natl. Acad. Sci. USA 97:10701-10705 (2000).
Burchill, M.A., et al., Infection and Immunity—71(6):3437-3442 (2003).
Bush, K.A., et al., Arthritis & Rheumatism—46(2):802-805 (2002).
Cai et al., "Regulation of granulocyte colony-stimulating factor gene expression by interleukin-17" Immunology Letters 62:51-58, (1998).
Chabaud et al., "Enhancing Effect of IL-17 on IL-1-Induced IL-6 and Leukemia Inhibitory Factor Production by Rheumatoid Arthritis Synoviocytes and Its Regulation by Th2 Cytokines" Journal of Immunology 161:409-414, (1998).
Chaly, et al., Cytokine 12(6): 636-643 (Jun. 2000) (abstract only).
Chambers and Allison., "Co-Stimulation in T Cell Responses." Current Opinion in Immunology. 9(3):396-404, (1997).
Chen, G. et al., Protein Engineering 12:349-356 (1999).
Cua, D.J., et al., Letters to Nature—421:744-748 (2003).
De Smet et al., "The Activation of Human Gene MAGE-1 in Tumor Cells is Correlated with Genome-Wide Demethylation." Proc. Natl. Acad. Sci. USA 93(14):7149-7153, (1996).
Dubowchik, G.M., et al., Pharmacology & Therapeutics—83:67-123 (1999).
Ely, et al., Nature Immunology, vol. 10, No. 12, pp. 1245-1252, (2009).
Finn and Lotze., "Introduction: Third Keystone Symposium on Cellular Immunology and the Immunotherapy of Cancer." Journal of Immunotherapy. 21(2):114-118 (1998).
Fleit, et al., Journal of Leukocyte Biology, 49: 556-565, (1991).
Fossiez et al., "T Cell Interleukin-17 Induces Stromal Cells to Produce Proinflammatory and Hematopoietic Cytokines" Journal of Experimental Medicine 183(6):2593-2603, (1996).
Gerhardt et al., J. Mol. Biol. 394: 905-921 (2009).
Gerstner et al., "Sequence Plasticity in the Antigen-binding Site of a Therapeutic Anti-HER2 Antibody" J. Mol. Biol.321:851-862, (2002).
Goodin, D.S., et al., Neurology—58:169-178 (2001).
Gubler et al., of Two Distinct Genes Is Required to Generate Secreted Bioactive Cytotoxic Lymphocyte Maturation Factor Proc. Natl. Acad. Sci. USA 88:4143-4147, (1991).
Haak, S., et al., The Journal of Clinical Investigation—119(1):61-69 (2009).
Hellstrom and Hellstrom., "T Cell Immunity to Tumor Antigens." Critical Reviews in Immunology. 18(1-2):1-6, (1998).
Homey et al., "Up-Regulation of Macrophage Inflammatory PRotein-3a/CCL20 and CC Chemokine Receptor 6.in Psoriasis" Journal of Immunology 164(12):6621-6632, (2000).
Hymowitz et al., "IL-17s adopt a cystinc knot fold: structure and activity of a novel cytokine, IL-17F, and implications for receptor binding" EMBO Journal 20:5332-5341, (2001).
Jenkins, M., "The Ups and Downs of T Cell Costimulation." Immunity. 1(6):443-446, (1994).
Jonker, M., et al., Human Immunology—32:31-40 (1991).
Joosten, L.A.B., et al., The Journal of Immunology—159:4094-4102 (1997).
Jovanovic et al., "IL-17 Stimulates the Production and Expression of Proinflammatory Cytokines, IL-13 and TNF-a, by Human Macrophages" J. Immunol 160:3513-3521, (1998).
June et al., "The B7 and CD28 Receptor Families." Immunology Today. 15(7):321-331, (1994).
U.S. Appl. No. 60/085,579, filed May 15, 1998, Wood.
U.S. Appl. No. 60/087,340, filed May 29, 1998, Ebner et al.
U.S. Appl. No. 60/099,805, filed Sep. 10, 1998, Ebner et al.
U.S. Appl. No. 60/131,965, filed Apr. 30, 1999, Ebner et al.
Aarvak, T., et al., Scandinavian Journal of Immunology—50: No. 1-9 (1999) (XP-002352889).
Adorini, et al., CMLS, 55: 1610-1625, (1999).
Aggarwal and Gurney, "IL-17: prototype member of an emerging cytokine family" Journal of Leukocyte Biology 71:1-8 (2002).
Arican, et al., Mediators of Inflammation, 5: 273-279, (2005).
Becher, B., et al., The Journal of Clinical Investigation—110(4):493-497 (2002).
Belladonna, et al., The Journal of Immunology—168:5448-5454 (2002).
Benson, J., et al., The FASEB Journal—16(5): p. A1045, Abstract #759.12 (Mar. 22, 2002).
Bowman, E.P., et al., Current Opinion in Infectious Diseases—19:245-252 (2006).
Brok, H.P. M, et al., The Journal of Immunolog—169:6554-6563 (2002) (XP-002971968).
Chabaud et al., Human Interleukin-17: A T Cell-Derived Proinflammatory Cytokine Produced by the Rheumatoid Synovium Arthritis & Rheumatism 42(5):963-970, (1999).
Constantinescu, C.S., et al., The Journal of Immunology—161:5097-5104 (1998).
Declaration of Dr. Kikly (2010).
Frisullo, et al., Cytokine, 44: 22-25, (2008).
Frucht, D.M., Science STKE—114:1-3 (2002).
Fujino, et al., Gut, 52: 65-70, (2003).
Gately, et al., Annu. Rev. Immunol., 16: 495-521, (1998).
Ghilardi, et al., "Comprised humoral delayed-type hypersensitivity responses in IL-23-deficient mice", The Journal of Immunology, 172: 2827-2833, (2004).
Hamzaoui, et al., Scand. J. Rheumatol, 31: 205-210, (2002).
Ishii, et al., "Development of IL-17-mediated delayed-type hypersensitivity is not affected by down-regulation of IL-25 expression", Allergology International, vol. 59, No. 4, pp. 1-10, (2010).
Kagami, et al., Journal of Investigative Dermatology, 130: 1373-1383, (2010).
Katsifis, et al., The American journal of Immunology, vol. 175, No. 3, 1167-1177, (2009).
Kikly, et al., Current opinion in Immunology, 18: 670-675, (2006).
Kobayashi, et al., "Immunopathogenesis of delayed-type hypersensitivity", Microscopy research and technique, vol. 53, pp. 241-245, (2001).
Kullberg, et al., Infection and Immunity, pp. 4232-4241, (2001).
Kurasawa et al., "Increased interleukin-17 production in patients with systemic sclerosis" Arthritis and Rheumatism 43(11):2455-2463, (2000).
Lankford, et al., Journal of Leukocyte Biology, vol. 73, 49-56, (2003).
Lo, et al., The Journal of Immunology, 171: 600-607, (2003).
Maeyama, T., et al., American Journal of Physiology, Lung Cellular and Molecular Physiology—280(6):L1128-L1137 (2001) (XP-002352888).
Marshall, et al., "Violent reaction to monoclonal antibody therapy remains a mystery", Science, vol. 311, pp. 1688-1689, (2006).
Molet, et al., J. Allergy clin. Immunol , 108: 430-438, (2001).
Neurath, et al., The Journal of Experimental Medicine, vol. 182, pp. 1281-1290, (1995).
Oppmann, B., et al., Immunity—13(5):715-725 (2000).
Parham, C., et al., Journal of Imunology—168:5699-5708 (2002).

Shen, et al., Arthritis & Rheumatism, vol. 60, No. 6, pp. 1647-1656, (2009).
Shevach, et al., Springer Semin. Immunopathol., 21: 249-262, (1999).
Sugihara, et al., Clinical & Experimental Immunology, 160: 386-393, (2010).
Tripp, C.S., et al., Journal of Immunology—152:1883-1887 (1994) (XP-002924062).
Wiekowski, et al., Journal of Immunology—166:7563-7570 (2001).
Windhagen, et al., J. Exp. Med., vol. 182, pp. 1985-1996, (1995).
Wong, et al., Clinical Exp. Immunology, 125: 177-183, (2001).
Wong, et al., Lupus—9:589-593 (2000).
Wysocka, et al., Eur. J. Imm., 25: 672-676, (1995).
Zhang, Z., et al., Interntional Imunopharmacology—7:409-416 (2007).
Zhao, et al., Mol. Biol. Rep., 37: 81-85, (2010).
Allan et al., "Osteoblasts Display Receptors for and Responses to Leukemia-Inhibitory Factor" J. Cellular Physiology 145:110-119, (1990).
Amin and Abramson., "The Role of Nitric Oxide in Articular Cartilage Breakdown in Osteoarthritis." Curr. Opin. Rheum. 10(3):263-268, (1998).
Arend and Dayer, "Inhibition of the production and effects of interleukin-1 and tumor necrosis factor a in rheumatoid arthritis" Arthritis and Rheumatism 38(2):151-160, (1995).
Arend W. P. et al., "Interleukin-1 Receptor Antagonist: Role in Biology" Ann. Rev. Immunol. 16:27-55, (1998).
Arner et al., "Generation and Characterization of Aggrecanase" Journal of Biological Chemistry 274(10):6594-6601, (1999).
Attur et al., "Interleukin-17 Up-Regulation of Nitric Oxide Production in Human Osteoarthritis Cartilage" Arthritis and Rheumatism 40(6):1050-1053,(1997).
Baragi et al., "Transplantation of Adenovirally Transduced Allogeneic In Vivo." Chondrocytes into Articular Cartilage Defects Osteoarthritis and Cartilage. 5(4):275-282, (1997).
Baragi et al., "Transplantation of Transduced Chondrocytes Protects Articular Cartilage from Interleukin 1-Induced Extracellular Matrix Degradation" Protects J. Clin. 96(5):2454-2460, (1995).
Baumann et al., "Hepatocyte-Stimulating Factor III Shares Structural and Functional Identity with Leukemia-Inhibitory Factor" J. Immonul. 143:1163-1167, (1989).
Bell and Carroll, "Leukemia inhibitory factor (LIF) suppresses proteoglycan synthesis in porcine and caprine cartilage explants" Cytokine 7(2):137-141, (1995).
Bell and Carroll, "Rheumatoid Synovial Fluid Contains Bioactive Leukemia Inhibitory Factor with Cartilage Degrading Activity—Another Target for Chondroprotective Intervention" Journal of Rheumatology 27(2):332-338, (2000).
Bell et al., "Leukemia Inhibitory Factor (LIF) Binding Protein Attenuates the Phlogistic and Abolishes the Chondral Effects of LIF in Goat Joints" Journal of Rheumatology 24(12):2394-2402, (1997).
Bell et al., "The proinflammatory and chondral activities of leukemia inhibitory factor in goat joints are partially a function of interleukin-1" Journal of Interferon Cytokine Research 19(2):197-208, (1999).
Biesinger et al., "Stable growth transformation of human-T lymphocytes by Herpesvirus saimiri" Proc. Natl. Acad. Sci. USA 89:3116-3119, (1992).
Bolivar et al., "Construction and Characterization of New Cloning Vehicles. II. A Multipurpose Cloning System" Gene 2:95-113, (1977).
Bresnihan et al., "Treatment of rheumatoid arthritis with recombinant human interleukin-1 receptor antagonist" Arthritis and Rheumatism 41(12):2196-2204, (1998).
Broxmeyer, H.E., "Is Interleukin 17, An Inducible Cytokine That Stimulates Production of Other Cytokines, Merely a Redundant Player in a Sea of Other Biomolecules?" Journal of Experimental Medicine 183:2411-2415, (1996).
Buckwalter et al., "Restoration of Injured or Degenerated Articular Cartilage" J. Am. Acad. Orthop. Surg. 2(4):192-201, (1994).
Campbell et al., "Production of Leukemia Inhibitory Factor by Human Articular Chondrocytes and Cartilage in Response to Interleukin-1 and Tumor Necrosis Factor a" Arthritis and Rheumatism 36(6):790-94, (1993).

Carroll and Bell, "Leukemia inhibitory factor stimulates proteoglycan resorption in porcine articular cartilage" Rheumatology International 13:5-8, (1993).
Carroll et al., "Antagonism of the IL-6 cytokinc subfamily—a potential strategy for more effective therapy in rheumatoid arthritis" Inflammation Research 47:1-7, (1998).
Carroll et al., "Leukemia inhibitory factor induces leukocyte infiltration and cartilage proteoglycan degradation in goat joints" Journal of Interferon and Cytokine Research 15:567-573 (1995).
Chen et al., "Chondrocyte Transplantation and Experimental Treatment Options for Articular Cartilage Defects" Amer. J. Orthop. 26(6):396-406, (1997).
Chin et al., "Interactions Between Interleukin-1 and Basic Fibroblast Growth Factor on Articular Chondrocytes. Effects on Cell Growth, Prostanoid Production, and Receptor Modulation" Arthritis Rheum. 34(3):314-324, (1991).
Coutts et al., "Effect of Growth Factors on Cartilage Repair" Amer. Acad. Orthop. Surg. (Instructional Course Lect.), Chapter 47, pp. 487-494, (1997).
Dechanet et al., "Interleukin-4 but not interleukin-10 inhibits the production of leukemia inhibitory factor by rheumatoid synovium and synoviocytes" Eur. J. Immunology 24:3222-3228 (1994).
Dudler et al., "Effect of interleukin-17 on proteoglycan degradation in murine knee joints" Ann. Rheum. Dis. 59:529-532, (2000).
Elliot et al., "Treatment of rheumatoid arthritis with chimeric monoclonal antibodies to tumor necrosis factor a" Arthritis and Rheumatism 36(12):1681-1690, (1993).
Evans and Robbins, "Getting Genes Into Human Synovium" J. Rheumatol. 24(11):2061-2063, (1997).
Evans et al., "Blocking Cytokines with Genes" J. Leukocyte Biol. 64:55-61, (1998).
Farndale et al., "Improved quantitation and discrimination of sulphated glycosaminoglycans by use of dimethylmethylene blue" Biochem. Biophys. Acta 883:173-177,(1986).
Farrell et al., "Increased concentrations of nitrite in synovial fluid and serum samples suggest increased nitric oxide synthesis in rheumatic diseases" Annals of the Rheumatic Diseases 51 (11) :1219-1222, (1992).
Ferrara et al., "Pituitary Follicular Cells Secrete and Inhibitor of Aortic Endothelial Cell Growth: Identification as Leukemia Inhibitory Factory" Proc. Natl. Acad. Sci. USA 89:698-702, (1992).
Flannery et al., "Identification of Stromelysin Cleavage Site within Interglobular Domain of Human Aggrecan" Journal of Biological Chemistry 267(2):1008-1014,(1992).
Fleckenstein and Desrosiers, "Herpesvirus saimiri and herpesvirus ateles" In the Herpesviruses, I.B. Roizman, ed., NY:Plenum Publishing Press pp. 253-332, (1982).
Florini and Roberts, "Effect of Rat Age on Blood Levels of Somatomedin-like Growth Factors" J. Gerontol 35(1):23-30, (1980).
Fosang et al., "Cleavage of Cartilage Proteoglycan between G1 and G2 Domains by Stromelysins" Journal of Biological Chemistry 266:15579-15582, (1991).
Fosang et al., "Degradation of cartilage aggrecan by collagenase-3 (MMP-13)" FEBS Letters 380:17-20 (1996).
Fosang et al., "Fibroblast and neutrophil collagenase cleave at two sites in the cartilage aggrecan interglobular domain" Biochemical Journal 295:273-276, (1993).
Fosang et al., "The interglobular domain of cartilage aggrecan is cleaved by PUMP, gelatinases and cathepsin B" Journal of Biological Chemistry 267(27):19470-19474, (1992).
Frenkel and Di Cesare, "Degradation and Repair of Articular Cartilage" Front. Biosci. 4:d671-685, (1999).
Gouin et al., "Expression of leukemia inhibitory factor by cartilage-forming tumors of bone: an immunohistochemical study" J. Orthop. Res. 17(2):301-305,(1999).
Gouin et al., "Increased levels of leukemia inhibitory factor (LIF) in urine and tissue culture supernatant from human primary bone tumours" Cytokine 10(2):110-114, (1998).
Guerne et al., "Growth Factor Responsiveness of Human Articular Chondrocytes: Distinct Profiles in Primary Chondrocytes, Subcultured Chondrocytes, and Fibroblasts." J. Cellular Physiology 158(3):476-484, (1994).

Hamilton et al., "Induction of Leukemia Inhibitory Factor in Human Synovial Fibroblasts by IL-1 and Tumor Necrosis Factor-a" Journal of Immunology 150(4):1496-1502, (1993).
Hardingham and Muir, "The specific interaction of hyaluronic acid with cartilage proteoglycan" Biochem. Biophys. Acta 279:401-405, (1972).
Hardingham, T.E., "Proteoglycans: their structure, interactions and molecular organization in cartilage" Biochemical Society Transactions 9(6):489-497 (1981).
Hardingham, T.E., "The Role of Link-Protein in the Structure of Cartilage Proteoglycan Aggregates" Biochemical Journal 177:237-247 (1979).
Hartmann and Tabin, "Dual roles of Wnt signaling during chondrogenesis in the chicken limb" Development 127:3141-3159, (2000).
Heinegard and Hascall, "Aggregation of Cartilage Proteoglycan" Journal of Biological Chemistry 249:4250-4256, (1974).
Henrotin et al., "Effects of exogenous IL-4, TNFa, IL-6, IL-8•and LIF on cytokine production by human articular chondrocytes" Osteoarthritis and Cartilage 4(3):163-173, (1996).
Hering, T.M., "Regulation of Chondrocyte Gene Expression." Front. Biosci. 4:d743-761, (1999).
Hill and Logan, "Peptide Growth Factors and their Interactions During Chondrogenesis" Progress in Growth Factor Research 4(1):45-68, (1992).
Hilton et al., "Leukemia Inhibitory Factor: A Biological Perspective" J. Cell Biochem. 46:21-26, (1991).
Hilton et al., "Specific Binding of Murine Leukemia Inhibitory Factor to Normal and Leukemic Monocyte Cells" Proc. Natl. Acad. Sci. USA 85:5971-5975 (1988).
Hui et al., "Modulation of cartilage proteoglycan metabolism by LIF binding protein" Cytokine 10(3):220-226, (1998).
Hunziker and Rosenberg, "Induction of Repair in Partial Thickness Articular Cartilage Lesions by Timed Release of•TGFP", (40th Annual Meeting, Orthop. Res. Soc., Feb. 21-24, New Orleans, LA) 19:236-41 (1994).
Jamieson et al., "Collagen-Induced Arthritis in Rats Assessment by Serial Magnification Radiography" Invest. Radiol. 20:324-330, (1985).
Joosten et al., Anticytokine treatment of established type II collagen-induced arthritis in DBA/1 mice. A comparative study using anti-TNFa, anti-IL-1a/P, and IL-1Ra Arthritis and RheumatisM 39(5):797-809, (1996).
Joosten et al., .IL-lap Blockade Prevents Cartilage and Bone Destruction in Murine Type II Collagen-Induced Arthritis, Whereas TNF-a Blockade Only Ameliorates Joint Inflammation J. Immunol., 163:5049-5055 (1999).
Jovanovic et al., "Stimulation of 92-kd gelatinase (matrix metalloproteinase 9) production by interleukin-17 in human monocyte/macrophages" Arthritis and Rheumatism 43(5):1134-1144, (2000).
Kang et al., "Ex Vivo Gene Transfer to Chondrocytes in Full-Thickness Articular Cartilage Defects: A Feasibility Study." Osteoarthritis and Cartilage. 5(2):139-143, (1997).
Kang et al., "Gene Therapy for Arthritis: Principles and Clinical Practice." Biochemical Society Transactions. 25(2):533-537, (1997).
Kim at al., "Detection of Human Leukemia Inhibitory Factor by Antibody Based ELISA" Journal Monoclonal of Immunological Methods 156:9-17 (1992).
Kimura and Kuettner, "Studies on the Synthesis and Assembly of Cartilage Proteoglycan" Articular Cartilage Biochemistry, Kuettner et al., New York:Raven Press pp. 113-124, (1986).
Kong at al., "Activated T Cells Regulate Bone Loss and Joint Destruction in Adjuvant Arthritis through Osteoprotegerin Ligand" Nature 402(6759):304-309 (1999).
Kuettner, K.E., "Biosynthesis and Characterization of Cartilage—Specific Matrix Components and Events" Articular Cartilage Biochemistry, Kuettner et al., New York:Raven Press pp. 77-79, (1986).
Lark et al., "Aggrecan Degradation in Human Cartilage" J. Clin. Invest. 100:93-106 (1997).
Lendeckel at al., "Moldulation of Wnt-5A Expression by Actinonin: Linkage of APN to the Wnt-Pathway?" Adv. Exp. Med. Biol. 477:35-41, (2000).

Lendeckel et al., "Inhibition of alanyi aminopeptidase induces MAP-kinase p42/ERK2 in the human T cell line KARPAS-299" Biochemical and Biophysical Research Communications 252(1):5-9 (1998).
Lohmander et al., "The structure of aggrccan fragments in human synovial fluid" Arthrtis Rheum. 36:1214-1222, (1993).
Lots et al., "Leukemia Inhibitory Factor Is Expressed in Cartilage and Synovium and Can Contribute to the Pathogenesis of Arthritis" J. Clin. Invest. 90:888-896 (1992.
Lubberts at al., "Reduction of Interleukin-17-Induced Inhibition of Chondrocyte Proteoglycan Synthesis in Intact Murine Articular Cartilage by Interleukin-4" Arthritis and Rheumatism 43(6):1300-1306 (2000).
Maekawa et al., "Clonal Suppression of HL60 and 13937 Cells by Recombinant Human Leukemia Inhibitory Factor in Combination with GM-CSF or G-CSF" Leukemia 3(4):270-276, (1989).
Martel-Pelletier et al., "Cytokines and Their Role in the PathoPhysiology of Osteoarthritis." Front. Bioscience. 4:d694-703, (1999).
Martel-Pelletier et al., "Mitogen-activated protein kinase and nuclear factor KB together regulate interleukin-17-induced nitric oxide production in human osteoarthritic chondrocytes" Arthritis and Rheumatism 42(11):2399-2409 (1999).
Martel-Pelletier et al., "The interleukin-1 receptor in normal and osteoarthritic human articular. chondrocytes. Identification as the type I receptor and analysis of binding kinetics and biologic function" Arthritis and Rheumatism 35(5):530-540 (1992).
Metcalf and Gearing, "Fatal Syndrome in Mice Engrafted with Cells Producing High Levels of the Leukemia Inhibitory Factor" Proc. Natl. Acad. Sci. USA 86:5948-5952 (1989).
Moran and Bogoch, "Animal Models of Rheumatoid Arthritis" Animal Models in Orthopaedic Research, An and Friedman, Boca Raton, FL:CRC Press, Chapter 19, pp. 369-390 (1999).
Mori et al., "Purification of a Lipoprotein Lipase-Inhibiting Protein Produced by a Melanoma Cell Line Associated with Cancer Cachexia" Biochem. & Biophys. Res. Com. 160(3):1085-1092 (1989).
Mow et al., "Cartilage and diarthrodial joints as paradigms for hierarchical materials and structures" Biomaterials 13(2):67-97, (1992).
Muir, H., "Proteoglycans as organizers of the intercellular matrix" Biochemical Society Transactions 11(6):613-622, (1983).
Murphy et al., "Generation of Sensory Neurons is Stimulated by Leukemia Inhibitory Factor" Proc. Nat Acad. Sci. USA 88:3498-3501, (1991).
Osborn et ate., "Growth Factor Stimulation of Adult Articular Cartilage" J. Orthoped. Res. 7(1):35-42 (1989).
Palmer et al., "Induction of nitric oxide synthase in human chondrocytes" Biochemical & Biophysical Research Communications 193(1):398-405 (1993).
Panayi et al., "The importance of the T cell in initiating and maintaining the chronic synovitis of rheumatoid arthritis" Arthritis and Rheumatism 35(7):729-735, (1992).
Pelletier et al., "Cytokines and Inflammation in Cartilage Degradation" Osteoarthritc Edition of Rheumatic Disease Clinics of North America, Moskowitz, R.W., Philadelphia:W.D. Saunders Company pp. 545-568 (1993).
Pelletier et al., "Reduced progression of experimental osteoarthritis in vivo by selective inhibition of inducible nitirc oxide synthase" Arthritis Rheum. 41(7):1275-1286, (1998).
Pelletier et al., "Reduction in the structural changes of experimental osteoarthritis by a nitric oxide inhibitor" Osteoarthritis & Cartilage 7(4):416-418, (1999).
R&D Systems, "Monoclonal Anti-Mouse IL-17 Antibody" (Product Information), (1998).
Reid et al., "Leukemia Inhibitory Factor: A Novel Bone-Active Cytokine" Endocrin. 126(3):1416-1420, (1990).
Renoux as., "Release of mast cell mediators and nitrites into knee joint fluid in osteoarthritis-comparison with articular chondrocalcinosis and rheumatoid arthritis" Osteoarthritis & Cartilage 4(3):175-179 (1996).
Rogachefsky et al., Treatment of Canine Osteoarthritis with Sodium Pentosan Polysulfate and Insulin-Like Growth Factor-1. Annals NY Acad. Sci. 732:392-394, (1994).

Rouvier et al., "CTLA-8, Cloned from an Activated T Cell, Bearing AU-Rich Messenger RNA Instability Sequences, and Homologous to a Herpesvirus Saimiri Gene" Journal of Immunology 50(12): 15445-456, (1993).

rRifas and Avioli, "A Novel T Cell Cytokine Stimulates Interleukin-6 in Human Osteoblastic Cells" Saurnal of Bone and Mineral Research 14(7):1096-1103, (1999).

Sah et al., "Differential Effects of bFGF and IGF-1 on Matrix Metabolism in Calf and Adult Bovine Cartilage Explants" Arch. Biochem. and Biophys., Academic Press, Inc. vol. 308(1):137-147, (1994).

Sakiniene et al., "Inhibition of nitric oxide synthase (NOS) aggravates *Staphylococcus aureus septicaemia* and septic arthritis" Clinical and Experimental Immunology 110(3):370-377, (1997).

Sandy et al., "The Structure of Aggrecan Fragments in Human Synovial Fluid" J. Clin. Invest. 89:1512-1516, (1992).

U.S. Appl. No. 60/113,621, filed Dec. 1998, Wood.

Albanesi et al., "IL-17 Is Produced by Nickel-Specific T Lymphocytes and Regulates ICAM-1 Expression and Chemokine Production in Human Keratinocytes: Synergistic or Antagonist Effects with IFN-y and TNF-a" Journal of Immunology 162:494-502, (1999).

Altschul and Gish, "Local Alignment Statistics" Methods in Enzymology 266:460-480, (1996).

Antonysamy et al., "Evidence for a role of IL-17 in organ allograft rejection: IL-17 promotes the functional differentiation of dendritic rejection: cell progenitors" 162(1):577-584, (1999).

Antonysamy, et al., "Evidence for a role of IL-17 in alloimmunity: a novel IL-17 antagonist promotes heart graft survival" Transplant Proc.,31 (1-2):93 (1999).

Awane et al., "NF-KB-Inducing Kinase is a Common Mediator of IL-17-TNF-a and IL-1P-Induced Chemokine Promoter Activation in Intestinal Epithelial Cells" J. Immunol. 162:5337-5344, (1999).

Chang, et al., "A novel heterodimeric cytokine consisting of IL-17 and IL-17F regulates inflammatory responses", Cell Research, vol. 17, pp. 435-440, (2007).

Fossiez, et al., "T cell interleukin-17 induces stromal cells to produce proinflammatory and hematopoietic cytokines", J. Exp. Med., vol. 183, pp. 2593-2603, (1996).

Liang, et al., "An IL-17F/A heterodimer protein is produced by mouse Th17 cells and induces airway neutrophil recruitment", The Journal of Immunology, vol. 179, pp. 7791-7799, (2007).

Sato and Urist., "Bone Morphogenetic Protein-Induced Cartilage Development in Tissue Culture." Clin. Ortho. Rel. Res. (Sect. II, Basic Science and Pathology) 183:180-187, (1984).

Schwandner et al.,. "Requirement of Tumor Necrosis Factor Receptor-associated Factor TRAF)6 in Interleukin 17 Signal Transduction" Journal of Experimental Medicine 191(7):1239-1239, (2000).

Smith, R.L., "Degradative Enzymes in Osteoarthritis" Front. Bioscience 4:d704-712, (1999).

Spriggs, M.K., "Interleukin-17. and Its Receptor" Journal of Clinical Immunology 17(5):366-369, (1997).

Stadler et al., "Articular Chondrocytes Synthesize Nitric Oxide in Response to Cytokines and Lipopolysaccharide" J. Immunol. 147:3915-3920 (1991).

Stefanovic-Racic et al., "The Role of Nitric Oxide in Proteoglycan Turnover by Bovine Articular Cartilage Organ Cultures" J. immunol 156:1213-1220 (1996).

Stichtenoth, et al., "Nitric oxide and inflammatory joint diesease", British Journal of Rhematology 37(3): 246-257, (1998).

Taskiran et al., "Nitric oxide mediates suppression of cartilage proteoglycan synthesis by interleukin-1" Biochem. & Biophys. Res. Comm 200:142-148 (1994).

Thonar et al., "Are related changes in cartilage proteoglycans", Articular cartilage Biochemistry, New york: Raven Press pp. 273-288, (1986).

Tomida et al., "Purification of a Factor Inducing Ditierentiation of Mouse Myeloid Leukemic MI Cells from Conditioned Medium of Mouse Fibroblast L929 Cells." Journal of Biological Chemistry 259(17):10978-10982, (1984).

Tomida, et al., "Characterization of a factor inducing differentiation of mouse myeloid leukemic cells purified from conditioned medium of mouse Ehrlich Ascites tumor cells", FEBS Letters, 178(2): 291-296, (1984).

Toolan et al., "Development of Novel Osteochondral Graft for Cartilage Repair." J. Biomed. Mater. Res. 41(2):244-250, (1998).

Tortorella et al., "Purification and Cloning of Aggrecanase-1: A Member of the ADAMTS Family of Proteins" Science 284:1664-1666, (1999).

Trentham et al., "Autoimmunity to ollagen: A Shared Feature of Psoriatic and Rheumatoid Arthritis" Arthrit. Rheum. 24(11):1363-1369, (1981).

Tyler et al., "Mediators of Matrix Catabolism" Articular Cartilage and Osteoarthritis, Kuettner et al., New York:Raven Press, Ltd. pps. 251-264 (1992).

van Beek et al., "Leukemia Inhibitory Factor Inhibits Osteoclastic Reabsorption, Growth, and Alkaline Phosphatase Activity in Fetal Mouse Metacarpal Bones Mineralization, in Culture" Journal Mineral ReSearch 8(2):191-198 (1993).

Van Beuningen et al., "Protection From Interleukin 1 Induced Destruction of Articular Cartilage by Transforming Growth Factor P: Studies in Anatomically Intact Cartilage In Vitro and In Vivo." Annals of Rheum. Diseases. 52(3):185-191 (1993).

Van de Loo et al., "Effect of interleukin 1 and leukaemia, inhibitory factor on chondrocyte metabolism in articular cartilage from normal and interleukin-6-deficient mice: role of nitric oxide and IL-6 in the suppression of proteoglycan synthesis" Cytokine 9(7):453-462 (1997).

Van de Loo et al., "Reduced cartilage proteoglycan loss during zymosan-induced gonarthritis in NOS2-deficient mice and in anti-interleukin-1-treated wild-type mice with unabated joint inflammation" Arthritis Rheum. 41(4):634-646, (1998).

Van de Loo et al., "Role of interleukin-1, tumor necrosis factor a, and interleukin-6 in cartilage proteoglycan metabolism and destruction. Effect of in situ blocking in murinc antigen- and zymosan-induced arthritis" Arthritis Rheum. 38(2):164-172 (Feb 1995).

Van den Berg et al., "Amelioration of established murine collagen-induced arthritis with anti-IL-1 treatment" Clin. Exp. Immunol. 95:237-248 (1994).

Van den Berg et. al., "The Mouse Patella Assay" Rheum. Int. 1:165-169, (1982).

Van der Kraan at al , "Inhibition of Proteoglycan Synthesis by Transforming Growth Factor β in Anatomically Intact Articular Cartilage of Murine Patellae" Annals Rheum. Dis. 51(5):643-647, (1992).

Verschure et al., "Responsiveness of articular cartilage from normal and inflamed mouse knee joints to various growth factors" Annals Rheum. Dis. 53(7):455-460 (1994).

Villiger, et al., "Induction to Cytokine expression by leukemia inhibitory factor", Journal of clinical Investigation, 91: 1575-1581, (1993).

Wark, et al., "Latest technologies for the enhancement of antibody affinity", Advanced drug delivery reviews, vol. 58, pp. 657-670, (2006).

Wright, et al., "The human IL-17F/IL-17A hetrodimeric cytokine signals through the IL-17RA/IL17RC receptor complex", The Journal of Immunology, vol. 181, pp. 2799-2805, (2008).

Yamamori et al., "The Cholinergic Neuronal Differentiation Factor from Heart Cells is Identical to Leukemia Inhibitory Factor" Science 246:1412-1416 (1989).

Ziolkowska et al., "High Levels of IL-17 in Rheumatoid Arthritis Patients: IL-15 Triggers In Vitro IL-17 Production Via Cyclosporin A-Sensitive Mechanism" Journal of Immunology 164(5):2832-2838, (2000).

A)

B)

C)

D)

E)

F)

SEQUENCE LISTING

```
<160> NUMBER OF SEQ ID NOS: 105

<210> SEQ ID NO 1
<211> LENGTH: 375
<212> TYPE: DNA
<213> ORGANISM: Homo sapiens

<400> SEQUENCE: 1
caggtgcagc tggtgcagtc tgggggaggc ttggtacagc ctggcaggtc cctgagactc      60
tcctgtgcag cctctggatt caccttttgat gattatgcca tgcactgggt ccggcaagct    120
ccagggaagg gcctggagtg ggtctcaggt attagttgga atagtggtac cataggctat    180
gcggactctg tgaagggccg attcaccatc tccagagaca acgccaagaa ctccctgtat    240
ctgcaaatga acagtctgag agctgaggac acggccttgt attactgtgc aaaagaactg    300
tatatcagtg actgggactc ctactcctac ggtatggacg tctggggcca agggaccacg    360
gtcaccgtct cctca                                                       375

<210> SEQ ID NO 2
<211> LENGTH: 125
<212> TYPE: PRT
<213> ORGANISM: Homo sapiens

<400> SEQUENCE: 2

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Thr Ile Gly Tyr Ala Asp Ser Val
        50                  55                  60

Lys Gly Arg Phe Thr Ile Ser Arg Asp Asn Ala Lys Asn Ser Leu Tyr
    65                  70                  75                  80

Leu Gln Met Asn Ser Leu Arg Ala Glu Asp Thr Ala Leu Tyr Tyr Cys
                85                  90                  95

Ala Lys Glu Leu Tyr Ile Ser Asp Trp Asp Ser Tyr Ser Tyr Gly Met
            100                 105                 110

Asp Val Trp Gly Gln Gly Thr Thr Val Thr Val Ser Ser
        115                 120                 125
```

<210> SEQ ID NO 3
<211> LENGTH: 318
<212> TYPE: DNA
<213> ORGANISM: Homo sapiens

<400> SEQUENCE: 3

```
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcaccttt cggcggaggg   300
accaaggtgg agatcaaa                                                  318
```

<210> SEQ ID NO 4
<211> LENGTH: 106
<212> TYPE: PRT
<213> ORGANISM: Homo sapiens

<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Gly Gly Gly Thr Lys Val Glu Ile Lys
            100                 105

<210> SEQ ID NO 5
<211> LENGTH: 372
<212> TYPE: DNA
<213> ORGANISM: Homo sapiens

<400> SEQUENCE: 5

```
gaggtgcagc tggtggagtc tgggggaggc ttggtaaagc ctggggggtc ccttagactc    60
tcctgtgcag cctctggatt cactttcagt aacgcctgga tgagctgggt ccgccaggct   120
ccagggaagg ggctggaatg ggttggccgt attaaaagca aaactgatgg tgggacaaca   180
gactacgttg cacccgtgaa aggcagattc accatctcaa gagatgattc aaaaaacacc   240
ctgtatctgc aaatgaacag cctgaaaacc gaggacacag ccgtatatta ctgtaccaca   300
tcgtatagca gttactggtt cccctactac tttgactact ggggccaggg aaccctggtc   360
accgtctcct ca                                                        372
```

<210> SEQ ID NO 6
<211> LENGTH: 124
<212> TYPE: PRT
<213> ORGANISM: Homo sapiens

<400> SEQUENCE: 6

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Val Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
            85                  90                  95

Tyr Cys Thr Thr Ser Tyr Ser Ser Tyr Trp Pro Tyr Tyr Phe Asp
            100                 105                 110

Tyr Trp Gly Gln Gly Thr Leu Val Thr Val Ser Ser
        115                 120
```

```
<210> SEQ ID NO 7
<211> LENGTH: 321
<212> TYPE: DNA
<213> ORGANISM: Homo sapiens

<400> SEQUENCE: 7
gacatccaga tgacccagtc tccatcctca ctgtctgcat ctgtaggaga cagagtcacc      60
atcacttgtc gggcgagtca gggtattagc agctggttag cctggtatca gcagaaacca    120
gagaaagccc ctaagtccct gatctatgct gcatccagtt tgcaaagtgg ggtcccatca    180
aggttcagcg gcagtggatc tgggacagat ttcactctca ccatcagcag cctgcagcct    240
gaagattttg caacttatta ctgccaacag tataatagtt acccgatcac cttcggccaa    300
gggacacgac tggagattaa a                                              321

<210> SEQ ID NO 8
<211> LENGTH: 107
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
            85                  90                  95

Thr Phe Gly Gln Gly Thr Arg Leu Glu Ile Lys
            100                 105

<210> SEQ ID NO 9
<211> LENGTH: 357
<212> TYPE: DNA
<213> ORGANISM: Homo sapiens
```

<400> SEQUENCE: 9

```
caggtgcagc tggtgcagtc tggggctgag gtgaagaagc ctggggcctc agtgaaggtt      60
tcctgcaagg catctggata caccttcacc atctattatt tgcactgggt gcgacaggcc     120
cctggacaag gcttgagtg gatgggaata atcaacccta gtggtggtag acaaactac       180
gcacagaagt tccagggcag ggtcaccatg accagggacc cgtccacgaa cacagtctac     240
atggaactga gcagcctgac atctgaggac gcggccgtgt attactgtgc gagagggaa      300
tttagcagtg gctggcttga ctactggggc caagggacca cggtcaccgt ctcctca       357
```

<210> SEQ ID NO 10
<211> LENGTH: 119
<212> TYPE: PRT
<213> ORGANISM: Homo sapiens

<400> SEQUENCE: 10

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ile Tyr
            20                  25                  30
Tyr Leu His Trp Val Arg Gln Ala Pro Gly Gln Gly Leu Glu Trp Met
        35                  40                  45
Gly Ile Ile Asn Pro Ser Gly Gly Arg Thr Asn Tyr Ala Gln Lys Phe
    50                  55                  60
Gln Gly Arg Val Thr Met Thr Arg Asp Pro Ser Thr Asn Thr Val Tyr
65                  70                  75                  80
Met Glu Leu Ser Ser Leu Thr Ser Glu Asp Ala Ala Val Tyr Tyr Cys
                85                  90                  95
Ala Arg Gly Glu Phe Ser Ser Gly Trp Leu Asp Tyr Trp Gly Gln Gly
            100                 105                 110
Thr Thr Val Thr Val Ser Ser
        115
```

<210> SEQ ID NO 11
<211> LENGTH: 321
<212> TYPE: DNA
<213> ORGANISM: Homo sapiens

<400> SEQUENCE: 11

```
gacatccaga tgacccagtc tccatcttcc gtgtctgcat ctgtaggaga cagagtcacc      60
atcacttgtc gggcgagtca gggtattagc agctggttag cctggtatca gcataaacca     120
gggaaagccc ctaagctcct gatctatgct gcatccagtt tgcaaagtgg ggtcccatca     180
aggttcagcg gcagtggatc tgggacagat ttcactctca ccatcagcag cctgcagcct     240
gaagattttg caacttacta ttgtcaacag gctaatagtt tcccgctcac tttcggcgga     300
gggaccaagg tggagatcaa a                                               321
```

<210> SEQ ID NO 12
<211> LENGTH: 107
<212> TYPE: PRT
<213> ORGANISM: Homo sapiens

<400> SEQUENCE: 12

```
Asp Ile Gln Met Thr Gln Ser Pro Ser Ser Val Ser Ala Ser Val Gly
1               5                   10                  15
Asp Arg Val Thr Ile Thr Cys Arg Ala Ser Gln Gly Ile Ser Ser Trp
            20                  25                  30
```

```
Leu Ala Trp Tyr Gln His Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Leu
                 85                  90                  95

Thr Phe Gly Gly Gly Thr Lys Val Glu Ile Lys
                100                 105
```

<210> SEQ ID NO 13
<211> LENGTH: 378
<212> TYPE: DNA
<213> ORGANISM: Homo sapiens

<400> SEQUENCE: 13

```
gaggtgcagc tggtggagtc tgggggaggc ttggtacagc ctggggggtc cctgagactc      60
tcctgtgcag cctctggatt caccttcagt agctatagca tgaactgggt ccgccaggct     120
ccagggaagg ggctggagtg ggtttcatac attagtggtg gtagtagtac catatactac     180
gcagactctg tgaagggccg attcaccatc tccagagaca atgccaagaa ctcactgtat     240
ctgcaaatga acagcctgag agacgaggac acggctgtgt attactgtgc gagagagggc     300
tatgtttcgg ggacctatta caactactac tacggtatgg acgtctgggg ccaagggacc     360
acggtcaccg tctcctca                                                   378
```

<210> SEQ ID NO 14
<211> LENGTH: 126
<212> TYPE: PRT
<213> ORGANISM: Homo sapiens

<400> SEQUENCE: 14

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ser Met Asn Trp Val Arg Gln Ala Pro Gly Lys Gly Leu Glu Trp Val
         35                  40                  45

Ser Tyr Ile Ser Gly Gly Ser Ser Thr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Arg Glu Gly Tyr Val Ser Gly Thr Tyr Tyr Asn Tyr Tyr Tyr Gly
            100                 105                 110

Met Asp Val Trp Gly Gln Gly Thr Thr Val Thr Val Ser Ser
        115                 120                 125
```

<210> SEQ ID NO 15
<211> LENGTH: 321
<212> TYPE: DNA
<213> ORGANISM: Homo sapiens

<400> SEQUENCE: 15

```
gaaattgtgt tgacccagtc tccagccacc ctgtctttgt ctccagggga aagagccacc      60
ctctcctgca gggccagtca gagtgttagc agttacttag cctggtacca acagaaacct     120
```

```
ggccaggctc ccaggctcct catctatgat gcacccaaca gggccactgg catcccagcc    180
aggttcagtg gcagtgggtc tgggacagac ttcactctca ccatcagcag cctagagcct    240
gaagattttg cagttttatta ctgtcagcag cgtagcaact ggtcgctcac tttcggcgga   300
gggaccaagg tggagatcaa a                                              321
```

<210> SEQ ID NO 16
<211> LENGTH: 107
<212> TYPE: PRT
<213> ORGANISM: Homo sapiens

<400> SEQUENCE: 16

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Pro Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Ser Leu
                85                  90                  95

Thr Phe Gly Gly Gly Thr Lys Val Glu Ile Lys
            100                 105
```

<210> SEQ ID NO 17
<211> LENGTH: 363
<212> TYPE: DNA
<213> ORGANISM: Homo sapiens

<400> SEQUENCE: 17

```
gaggtgcagc tgttggagtc tgggggaggc ttggtacagc ctggggggtc cctgagactc    60
tcctgtgcag cctctggatt cacctttagc agctatgtca tgagctgggt ccgccaggtt    120
ccagggaagg gctggagtg gtctcagct attagtggtc gtggtggtaa cacattctac     180
gcagactccg tgaagggccg gttcaccatc tccagagaca attccaagaa cacgctgtat   240
ctgcaaatgg acagcctgag agccgaggac acggccgtat attactgtgc gaaagatgat   300
cggcgtatag cagcaggtag ttttgactat tggggccaag gaccacggt caccgtctcc    360 tca                                                                 363
```

<210> SEQ ID NO 18
<211> LENGTH: 121
<212> TYPE: PRT
<213> ORGANISM: Homo sapiens

<400> SEQUENCE: 18

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Ser Trp Val Arg Gln Val Pro Gly Lys Gly Leu Glu Trp Val
        35                  40                  45

Ser Ala Ile Ser Gly Arg Gly Gly Asn Thr Phe Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asp Ser Leu Arg Ala Glu Asp Thr Ala Val Tyr Tyr Cys
                 85                  90                  95

Ala Lys Asp Asp Arg Arg Ile Ala Ala Gly Ser Phe Asp Tyr Trp Gly
            100                 105                 110

Gln Gly Thr Thr Val Thr Val Ser Ser
        115                 120

<210> SEQ ID NO 19
<211> LENGTH: 321
<212> TYPE: DNA
<213> ORGANISM: Homo sapiens

<400> SEQUENCE: 19
gccatccagt tgacccagtc tccatcctcc ctgtctgcat ctgtaggaga cagagtcacc    60
atcacttgcc gggcaagtca gggcattagc agtgctttag cctggtatca gcagaaacca   120
gggaaagctc ctaagctcct gatctatgat gtctccagtt tggaaagtgg ggtcccatca   180
aggttcagcg gcagtggatc tgggacagat ttcactctca ccatcagcag cctgcagcct   240
gaagattttg caacttatta ctgtcaacag tttaatagtt accctctcac tttcggcgga   300
gggaccaagg tggagatcaa a                                             321

<210> SEQ ID NO 20
<211> LENGTH: 107
<212> TYPE: PRT
<213> ORGANISM: Homo sapiens

<400> SEQUENCE: 20

Ala Ile Gln Leu Thr Gln Ser Pro Ser Ser Leu Ser Ala Ser Val Gly
  1               5                  10                  15

Asp Arg Val Thr Ile Thr Cys Arg Ala Ser Gln Gly Ile Ser Ser Ala
             20                  25                  30

Leu Ala Trp Tyr Gln Gln Lys Pro Gly Lys Ala Pro Lys Leu Leu Ile
         35                  40                  45

Tyr Asp Val Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Leu
                 85                  90                  95

Thr Phe Gly Gly Gly Thr Lys Val Glu Ile Lys
            100                 105

<210> SEQ ID NO 21
<211> LENGTH: 378
<212> TYPE: DNA
<213> ORGANISM: Homo sapiens

<400> SEQUENCE: 21
gaggtgcagc tggtggagtc tgggggaggc ttggtacagc ggggggggtc cctgagactc    60
tcctgtgcag cctctggatt caccttcagt agctatagca tgaactgggt ccgccaggct   120
ccagggaagg ggctggagtg gatttcatac attagtagta gtagtagtgc catatactac   180
gcagactctg tgaagggccg attcaccatc tccagagaca atgccaagaa ctcactgtat   240
ctgcaaatga acagcctgag agacgaggac acggctgtgt attactgtgc gagagagggc   300
tatgcttcgg ggaggtatta caactactac tacggtatgg acgtctgggg ccaagggacc   360
```

```
acggtcaccg tctcctca                                                     378
```

<210> SEQ ID NO 22
<211> LENGTH: 126
<212> TYPE: PRT
<213> ORGANISM: Homo sapiens

<400> SEQUENCE: 22

```
Glu Val Gln Leu Val Glu Ser Gly Gly Gly Leu Val Gln Arg Gly Gly
1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Ile
        35                  40                  45

Ser Tyr Ile Ser Ser Ser Ser Ala Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Gly Tyr Ala Ser Gly Arg Tyr Tyr Asn Tyr Tyr Tyr Gly
            100                 105                 110

Met Asp Val Trp Gly Gln Gly Thr Thr Val Thr Val Ser Ser
        115                 120                 125
```

<210> SEQ ID NO 23
<211> LENGTH: 321
<212> TYPE: DNA
<213> ORGANISM: Homo sapiens

<400> SEQUENCE: 23

```
gaaattgtgt tgacgcagtc tccagccacc ctgtctttgt ctccagggga aagagccacc    60
ctctcctgca gggccagtca gagtgttagc agctacttgg cctggtacca acagaaacct   120
ggccaggctc ccaggctcct catctatgat gcatccaaca gggccactgg catcccagcc   180
aggttcagtg tcagtgggtc tgggacagac ttcactctca ccatcagcag cctagagcct   240
gaagattttg cggtttatta ctgtcagcag cgtagcagct ggtcgctcac tttcggcgga   300
gggaccaagg tggagatcaa a                                             321
```

<210> SEQ ID NO 24
<211> LENGTH: 107
<212> TYPE: PRT
<213> ORGANISM: Homo sapiens

<400> SEQUENCE: 24

```
Glu Ile Val Leu Thr Gln Ser Pro Ala Thr Leu Ser Leu Ser Pro Gly
1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Val
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Ser Trp Ser Leu
                85                  90                  95
```

Thr Phe Gly Gly Gly Thr Lys Val Glu Ile Lys
            100                 105

<210> SEQ ID NO 25
<211> LENGTH: 291
<212> TYPE: DNA
<213> ORGANISM: Homo sapiens

<400> SEQUENCE: 25
tcctgtgcag cctctggatt cacctttgat gattatgcca tgcactgggt ccggcaagct      60
ccagggaagg gcctggagtg ggtctcaggt attagttgga atagtggtag cagaggctat     120
gcggactctg tgaagggccg attcaccatc tccagagaca acgccaagaa ctccctgtat     180
ctgcaaatga acagtctgag agctgaggac acggccttgt attactgtgc aaaagatatg     240
gtctacgctt tggacgtctg gggccaaggg accacggtca ccgtctcctc a              291

<210> SEQ ID NO 26
<211> LENGTH: 117
<212> TYPE: PRT
<213> ORGANISM: Homo sapiens

<400> SEQUENCE: 26

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Arg Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Met Val Tyr Ala Leu Asp Val Trp Gly Gln Gly Thr Thr
            100                 105                 110

Val Thr Val Ser Ser
        115

<210> SEQ ID NO 27
<211> LENGTH: 318
<212> TYPE: DNA
<213> ORGANISM: Homo sapiens

<400> SEQUENCE: 27
gaaattgtgt tgacgcagtc tccaggcacc ctgtctttgt ctccagggga aagagccacc      60
ctctcctgca gggccagtca gagttttagc ggcagctact tagcctggta ccagcagaaa     120
cctggccagg ctcccaggct cctcatctat gatacatcca gcagggccac tggcatccca     180
gacaggttca gtggcagtgg gtctgggaca gacttcactc tcaccatcag cagactggag     240
cctgaagatt ttgcagtgta ttactgtcag cagtatggta cgtggacgtt cggccaaggg     300
accaaggtgg aaatcaaa                                                   318

<210> SEQ ID NO 28
<211> LENGTH: 106
<212> TYPE: PRT
<213> ORGANISM: Homo sapiens -continued

```
<400> SEQUENCE: 28

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Phe Ser Gly Ser
            20                  25                  30

Tyr Leu Ala Trp Tyr Gln Gln Lys Pro Gly Gln Ala Pro Arg Leu Leu
        35                  40                  45

Ile Tyr Asp Thr Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Trp Thr
                85                  90                  95

Phe Gly Gln Gly Thr Lys Val Glu Ile Lys
            100                 105

<210> SEQ ID NO 29
<211> LENGTH: 354
<212> TYPE: DNA
<213> ORGANISM: Homo sapiens

<400> SEQUENCE: 29
gaggtgcagt tgttggagtc tgggggaggc ttggtacagc ctgggggtc cctgagactc      60 tcctgtgcag cctctggatt caccttagc agctatgcca tgaactgggt ccgccaggct    120
ccagggaagg gctggagtg gtctcaact attagtggtc gtggtggtag catatactac     180
gcagactccg tgaagggccg gttcaccatc tccagagaca attccaagaa cacgctgtat   240
ctgcaaatga acagcctgag agccgaggac acggccgtat attactgtgc gaaagaggag   300
gctacctggg actttgacta ctggggccaa gggaccacgg tcaccgtctc ctca         354

<210> SEQ ID NO 30
<211> LENGTH: 118
<212> TYPE: PRT
<213> ORGANISM: Homo sapiens

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Gly Arg Gly Gly Ser Ile Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Glu Ala Thr Trp Asp Phe Asp Tyr Trp Gly Gln Gly Thr
            100                 105                 110

Thr Val Thr Val Ser Ser
        115

<210> SEQ ID NO 31
<211> LENGTH: 321
<212> TYPE: DNA
<213> ORGANISM: Homo sapiens
```

<400> SEQUENCE: 31

```
gaaattgtgt tgacacagtc tccagccacc ctgtctttgt ctccagggga aagagccacc      60
ctctcctgca gggccagtca gagtgttagc agcttcttag cctggttcca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggcctccgac gttcggccaa    300
gggaccaagg tggaaatcaa a                                              321
```

<210> SEQ ID NO 32
<211> LENGTH: 107
<212> TYPE: PRT
<213> ORGANISM: Homo sapiens

<400> SEQUENCE: 32

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Phe
            20                  25                  30
Leu Ala Trp Phe Gln Gln Lys Pro Gly Gln Ala Pro Arg Leu Leu Ile
        35                  40                  45
Tyr Asp Ala Ser Asn Arg Ala Thr Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Arg Ser Asn Trp Pro Pro
                85                  90                  95
Thr Phe Gly Gln Gly Thr Lys Val Glu Ile Lys
            100                 105
```

<210> SEQ ID NO 33
<211> LENGTH: 366
<212> TYPE: DNA
<213> ORGANISM: Homo sapiens

<400> SEQUENCE: 33

```
caggtgcaac tggtggagtc tgggggaggc ttggtcaagc ctggagggtc cctgagactc     60
tcctgtgcag cctctggatt caccttcagt aactactaca tgacctggat ccgccaggct    120
ccagggaagg ggctggagtg gatttcatac attagtagta ctggtggtaa catctactac    180
gcagactctg tgaagggccg attcaccatc tccagggaca acgcccagaa ttcactgtat    240
ctgcaaatga acagcctgag agccgaggac acggctgtgt attactgtgc gagagatggg    300
ggtgtaataa tctcaactgc tatgtttgac tattggggcc aagggaccac ggtcaccgtc    360
tcctca                                                              366
```

<210> SEQ ID NO 34
<211> LENGTH: 122
<212> TYPE: PRT
<213> ORGANISM: Homo sapiens

<400> SEQUENCE: 34

```
Gln Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asn Tyr
            20                  25                  30
```

Tyr Met Thr Trp Ile Arg Gln Ala Pro Gly Lys Gly Leu Glu Trp Ile
            35                  40                  45

Ser Tyr Ile Ser Ser Thr Gly Gly Asn Ile Tyr Tyr Ala Asp Ser Val
    50                  55                  60

Lys Gly Arg Phe Thr Ile Ser Arg Asp Asn Ala Gln Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Val Ile Ile Ser Thr Ala Met Phe Asp Tyr Trp
            100                 105                 110

Gly Gln Gly Thr Thr Val Thr Val Ser Ser
            115                 120

<210> SEQ ID NO 35
<211> LENGTH: 321
<212> TYPE: DNA
<213> ORGANISM: Homo sapiens

<400> SEQUENCE: 35
gccatccagt tgacccagtc tccctcctcc ctgtctgcat ctgtaggaga cagagtcacc    60
atcacttgcc gggcaagtca gggcattagc agtgctttag cctggtatca gcagaaacca   120
gggaaagctc ctaagctcct gatctatgat gcctccagtt tggaaagtgg ggtcccatca   180
aggctcagcg gcagtggatc tgggacagat ttcactctca ccatcagcag cctgcagcct   240
gaagattttg caacttatta ctgtcaacag tttaatagtt acccgctcac tttcggcgga   300
gggaccaagg tggagatcaa a                                             321

<210> SEQ ID NO 36
<211> LENGTH: 107
<212> TYPE: PRT
<213> ORGANISM: Homo sapiens

<400> SEQUENCE: 36

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Leu Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 37
<211> LENGTH: 378
<212> TYPE: DNA
<213> ORGANISM: Homo sapiens

<400> SEQUENCE: 37
gaagtgcagc tggtggagtc tgggggaggc ttggtacagc ctggcaggtc cctgagactc    60
tcctgtgcag cctctggatt cacctttgat gattgtgcca tgcactgggt ccggcaagct   120
ccagggaagg gcctggaatg ggtctcaggt attagttgga atagtggtag cgtatactat   180

```
gcggactctg tgaagggccg attcaccatc tccagagaca acgccaagaa ttccctgtat    240
ctgcaaatga acagtctgag agctgaggac acggccttgt attactgtac aaaagaaaaa    300
tacaactgga acgacgaggg ggaatacttc tacggaatgg acgtctgggg ccaagggacc    360
acggtcaccg tctcctca                                                  378
```

<210> SEQ ID NO 38
<211> LENGTH: 126
<212> TYPE: PRT
<213> ORGANISM: Homo sapiens

<400> SEQUENCE: 38

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Cys
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Val Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Thr Lys Glu Lys Tyr Asn Trp Asn Asp Glu Gly Glu Tyr Phe Tyr Gly
            100                 105                 110

Met Asp Val Trp Gly Gln Gly Thr Thr Val Thr Val Ser Ser
        115                 120                 125
```

<210> SEQ ID NO 39
<211> LENGTH: 315
<212> TYPE: DNA
<213> ORGANISM: Homo sapiens

<400> SEQUENCE: 39

```
gaaattgtgt tgacacagtc tccaggcacc ctgtctttgt ctccagggga agagccacc     60 ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctctttcgg cggagggacc    300
aaggtggaga tcaaa                                                     315
```

<210> SEQ ID NO 40
<211> LENGTH: 105
<212> TYPE: PRT
<213> ORGANISM: Homo sapiens

<400> SEQUENCE: 40

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60
```

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Phe
                85                  90                  95

Gly Gly Gly Thr Lys Val Glu Ile Lys
            100                 105

<210> SEQ ID NO 41
<211> LENGTH: 378
<212> TYPE: DNA
<213> ORGANISM: Homo sapiens

<400> SEQUENCE: 41
gaggtgcagc tggtggagtc tgggggaggc ttggtacagc ctgggggtc cctgagactc      60 tcctgtgcag cctctggatt caccttcagt agctatagca tgaactgggt ccgccaggct   120
ccagggaagg ggctggagtg ggtttcatac attagtagtg gtagtagtac catatactac   180
gcagactctg tgaagggccg attcaccatc tccagagaca atgccaagaa ctcactgtat   240
ctgcaaatga acagcctgag agacgaggac acggctgtgt attactgtgc gagagagggc   300
tatgtttcgg ggacctatta caactactac tacggtatgg acgtctgggg ccaagggacc   360
acggtcaccg tctcctca                                                  378

<210> SEQ ID NO 42
<211> LENGTH: 126
<212> TYPE: PRT
<213> ORGANISM: Homo sapiens

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Gly Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Gly Tyr Val Ser Gly Thr Tyr Tyr Asn Tyr Tyr Tyr Gly
            100                 105                 110

Met Asp Val Trp Gly Gln Gly Thr Thr Val Thr Val Ser Ser
        115                 120                 125

<210> SEQ ID NO 43
<211> LENGTH: 321
<212> TYPE: DNA
<213> ORGANISM: Homo sapiens

<400> SEQUENCE: 43
gaaattgtgt tgacgcagtc tccagccacc ctgtctttgt ctccagggga aagagccacc      60
ctctcctgca gggccagtca gagtgttagc agttacttag cctggtacca acagaaacct   120
ggccaggctc ccaggctcct catctatgat gcacccaaca gggccactgg catcccagcc   180
aggttcagtg gcagtgggtc tgggacagac ttcactctca ccatcagcag cctagagcct   240

```
gaagattttg cagtttatta ctgtcagcag cgtagcaact ggtcgctcac tttcggcgga    300
gggaccaagg tggagatcaa a                                              321
```

<210> SEQ ID NO 44
<211> LENGTH: 107
<212> TYPE: PRT
<213> ORGANISM: Homo sapiens

<400> SEQUENCE: 44

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Pro Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Ser Leu
                85                  90                  95

Thr Phe Gly Gly Gly Thr Lys Val Glu Ile Lys
            100                 105

<210> SEQ ID NO 45
<211> LENGTH: 5
<212> TYPE: PRT
<213> ORGANISM: Homo sapiens

<400> SEQUENCE: 45

Ile Tyr Tyr Leu His
1               5

<210> SEQ ID NO 46
<211> LENGTH: 16
<212> TYPE: PRT
<213> ORGANISM: Homo sapiens

<400> SEQUENCE: 46

Ile Ile Asn Pro Ser Gly Gly Arg Thr Asn Tyr Ala Gln Phe Gln Gly
1               5                   10                  15

<210> SEQ ID NO 47
<211> LENGTH: 10
<212> TYPE: PRT
<213> ORGANISM: Homo sapiens

<400> SEQUENCE: 47

Gly Glu Phe Ser Ser Gly Trp Leu Asp Tyr
1               5                   10

<210> SEQ ID NO 48
<211> LENGTH: 5
<212> TYPE: PRT
<213> ORGANISM: Homo sapiens

<400> SEQUENCE: 48

Ser Tyr Ser Met Asn
1               5

<210> SEQ ID NO 49
<211> LENGTH: 17

```
<212> TYPE: PRT
<213> ORGANISM: Homo sapiens

<400> SEQUENCE: 49

Tyr Ile Ser Gly Gly Ser Ser Thr Ile Tyr Tyr Ala Asp Ser Val Lys
1               5                   10                  15

Gly

<210> SEQ ID NO 50
<211> LENGTH: 17
<212> TYPE: PRT
<213> ORGANISM: Homo sapiens

<400> SEQUENCE: 50

Glu Gly Tyr Val Ser Gly Thr Tyr Tyr Asn Tyr Tyr Gly Met Asp
1               5                   10                  15

Val

<210> SEQ ID NO 51
<211> LENGTH: 5
<212> TYPE: PRT
<213> ORGANISM: Homo sapiens

<400> SEQUENCE: 51

Ser Tyr Val Met Ser
1               5

<210> SEQ ID NO 52
<211> LENGTH: 17
<212> TYPE: PRT
<213> ORGANISM: Homo sapiens

<400> SEQUENCE: 52

Ala Ile Ser Gly Arg Gly Gly Asn Thr Phe Tyr Ala Asp Ser Val Lys
1               5                   10                  15

Gly

<210> SEQ ID NO 53
<211> LENGTH: 12
<212> TYPE: PRT
<213> ORGANISM: Homo sapiens

<400> SEQUENCE: 53

Asp Asp Arg Arg Ile Ala Ala Gly Ser Phe Asp Tyr
1               5                   10

<210> SEQ ID NO 54
<211> LENGTH: 17
<212> TYPE: PRT
<213> ORGANISM: Homo sapiens

<400> SEQUENCE: 54

Tyr Ile Ser Ser Ser Ser Ser Ala Ile Tyr Tyr Ala Asp Ser Val Lys
1               5                   10                  15

Gly

<210> SEQ ID NO 55
<211> LENGTH: 17
<212> TYPE: PRT
<213> ORGANISM: Homo sapiens

<400> SEQUENCE: 55

Glu Gly Tyr Ala Ser Gly Arg Tyr Tyr Asn Tyr Tyr Tyr Gly Met Asp
```

```
                1               5                   10                  15
Val

<210> SEQ ID NO 56
<211> LENGTH: 5
<212> TYPE: PRT
<213> ORGANISM: Homo sapiens

<400> SEQUENCE: 56

Asp Tyr Ala Met His
1               5

<210> SEQ ID NO 57
<211> LENGTH: 17
<212> TYPE: PRT
<213> ORGANISM: Homo sapiens

<400> SEQUENCE: 57

Gly Ile Ser Trp Asn Ser Gly Thr Ile Gly Tyr Ala Asp Ser Val Lys
1               5                   10                  15
Gly

<210> SEQ ID NO 58
<211> LENGTH: 16
<212> TYPE: PRT
<213> ORGANISM: Homo sapiens

<400> SEQUENCE: 58

Glu Leu Tyr Ile Ser Asp Trp Asp Ser Tyr Ser Tyr Gly Met Asp Val
1               5                   10                  15

<210> SEQ ID NO 59
<211> LENGTH: 5
<212> TYPE: PRT
<213> ORGANISM: Homo sapiens

<400> SEQUENCE: 59

Asn Ala Trp Met Ser
1               5

<210> SEQ ID NO 60
<211> LENGTH: 19
<212> TYPE: PRT
<213> ORGANISM: Homo sapiens

<400> SEQUENCE: 60

Arg Ile Lys Ser Lys Thr Asp Gly Gly Thr Thr Asp Tyr Val Ala Pro
1               5                   10                  15
Val Lys Gly

<210> SEQ ID NO 61
<211> LENGTH: 13
<212> TYPE: PRT
<213> ORGANISM: Homo sapiens

<400> SEQUENCE: 61

Ser Tyr Ser Ser Tyr Trp Phe Pro Tyr Tyr Phe Asp Tyr
1               5                   10

<210> SEQ ID NO 62
<211> LENGTH: 17
<212> TYPE: PRT
<213> ORGANISM: Homo sapiens
```

```
<400> SEQUENCE: 62

Gly Ile Ser Trp Asn Ser Gly Ser Arg Gly Tyr Ala Asp Ser Val Lys
1               5                   10                  15

Gly

<210> SEQ ID NO 63
<211> LENGTH: 8
<212> TYPE: PRT
<213> ORGANISM: Homo sapiens

<400> SEQUENCE: 63

Asp Met Val Tyr Ala Leu Asp Val
1               5

<210> SEQ ID NO 64
<211> LENGTH: 5
<212> TYPE: PRT
<213> ORGANISM: Homo sapiens

<400> SEQUENCE: 64

Ser Tyr Ala Met Asn
1               5

<210> SEQ ID NO 65
<211> LENGTH: 17
<212> TYPE: PRT
<213> ORGANISM: Homo sapiens

<400> SEQUENCE: 65

Thr Ile Ser Gly Arg Gly Gly Ser Ile Tyr Tyr Ala Asp Ser Val Lys
1               5                   10                  15

Gly

<210> SEQ ID NO 66
<211> LENGTH: 9
<212> TYPE: PRT
<213> ORGANISM: Homo sapiens

<400> SEQUENCE: 66

Glu Glu Ala Thr Trp Asp Phe Asp Tyr
1               5

<210> SEQ ID NO 67
<211> LENGTH: 5
<212> TYPE: PRT
<213> ORGANISM: Homo sapiens

<400> SEQUENCE: 67

Asn Tyr Tyr Met Thr
1               5

<210> SEQ ID NO 68
<211> LENGTH: 17
<212> TYPE: PRT
<213> ORGANISM: Homo sapiens

<400> SEQUENCE: 68

Tyr Ile Ser Ser Thr Gly Gly Asn Ile Tyr Tyr Ala Asp Ser Val Lys
1               5                   10                  15

Gly

<210> SEQ ID NO 69
<211> LENGTH: 13
```

```
<212> TYPE: PRT
<213> ORGANISM: Homo sapiens

<400> SEQUENCE: 69

Asp Gly Gly Val Ile Ile Ser Thr Ala Met Phe Asp Tyr
1               5                   10

<210> SEQ ID NO 70
<211> LENGTH: 5
<212> TYPE: PRT
<213> ORGANISM: Homo sapiens

<400> SEQUENCE: 70

Asp Cys Ala Met His
1               5

<210> SEQ ID NO 71
<211> LENGTH: 17
<212> TYPE: PRT
<213> ORGANISM: Homo sapiens

<400> SEQUENCE: 71

Gly Ile Ser Trp Asn Ser Gly Ser Val Tyr Tyr Ala Asp Ser Val Lys
1               5                   10                  15

Gly

<210> SEQ ID NO 72
<211> LENGTH: 17
<212> TYPE: PRT
<213> ORGANISM: Homo sapiens

<400> SEQUENCE: 72

Glu Lys Tyr Asn Trp Asn Asp Glu Gly Glu Tyr Phe Tyr Gly Met Asp
1               5                   10                  15

Val

<210> SEQ ID NO 73
<211> LENGTH: 17
<212> TYPE: PRT
<213> ORGANISM: Homo sapiens

<400> SEQUENCE: 73

Tyr Ile Ser Ser Gly Ser Ser Thr Ile Tyr Tyr Ala Asp Ser Val Lys
1               5                   10                  15

Gly

<210> SEQ ID NO 74
<211> LENGTH: 11
<212> TYPE: PRT
<213> ORGANISM: Homo sapiens

<400> SEQUENCE: 74

Arg Ala Ser Gln Gly Ile Ser Ser Trp Leu Ala
1               5                   10

<210> SEQ ID NO 75
<211> LENGTH: 7
<212> TYPE: PRT
<213> ORGANISM: Homo sapiens

<400> SEQUENCE: 75

Ala Ala Ser Ser Leu Gln Ser
1               5
```

```
<210> SEQ ID NO 76
<211> LENGTH: 7
<212> TYPE: PRT
<213> ORGANISM: Homo sapiens

<400> SEQUENCE: 76

Ala Asn Ser Phe Pro Leu Thr
1               5

<210> SEQ ID NO 77
<211> LENGTH: 11
<212> TYPE: PRT
<213> ORGANISM: Homo sapiens

<400> SEQUENCE: 77

Arg Ala Ser Gln Ser Val Ser Ser Tyr Leu Ala
1               5                   10

<210> SEQ ID NO 78
<211> LENGTH: 7
<212> TYPE: PRT
<213> ORGANISM: Homo sapiens

<400> SEQUENCE: 78

Asp Ala Pro Asn Arg Ala Thr
1               5

<210> SEQ ID NO 79
<211> LENGTH: 7
<212> TYPE: PRT
<213> ORGANISM: Homo sapiens

<400> SEQUENCE: 79

Arg Ser Asn Trp Ser Leu Thr
1               5

<210> SEQ ID NO 80
<211> LENGTH: 11
<212> TYPE: PRT
<213> ORGANISM: Homo sapiens

<400> SEQUENCE: 80

Arg Ala Ser Gln Gly Ile Ser Ser Ala Leu Ala
1               5                   10

<210> SEQ ID NO 81
<211> LENGTH: 7
<212> TYPE: PRT
<213> ORGANISM: Homo sapiens

<400> SEQUENCE: 81

Asp Val Ser Ser Leu Glu Ser
1               5

<210> SEQ ID NO 82
<211> LENGTH: 7
<212> TYPE: PRT
<213> ORGANISM: Homo sapiens

<400> SEQUENCE: 82

Phe Asn Ser Tyr Pro Leu Thr
1               5

<210> SEQ ID NO 83
<211> LENGTH: 7
```

```
<212> TYPE: PRT
<213> ORGANISM: Homo sapiens

<400> SEQUENCE: 83

Asp Ala Ser Asn Arg Ala Thr
1               5

<210> SEQ ID NO 84
<211> LENGTH: 7
<212> TYPE: PRT
<213> ORGANISM: Homo sapiens

<400> SEQUENCE: 84

Arg Ser Ser Trp Ser Leu Thr
1               5

<210> SEQ ID NO 85
<211> LENGTH: 12
<212> TYPE: PRT
<213> ORGANISM: Homo sapiens

<400> SEQUENCE: 85

Arg Ala Ser Gln Ser Val Ser Ser Ser Tyr Leu Ala
1               5                   10

<210> SEQ ID NO 86
<211> LENGTH: 7
<212> TYPE: PRT
<213> ORGANISM: Homo sapiens

<400> SEQUENCE: 86

Gly Ala Ser Ser Arg Ala Thr
1               5

<210> SEQ ID NO 87
<211> LENGTH: 7
<212> TYPE: PRT
<213> ORGANISM: Homo sapiens

<400> SEQUENCE: 87

Gln Gln Tyr Gly Ser Ser Pro
1               5

<210> SEQ ID NO 88
<211> LENGTH: 11
<212> TYPE: PRT
<213> ORGANISM: Homo sapiens

<400> SEQUENCE: 88

Arg Ala Ser Gln Gly Ile Ser Ser Trp Leu Ala
1               5                   10

<210> SEQ ID NO 89
<211> LENGTH: 7
<212> TYPE: PRT
<213> ORGANISM: Homo sapiens

<400> SEQUENCE: 89

Ala Ala Ser Ser Leu Gln Ser
1               5

<210> SEQ ID NO 90
<211> LENGTH: 9
<212> TYPE: PRT
<213> ORGANISM: Homo sapiens
```

```
<400> SEQUENCE: 90

Gln Gln Tyr Asn Ser Tyr Pro Ile Thr
1               5

<210> SEQ ID NO 91
<211> LENGTH: 12
<212> TYPE: PRT
<213> ORGANISM: Homo sapiens

<400> SEQUENCE: 91

Arg Ala Ser Gln Ser Phe Ser Gly Ser Tyr Leu Ala
1               5                   10

<210> SEQ ID NO 92
<211> LENGTH: 7
<212> TYPE: PRT
<213> ORGANISM: Homo sapiens

<400> SEQUENCE: 92

Asp Thr Ser Ser Arg Ala Thr
1               5

<210> SEQ ID NO 93
<211> LENGTH: 7
<212> TYPE: PRT
<213> ORGANISM: Homo sapiens

<400> SEQUENCE: 93

Gln Gln Tyr Gly Thr Trp Thr
1               5

<210> SEQ ID NO 94
<211> LENGTH: 11
<212> TYPE: PRT
<213> ORGANISM: Homo sapiens

<400> SEQUENCE: 94

Arg Ala Ser Gln Ser Val Ser Ser Phe Leu Ala
1               5                   10

<210> SEQ ID NO 95
<211> LENGTH: 9
<212> TYPE: PRT
<213> ORGANISM: Homo sapiens

<400> SEQUENCE: 95

Gln Gln Arg Ser Asn Trp Pro Pro Thr
1               5

<210> SEQ ID NO 96
<211> LENGTH: 7
<212> TYPE: PRT
<213> ORGANISM: Homo sapiens

<400> SEQUENCE: 96

Asp Ala Ser Ser Leu Glu Ser
1               5

<210> SEQ ID NO 97
<211> LENGTH: 9
<212> TYPE: PRT
<213> ORGANISM: Homo sapiens

<400> SEQUENCE: 97

Gln Gln Phe Asn Ser Tyr Pro Leu Thr
```

<210> SEQ ID NO 98
<211> LENGTH: 6
<212> TYPE: PRT
<213> ORGANISM: Homo sapiens

<400> SEQUENCE: 98

Gln Gln Tyr Gly Ser Ser
1               5

<210> SEQ ID NO 99
<211> LENGTH: 9
<212> TYPE: PRT
<213> ORGANISM: Homo sapiens

<400> SEQUENCE: 99

Gln Gln Arg Ser Asn Trp Ser Leu Thr
1               5

<210> SEQ ID NO 100
<211> LENGTH: 38
<212> TYPE: PRT
<213> ORGANISM: Artificial Sequence
<220> FEATURE:
<223> OTHER INFORMATION: chemically synthesized

<400> SEQUENCE: 100

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala
        35

<210> SEQ ID NO 101
<211> LENGTH: 18
<212> TYPE: PRT
<213> ORGANISM: Artificial Sequence
<220> FEATURE:
<223> OTHER INFORMATION: chemically synthesized

<400> SEQUENCE: 101

Met Pro Leu Leu Leu Leu Leu Pro Leu Leu Trp Ala Gly Ala Leu Ala
1               5                   10                  15

Met Asp

<210> SEQ ID NO 102
<211> LENGTH: 321
<212> TYPE: DNA
<213> ORGANISM: Homo sapiens

<400> SEQUENCE: 102
gacatcgtga tgacccagtc tccatcttcc gtgtctgcat ctgtaggaga cagagtcacc        60
atcacttgtc gggcgagtca gggtattagc agctggttag cctggtatca gcataaacca      120
gggaaagccc ctaagctcct gatctatgct gcatccagtt tgcaaagtgg ggtcccatca      180
aggttcagcg gcagtggatc tgggacagat tcactctca ccatcagcag cctgcagcct       240
gaagattttg caacttacta ttgtcaacag gctaatagtt tcccgctcac tttcggcgga      300
gggaccaagg tggagatcaa a                                                321

<210> SEQ ID NO 103

```
<211> LENGTH: 107
<212> TYPE: PRT
<213> ORGANISM: Homo sapiens

<400> SEQUENCE: 103

Asp Ile Val Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 104
<211> LENGTH: 321
<212> TYPE: DNA
<213> ORGANISM: Homo sapiens

<400> SEQUENCE: 104
gacatccaga tgacccagtc tccatcctcc ctgtctgcat ctgtaggaga cagagtcacc      60
atcacttgcc gggcaagtca gggcattagc agtgctttag cctggtatca gcagaaacca    120
gggaaagctc ctaagctcct gatctatgat gtctccagtt tggaaagtgg ggtcccatca    180
aggttcagcg gcagtggatc tgggacagat ttcactctca ccatcagcag cctgcagcct    240
gaagattttg caacttatta ctgtcaacag tttaatagtt accctctcac tttcggcgga    300
gggaccaagg tggagatcaa a                                              321

<210> SEQ ID NO 105
<211> LENGTH: 107
<212> TYPE: PRT
<213> ORGANISM: Homo sapiens

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Val Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105
```

ANTI-IL-17F ANTIBODIES

RELATED APPLICATIONS

This application claims the benefit of U.S. Provisional Application No. 61/175,512, filed May 5, 2009, the contents of which are hereby incorporated by reference in their entirety.

INCORPORATION-BY-REFERENCE OF SEQUENCE LISTING

The contents of the text file named "419USSeqListST25.txt," which was created on Apr. 30, 2010 and is 47.3 KB in size, are hereby incorporated by reference in their entirety.

FIELD OF THE INVENTION

This invention relates generally to the generation of monoclonal antibodies, e.g., fully human monoclonal antibodies, that recognize IL-17F but do not recognize IL-17A, to monoclonal antibodies, e.g., fully human monoclonal antibodies, that recognize the heterodimeric IL-17A/IL-17F complex, and to methods of using the monoclonal antibodies as therapeutics.

BACKGROUND OF THE INVENTION

IL-17F (also known as ML-1) is a member of the IL-17 family of cytokines, which also includes the proteins IL-17A (also known as CTL-8, IL-17), IL-17B, IL-17C, IL-17D, IL-17E (also called IL-25). Both IL-17A and IL-17F are secreted as disulfide linked homodimers which signal through the receptors IL-17R, IL-17RC, or a multimeric receptor complex composed of the IL-17R and IL-17RC. Both are also co-expressed on the same T cell subsets (principally by the Th17 CD4$^+$ T cells). IL-17A and IL-17F also interact and form a heterodimeric IL-17A/IL-17F complex.

Elevated levels of IL-17F and the IL-17A/IL-17F complex have been associated with a variety of inflammatory disorders and autoimmune diseases. Accordingly, there exists a need for therapies that neutralize the biological activities of IL-17F.

SUMMARY OF THE INVENTION

The present invention provides monoclonal antibodies such as fully human monoclonal antibodies which specifically bind to IL-17F and/or the IL-17A/IL-17F heterodimeric complex, but do not specifically bind to IL-17A. IL-17F is typically expressed and biologically active as a homodimeric protein. Thus, use of the term "IL-17F" and equivalents thereof refers to the IL-17F homodimeric protein, except where otherwise indicated. The antibodies of the invention are capable of modulating, e.g., blocking, inhibiting, reducing, antagonizing, neutralizing or otherwise interfering with IL-17F-mediated pro-inflammatory cytokine and/or chemokine production.

Exemplary monoclonal antibodies of the invention include, for example, the 5E12 antibody, the 41B10 antibody, the 11C5 antibody, the 21B10 antibody, 1F1 antibody and 2E12 antibody. Alternatively, the monoclonal antibody is an antibody that binds to the same epitope as the 41B10 antibody, the 11C5 antibody, the 21B10 antibody, 1F1 antibody, 2E12 antibody, the 5D3 antibody, the 22F8 antibody, the 28B11 antibody, the 41A4 antibody and the 43G6 antibody. These antibodies are respectively referred to herein as "huIL17F" antibodies. huIL-17F antibodies include fully human monoclonal antibodies, as well as humanized monoclonal antibodies and chimeric antibodies.

Preferably, the fully human monoclonal antibody is selected from the 11C5 antibody, the 21B10 antibody, 1F1 antibody, 2E12 antibody, 5D3 antibody, 22F8 antibody, 28B11 antibody, 41A4 antibody and 43G6 antibody. These antibodies exhibit higher affinity for IL-17F and/or the IL-17A/IL-17F heterodimeric complex than other antibodies that bind IL-17F and/or the IL-17A/IL-17F heterodimeric complex, such as, for example, the 5E12 antibody and the 41B10 antibody. These antibodies are better inhibitors of at least one biological activity or function of IL-17F than other antibodies that bind IL-17F and/or the IL-17A/IL-17F heterodimeric complex, such as, for example, the 5E12 antibody and the 41B10 antibody. For example, the 11C5 antibody, the 21B10 antibody, 1F1 antibody, 2E12 antibody, 5D3 antibody, 22F8 antibody, 28B11 antibody, 41A4 antibody and 43G6 antibody inhibit a biological activity and/or function of IL-17F to a greater degree than the 5E12 antibody and/or the 41B10 antibody. In some embodiments, the 11C5 antibody, the 21B10 antibody, 1F1 antibody, 2E12 antibody, 5D3 antibody, 22F8 antibody, 28B11 antibody, 41A4 antibody and 43G6 antibody decrease production of a pro-inflammatory cytokine in the presence of these antibodies to a greater degree than the decrease of pro-inflammatory cytokine production in the presence of other antibodies that bind IL-17F and/or the IL-17A/IL-17F heterodimeric complex, such as, for example, the 5E12 antibody and/or the 41B10 antibody. For example, the level of pro-inflammatory cytokine (e.g., IL-6) production in the presence of the 11C5 antibody, the 21B10 antibody, 1F1 antibody, 2E12 antibody, 5D3 antibody, 22F8 antibody, 28B11 antibody, 41A4 antibody and 43G6 antibody is greater than or equal to 5%, 10%, 20%, 25%, 30%, 40%, 50%, 60%, 70%, 75%, 80%, 90%, 95%, 99%, or 100% lower than the level of pro-inflammatory cytokine production other antibodies that bind IL-17F and/or the IL-17A/IL-17F heterodimeric complex, such as, for example, the 5E12 antibody and/or the 41B10 antibody.

These antibodies show specificity for human IL-17F and/or the human IL-17A/IL-17F heterodimeric complex, and they have been shown to inhibit IL-17F-mediated cytokine production. These antibodies have distinct specificities. In some embodiments, the huIL-17F antibodies of the invention specifically bind IL-17F, but do not specifically bind IL-17A. Preferably, the huIL-17 antibodies of the invention also specifically bind the IL-17F homodimer, but do not specifically bind the IL-17A homodimer. In some embodiments, the huIL-17F antibodies of the invention specifically bind the IL-17A/IL-17F heterodimeric complex, but do not specifically bind IL-17A or the IL-17A homodimer. In some embodiments, the huIL-17F antibodies of the invention specifically bind IL-17F and the IL-17A/IL-17F heterodimeric complex, but do not specifically bind IL-17A or the IL-17A homodimer. For example, the antibodies 11C5, 21B10, 1F1, 2E12, 41B10, 5D3, 22F8, 28B11, 41A4 and 43G6 specifically bind IL-17F, and these antibodies do not bind IL-17A or the IL-17A homodimer. Preferably, the huIL-17F antibodies bind IL-17F and do not cross react with IL-17A or IL-17A homodimer. For example, 5E12, 11C5, 21B10, 1F1, 2E12, 41B10, 5D3, 22F8, 28B11, 41A4 and 43G6 bind IL-17F but do not cross react with IL-17A.

The fully human antibodies of the invention contain a heavy chain variable region having the amino acid sequence of SEQ ID NOS: 10, 14, 18, 22, 26, 30, 34, 38 and 42. The human antibodies of the invention contain a light chain variable region having the amino acid sequence of SEQ ID NOS: 12, 16, 20, 24, 28, 32, 36, 40 and 44. The heavy chain CDRs include a VH CDR1 region comprising an amino acid sequence at least 90%, 92%, 95%, 97% 98%, 99% or more identical to a sequence selected from the group consisting of SEQ ID NOS: 45, 48, 51, 56, 59, 64, 67 and 70; a VH CDR2 region comprising an amino acid sequence at least 90%, 92%, 95%, 97% 98%, 99% or more identical to a sequence selected from the group consisting of SEQ ID NOS: 46, 49, 52, 54, 57, 60, 62, 65, 68, 71 and 73; and a VH CDR3 region comprising an amino acid sequence at least 90%, 92%, 95%, 97% 98%, 99% or more identical to a sequence selected from the group consisting of SEQ ID NOS: 47, 50, 53, 55, 58, 61, 63, 66, 69 and 72. The three light chain CDRs include a VL CDR1 region comprising an amino acid sequence at least 90%, 92%, 95%, 97% 98%, 99% or more identical to a sequence selected from the group consisting of SEQ ID NOS: 74, 77, 80, 85, 88, 91 and 94; a VL CDR2 region comprising an amino acid sequence at least 90%, 92%, 95%, 97% 98%, 99% or more identical to a sequence selected from the group consisting of SEQ ID NOS: 75, 78, 81, 83, 86, 89, 92 and 96; and a VL CDR3 region comprising an amino acid sequence at least 90%, 92%, 95%, 97% 98%, 99% or more identical to a sequence selected from the group consisting of SEQ ID NOS: 76, 79, 82, 84, 87, 90, 93, 95, 97, 98 and 99.

Preferably, the heavy chain CDRs include a VH CDR1 region comprising an amino acid sequence at least 90%, 92%, 95%, 97% 98%, 99% or more identical to a sequence selected from the group consisting of SEQ ID NOS: 45, 48, 51, 64, 67 and 70; a VH CDR2 region comprising an amino acid sequence at least 90%, 92%, 95%, 97% 98%, 99% or more identical to a sequence selected from the group consisting of SEQ ID NOS: 46, 49, 52, 54, 62, 65, 68, 71 and 73; and a VH CDR3 region comprising an amino acid sequence at least 90%, 92%, 95%, 97% 98%, 99% or more identical to a sequence selected from the group consisting of SEQ ID NOS: 47, 50, 53, 55, 63, 66, 69 and 72. The three light chain CDRs include a VL CDR1 region comprising an amino acid sequence at least 90%, 92%, 95%, 97% 98%, 99% or more identical to a sequence selected from the group consisting of SEQ ID NOS: 74, 77, 80, 85, 91 and 94; a VL CDR2 region comprising an amino acid sequence at least 90%, 92%, 95%, 97% 98%, 99% or more identical to a sequence selected from the group consisting of SEQ ID NOS: 75, 78, 81, 83, 86, 92 and 96; and a VL CDR3 region comprising an amino acid sequence at least 90%, 92%, 95%, 97% 98%, 99% or more identical to a sequence selected from the group consisting of SEQ ID NOS: 76, 79, 82, 84, 93, 95, 97, 98 and 99, provided that when the VL CDR1 comprises an amino acid sequence that is at least 90%, 92%, 95%, 97% 98%, 99% or more identical to the sequence of SEQ ID NO:85, the VL CDR2 comprises an amino acid sequence that is at least 90%, 92%, 95%, 97% 98%, 99% or more identical to the sequence of SEQ ID NO: 86 and the VL CDR3 comprises an amino acid sequence that is at least 90%, 92%, 95%, 97% 98%, 99% or more identical to the sequence of SEQ ID NO:98, and provided that when the VL CDR2 comprises an amino acid sequence that is at least 90%, 92%, 95%, 97% 98%, 99% or more identical to the sequence of SEQ ID NO:86, the VL CDR1 comprises an amino acid sequence that is at least 90%, 92%, 95%, 97% 98%, 99% or more identical to the sequence of SEQ ID NO: 85 and the VL CDR3 comprises an amino acid sequence that is at least 90%, 92%, 95%, 97% 98%, 99% or more identical to the sequence of SEQ ID NO:98.

Antibodies of the invention immunospecifically bind IL-17F wherein the antibody binds to an epitope that includes one or more amino acid residues on human IL-17F. In some embodiments, antibodies of the invention also specifically bind the heterodimeric IL-17A/IL-17F complex but not IL-17A, wherein the antibody binds to an epitope that includes one or more amino acid residues on human IL-17F.

Antibodies of the invention also include fully human antibodies that specifically bind IL-17F and/or the heterodimeric IL-17A/IL-17F complex wherein the antibody exhibits greater than 50% inhibition of IL-17F-mediated pro-inflammatory cytokine production in vitro. For example, antibodies of the invention exhibit greater than 55%, 60%, 65%, 70%, 75%, 80%, 85%, 90%, 92%, 95%, 97%, 98%, or 99% inhibition of IL-6 secretion by IL-17 stimulated cells. As used herein, the term "pro-inflammatory cytokine" refers to those immunoregulatory cytokines that promote inflammation and/or are associated with inflammation. Pro-inflammatory cytokines and chemokines include, for example, IL-6, IL-8, G-CSF, and GM-CSF. Pro-inflammatory chemokines include, for example, GRO-α, GRO-b, LIX, GCP-2, MIG, IP10, I-TAC, and MCP-1, RANTES, Eotaxin, SDF-1, and MIP3a.

The present invention also provides methods of treating or preventing pathologies associated with aberrant IL-17F activity (e.g., aberrant pro-inflammatory cytokine production, such as for example aberrant IL-6 production), or alleviating a symptom associated with such pathologies, by administering a monoclonal antibody of the invention (e.g., fully human monoclonal antibody) to a subject in which such treatment or prevention is Desired . The subject to be treated is, e.g., human. The monoclonal antibody is administered in an amount sufficient to treat, prevent or alleviate a symptom associated with the pathology. The amount of monoclonal antibody sufficient to treat or prevent the pathology in the subject is, for example, an amount that is sufficient to reduce IL-17F signaling (e.g., IL-17F-induced production of one or more pro-inflammatory cytokines such as e.g., IL-6). As used herein, the term "reduced" refers to a decreased production of a pro-inflammatory cytokine in the presence of a monoclonal antibody of the invention, wherein the production is, for example, local pro-inflammatory cytokine production (e.g., at a site of inflamed tissue) or systemic pro-inflammatory cytokine production. IL-17F signaling (e.g., IL-17F-induced pro-inflammatory cytokine such as IL-6) is decreased when the level of pro-inflammatory cytokine (e.g., IL-6) production in the presence of a monoclonal antibody of the invention is greater than or equal to 5%, 10%, 20%, 25%, 30%, 40%, 50%, 60%, 70%, 75%, 80%, 90%, 95%, 99%, or 100% lower than a control level of pro-inflammatory cytokine production (i.e., the level of pro-inflammatory cytokine production in the absence of the monoclonal antibody). Level of pro-inflammatory cytokine production (e.g., IL-6) is measured, e.g., using the IL-17F-stimulated Mouse Embryonic Fibroblasts (MEF) cellular assays described herein. Those skilled in the art will appreciate that the level of pro-inflammatory cytokine production can be measured using a variety of assays, including, for example, commercially available ELISA kits.

Pathologies treated and/or prevented using the monoclonal antibodies of the invention (e.g., fully human monoclonal antibody) include, for example, acute inflammation, chronic inflammation (e.g., chronic inflammation associated with allergic conditions and asthma, chronic inflammation associated with arthritic conditions), autoimmune diseases (e.g., Crohn's disease, multiple sclerosis, rheumatoid arthritis and other autoimmune arthritic conditions), inflammatory bowel disease, and transplant rejection.

Pharmaceutical compositions according to the invention can include an antibody of the invention and a carrier. These pharmaceutical compositions can be included in kits, such as, for example, diagnostic kits.

The present invention also provides soluble IL-17F proteins, methods for expressing IL-17F proteins, and methods for purifying such proteins in a soluble form.

In some embodiments, the pathology to be treated is one or more autoimmune diseases, inflammatory disorders or cancers. For example, without limitation, the pathology is rheumatoid arthritis and other arthritic conditions, Crohn's disease, psoriasis, multiple sclerosis chronic obstructive pulmonary disease and/or asthma, cancer and angiogenesis.

Pharmaceutical compositions according to the invention can include an antibody of the invention and a carrier. These pharmaceutical compositions can be included in kits, such as, for example, diagnostic kits.

One skilled in the art will appreciate that the antibodies of the invention have a variety of uses. For example, the proteins of the invention are used as therapeutic agents to prevent the activation of IL-17F receptor in disorders such as, for example, rheumatoid arthritis, Crohn's disease, psoriasis, multiple sclerosis chronic obstructive pulmonary disease, angiogenesis, asthma and cancer. The antibodies of the invention are also used as reagents in diagnostic kits or as diagnostic tools, or these antibodies can be used in competition assays to generate therapeutic reagents.

BRIEF DESCRIPTION OF THE DRAWINGS

FIG. 2A depicts the detected serum level of tumor necrosis factor alpha (TNF-α); FIG. 2B depicts the detected serum level of interleukin 6 (IL-6); FIG. 2C depicts the detected serum level of interferon gamma (IFN-γ); FIG. 2D depicts the detected serum level of interleukin 1 alpha (IL-1α); FIG. 2E depicts the detected serum level of monocyte chemotactic protein (MCP-1); and FIG. 2F depicts the detected serum level of the interleukin 12/interleukin 23 (IL-12/IL-23) heterodimeric complex.

DETAILED DESCRIPTION

Figure 1:
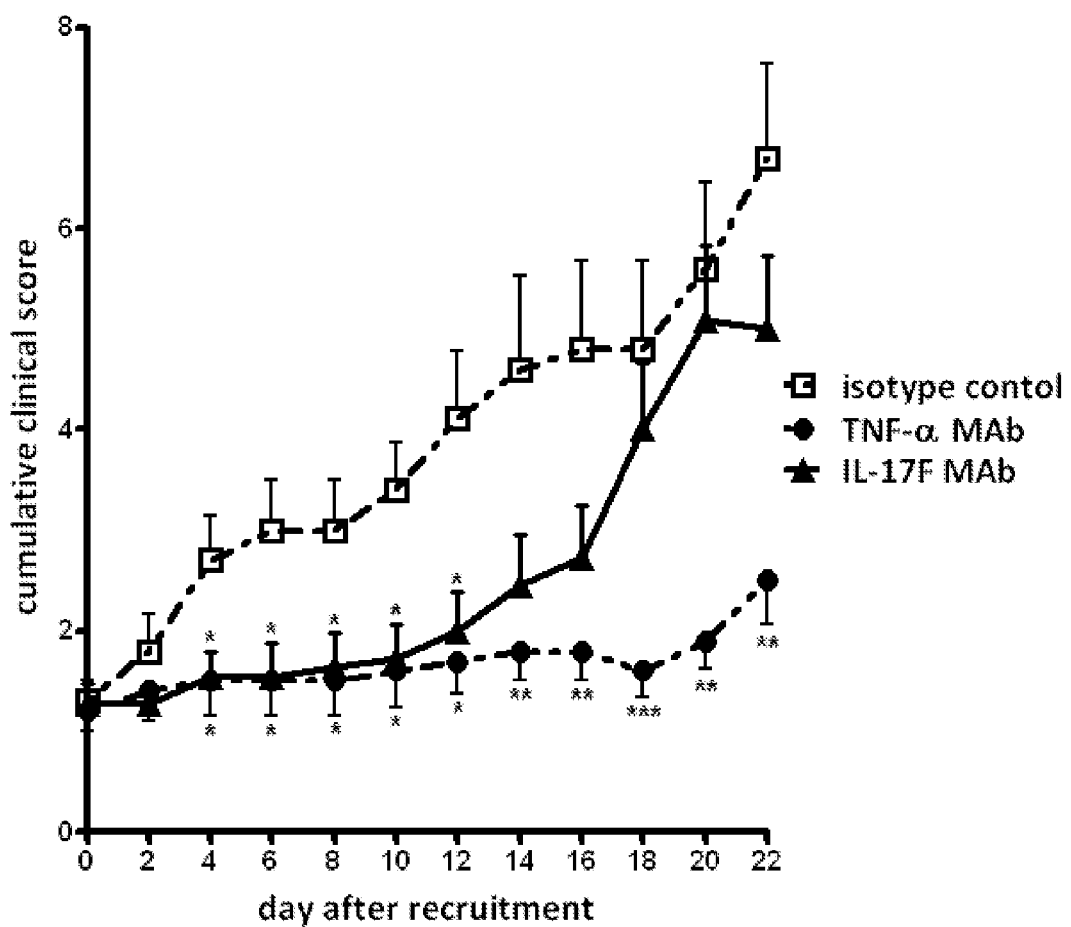
FIG. 1 is a graph that depicts the progression of clinical scoring of collagen-induced arthritis in mice using standard arthritis scoring methods.

The present invention provides monoclonal antibodies that specifically bind IL-17F. The invention further provides monoclonal antibodies that specifically bind IL-17F and the heterodimeric IL-17A/IL-17F complex (also referred to herein as the IL-17A/IL-17F heterodimer). The antibody is e.g., a fully human monoclonal antibody.

Antibodies of the invention specifically bind IL-17F but not IL-17A, wherein the antibody binds to an epitope that includes one or more amino acid residues of human IL-17F. In some embodiments, antibodies of the invention specifically bind IL-17F and the heterodimeric IL-17A/IL-17F complex but not IL-17A or the IL-17A homodimer, wherein the antibody binds to an epitope that includes one or more amino acid residues of human IL-17F.

The antibodies of the present invention bind to an IL-17F epitope with an equilibrium binding constant ($K_d$) of $\leq 1$ μM, e.g., $\leq 100$ nM, preferably $\leq 10$ nM, and more preferably $\leq 1$ nM. For example, the huIL-17F antibodies provided herein exhibit a $K_d$ in the range approximately between $\leq 1$ nM to about 1 pM.

The crystal structure of IL-17F reveals that the protein adopts a cysteine knot fold, suggesting a relationship to the cysteine knot superfamily of proteins. However, the cysteine knot motif of IL-17F only utilizes four cysteines instead of the classical six cysteines to form the knot. Like other members of the cysteine knot family, IL-17F also exists as a heterodimer with IL-17A. The IL-17A/IL-17F heterodimer is believed to signal through IL-17R and/or the multimeric IL-17R/IL-17RC complex. Recent evidence has shown that the same cysteine residues that are utilized in forming the IL-17A/IL-17F heterodimer are the same cysteines utilized in the IL-17F homodimer formation. This data suggests that the receptor for the IL-17F homodimer or IL-17A/IL-17F heterodimer may bind to the conserved cysteine residues at the dimer interface, like other proteins in the cysteine knot family.

Numerous immune regulatory functions have been reported for the IL-17 family of cytokines, presumably due to their induction of many immune signaling molecules. IL-17A, expressed as the IL-17A homodimer, and IL-17F, expressed as the IL-17F homodimer, share very similar biological functions in some cases. Both promote secretion of pro-inflammatory cytokines (e.g., IL-6, IL-8, G-CSF, and GM-CSF), chemokines (e.g., GRO-α, GRO-b, LIX, GCP-2, MIG, IP10, I-TAC, and MCP-1, RANTES, Eotaxin, SDF-1, and MIP3a) and prostaglandins (e.g., $PGE_2$) from a wide variety of cells including fibroblasts, keratinocytes, macrophages, epithelial cells and endothelial cells. Both have also been shown to regulate cartilage matrix turnover. IL-17F homodimer also have biological functions distinct from IL-17A homodimer such as the ability to stimulate proliferation and activation of T cells and peripheral blood mononuclear cells (PBMCs), and to inhibit angiogenesis.

The huIL17F antibodies of the invention serve to modulate, block, inhibit, reduce, antagonize, neutralize or otherwise interfere with the biological activity of IL-17F. Biological activities of IL-17F include, for example, binding to IL-17R, IL-17RC and/or the multimeric IL-17R/IL-17RC receptor complex, and the induction of cytokine and/or chemokine expression (e.g., IL-6, IL-8, G-CSF, GM-CSF, GRO-α, GRO-b, LIX, GCP-2, MIG, IP10, I-TAC, and MCP-1, RANTES, Eotaxin, SDF-1, and MIP3a) in target cells. For example, the huIL-17F antibodies completely or partially inhibit IL-17F biological activity by partially or completely modulating, blocking, inhibiting, reducing antagonizing, neutralizing, or otherwise interfering with the binding of IL-17F to its receptor, or otherwise partially or completely modulating, blocking, inhibiting, reducing, antagonizing, neutralizing IL-17F signaling activity.

The huIL-17F antibodies are considered to completely modulate, block, inhibit, reduce, antagonize, neutralize or otherwise interfere with IL-17F biological activity when the level of IL-17F activity in the presence of the huIL-17F antibody is decreased by at least 95%, e.g., by 96%, 97%, 98%, 99% or 100% as compared to the level of IL-17F activity in the absence of binding with an huIL-17F antibody described herein. The huIL-17F antibodies are considered to partially modulate, block, inhibit, reduce, antagonize, neutralize or otherwise interfere with IL-17F activity when the level of IL-17F activity in the presence of the huIL-17F antibody is decreased by less than 95%, e.g., 10%, 20%, 25%, 30%, 40%, 50%, 60%, 75%, 80%, 85% or 90% as compared to the level of IL-17F activity in the absence of binding with an huIL-17F antibody described herein.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the terms Interleukin-17A, IL-17A, IL17A, IL-17, IL17, CTLA8, CTLA-8, Cytotoxic T-lymphocyte-associated antigen 8 and Interleukin-17A precursor are synonymous and may be used interchangeably. Each of these terms refers to the homodimeric protein, except where otherwise indicated.

As used herein, the terms Interleukin-17F, IL-17F, IL17F, ML-1, ML1, Interleukin-24, IL-24, IL24 and Interleukin-17F precursor are synonymous and may be used interchangeably. Each of these terms refers to the IL-17F homodimeric protein, except where otherwise indicated.

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "directed against" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, dAb (domain antibody), single chain, $F_{ab}$, $F_{ab'}$ and $F_{(ab')2}$ fragments, scFvs, and an $F_{ab}$ expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin or fragment thereof, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is $\leq 1$ μM; e.g., $\leq 100$ nM, preferably $\leq 10$ nM and more preferably $\leq 1$ nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to IL-17F and/or the IL-17A/IL-17F heterodimer, when the equilibrium binding constant ($K_d$) is $\leq 1$ μM, preferably $\leq 100$ nM, more preferably $\leq 10$ nM, and most preferably $\leq 100$ pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the invention include the nucleic acid molecules encoding the heavy chain immunoglobulin molecules presented in SEQ ID NOS: 1, 5, 9, 13, 17, 21, 25, 29, 33, 37 and 41, and nucleic acid molecules encoding the light chain immunoglobulin molecules represented in SEQ ID NOS: 3, 7, 11, 15, 19, 23, 27, 31, 35, 39 and 43.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of marine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecules represented in SEQ ID NOS: 2, 6, 10, 14, 18, 22, 26, 30, 34, 38 and 42, and the light chain immunoglobulin molecules represented in SEQ ID NOS: 4, 8, 12, 16, 20, 24, 28, 32, 36, 40 and 44, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means a polymeric boron of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the invention are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes Oligonucleotides linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman Adv. Appl. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Gren, Eds., Sinauer Associates, Sunderland7 Mass. (1991)). Stereoisomers D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion, but where the remaining amino acid sequence is identical to the corresponding positions in the naturally-occurring sequence deduced, for example, from a full length cDNA sequence. Fragments typically are at least 5, 6, 8 or 10 amino acids long, preferably at least 14 amino acids long' more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has specific binding to IL-17F alone or IL-17A/IL-17F heterodimer (i.e., complex), under suitable binding conditions. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986), Veber and Freidinger TINS p. 392 (1985); and Evans et al. J. Med. Chem. 30:1229 (1987). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —CH₂NH—, —CH₂S—, —CH₂—CH₂—, —CH=CH-(cis and trans), —COCH₂—, CH(OH)CH₂—, and —CH₂SO—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992)); for example, by adding internal cysteine residues capable of forming intramolecular disulfide bridges which cyclize the peptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$) fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

Autoimmune diseases include, for example, Acquired Immunodeficiency Syndrome (AIDS, which is a viral disease with an autoimmune component), alopecia greata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barré syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjögren's syndrome, stiffman syndrome, systemic lupus erythematosus, Takayasu arteritis, temporal arteritis/giant cell arteritis, ulcerative colitis, uveitis, vitiligo and Wegener's granulomatosis.

Inflammatory disorders include, for example, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

huIL-17F Antibodies

Monoclonal antibodies of the invention (e.g., fully human monoclonal antibodies) bind IL-17F, and in some embodiments, the IL-17A/IL-17F heterodimeric complex, but do not bind IL-17A or the IL-17A homodimer. These monoclonal antibodies have the ability to inhibit IL-17F-induced proinflammatory cytokine production (e.g., IL-6). Inhibition is determined, for example, the IL-17F stimulated mouse embryonic fibroblast (MEF) cellular assays described herein.

Exemplary antibodies of the invention include, for example, the 5E12 antibody, the 41B10 antibody, the 11C5 antibody, the 21B10 antibody, the 1F1 antibody, the 2E12 antibody, the 5D3 antibody, the 22F8 antibody, the 28B11 antibody, the 41A4 antibody and the 43G6 antibody described herein. These antibodies show specificity for human IL-17F and/or the heterodimeric IL-17A/IL-17F complex, and they have been shown to inhibit human IL-17F induction of the pro-inflammatory cytokine IL-6 in vitro.

Each of the huIL-17F monoclonal antibodies described herein includes a heavy chain variable region (VH) and a light chain variable region (VL), as shown in the amino acid and corresponding nucleic acid sequences listed below.

The 5E12 antibody includes a heavy chain variable region (SEQ ID NO:2) encoded by the nucleic acid sequence shown in SEQ ID NO:1, and a light chain variable region (SEQ ID NO:4) encoded by the nucleic acid sequence shown in SEQ ID NO:3.

>5E12 VH nucleic acid sequence
(SEQ ID NO: 1)
CAGGTGCAGCTGGTGCAGTCTGGGGGAGGCTTGGTACAGCCTGGCAGGTCCCTGAGACTCTC

CTGTGCAGCCTCTGGATTCACCTTTGATGATTATGCCATGCACTGGGTCCGGCAAGCTCCAG

GGAAGGGCCTGGAGTGGGTCTCAGGTATTAGTTGGAATAGTGGTACCATAGGCTATGCGGAC

TCTGTGAAGGGCCGATTCACCATCTCCAGAGACAACGCCAAGAACTCCCTGTATCTGCAAAT

GAACAGTCTGAGAGCTGAGGACACGGCCTTGTATTACTGTGCAAAAGAACTGTATATCAGTG

ACTGGGACTCCTACTCCTACGGTATGGACGTCTGGGGCCAAGGGACCACGGTCACCGTCTCC

TCA

>5E12 VH amino acid sequence
(SEQ ID NO: 2)
QVQLVQSGGGLVQPGRSLRLSCAASGFTFDDYAMHWVRQAPGKGLEWVSGISWNSGTIGYAD

SVKGRFTISRDNAKNSLYLQMNSLRAEDTALYYCAKELYISDWDSYSYGMDVWGQGTTVTVSS

>5E12 VL nucleic acid sequence
(SEQ ID NO: 3)
GAAATTGTGTTGACGCAGTCTCCAGGCACCCTGTCTTTGTCTCCAGGGGAAAGAGCCACCCT

CTCCTGCAGGGCCAGTCAGAGTGTTAGCAGCAGCTACTTAGCCTGGTACCAGCAGAAACCTG

GCCAGGCTCCCAGGCTCCTCATCTATGGTGCATCCAGCAGGGCCACTGGCATCCCAGACAGG

TTCAGTGGCAGTGGGTCTGGGACAGACTTCACTCTCACCATCAGCAGACTGGAGCCTGAAGA

TTTTGCAGTGTATTACTGTCAGCAGTATGGTAGCTCACCTTTCGGCGGAGGGACCAAGGTGG

AGATCAAA

>5E12 VL amino acid sequence
(SEQ ID NO: 4)
EIVLTQSPGTLSLSPGERATLSCRASQSVSSSYLAWYQQKPGQAPRLLIYGASSRATGIPDR

FSGSGSGTDFTLTISRLEPEDFAVYYCQQYGSSPFGGGTKVEIK

The 41B10 antibody includes a heavy chain variable region (SEQ ID NO:6) encoded by the nucleic acid sequence shown in SEQ ID NO:5, and a light chain variable region (SEQ ID NO:8) encoded by the nucleic acid sequence shown in SEQ ID NO:7.

>41B10 VH nucleic acid sequence
(SEQ ID NO: 5)
GAGGTGCAGCTGGTGGAGTCTGGGGGAGGCTTGGTAAAGCCTGGGGGGTCCCTTAGACTCTC

CTGTGCAGCCTCTGGATTCACTTTCAGTAACGCCTGGATGAGCTGGGTCCGCCAGGCTCCAG

GGAAGGGGCTGGAATGGGTTGGCCGTATTAAAAGCAAAACTGATGGTGGGACAACAGACTAC

GTTGCACCCGTGAAAGGCAGATTCACCATCTCAAGAGATGATTCAAAAAACACCCTGTATCT

GCAAATGAACAGCCTGAAAACCGAGGACACAGCCGTATATTACTGTACCACATCGTATAGCA

GTTACTGGTTCCCCTACTACTTTGACTACTGGGGCCAGGGAACCCTGGTCACCGTCTCCTCA

>41B10 VH amino acid sequence
(SEQ ID NO: 6)
EVQLVESGGGLVKPGGSLRLSCAASGFTFSNAWMSWVRQAPGKGLEWVGRIKSKTDGGTTDY

VAPVKGRFTISRDDSKNTLYLQMNSLKTEDTAVYYCTTSYSSYWFPYYFDYWGQGTLVTVSS

>41B10 VL nucleic acid sequence
(SEQ ID NO: 7)
GACATCCAGATGACCCAGTCTCCATCCTCACTGTCTGCATCTGTAGGAGACAGAGTCACCAT

CACTTGTCGGGCGAGTCAGGGTATTAGCAGCTGGTTAGCCTGGTATCAGCAGAAACCAGAGA

AAGCCCCTAAGTCCCTGATCTATGCTGCATCCAGTTTGCAAAGTGGGGTCCCATCAAGGTTC

AGCGGCAGTGGATCTGGGACAGATTTCACTCTCACCATCAGCAGCCTGCAGCCTGAAGATTT

```
-continued
TGCAACTTATTACTGCCAACAGTATAATAGTTACCCGATCACCTTCGGCCAAGGGACACGAC

TGGAGATTAAA

>41B10 VL amino acid sequence
                                                      (SEQ ID NO: 8)
DIQMTQSPSSLSASVGDRVTITCRASQGISSWLAWYQQKPEKAPKSLIYAASSLQSGVPSRF

SGSGSGTDFTLTISSLQPEDFATYYCQQYNSYPITFGQGTRLEIK
```

The 11C5 antibody includes a heavy chain variable region (SEQ ID NO:10) encoded by the nucleic acid sequence shown in SEQ ID NO:9, and a light chain variable region (SEQ ID NO:12) encoded by the nucleic acid sequence shown in SEQ ID NO:11. The amino acid sequence of the light chain variable region for the 11C5 antibody include mutations at the 5' end to convert the residues to the residues found in the corresponding human germline sequence. The non-mutated version of the light chain variable region amino acid sequence for the 11C5 antibody is shown in SEQ ID NO: 103, and the non-mutated version of the light chain variable region nucleic acid sequence for the 11C5 antibody is shown in SEQ ID NO: 102.

```
>11C5 VH Nucleic acid sequence
                                                      (SEQ ID NO: 9)
CAGGTGCAGCTGGTGCAGTCTGGGGCTGAGGTGAAGAAGCCTGGGGCCTCAGTGAAGGTT

TCCTGCAAGGCATCTGGATACACCTTCACCATCTATTATTTGCACTGGGTGCGACAGGCC

CCTGGACAAGGGCTTGAGTGGATGGGAATAATCAACCCTAGTGGTGGTAGGACAAACTAC

GCACAGAAGTTCCAGGGCAGGGTCACCATGACCAGGGACCCGTCCACGAACACAGTCTAC

ATGGAACTGAGCAGCCTGACATCTGAGGACGCGGCCGTGTATTACTGTGCGAGAGGGGAA

TTTAGCAGTGGCTGGCTTGACTACTGGGGCCAAGGGACCACGGTCACCGTCTCCTCA

>11C5 VH Amino acid sequence
                                                     (SEQ ID NO: 10)
QVQLVQSGAEVKKPGASVKVSCKASGYTFTIYYLHWVRQAPGQGLEWMGIINPSGGRTNY

AQKFQGRVTMTRDPSTNTVYMELSSLTSEDAAVYYCARGEFSSGWLDYWGQGTTVTVSS

>11C5 VL Nucleic acid sequence
                                                     (SEQ ID NO: 11)
GACATCCAGATGACCCAGTCTCCATCTTCCGTGTCTGCATCTGTAGGAGACAGAGTCACC

ATCACTTGTCGGGCGAGTCAGGGTATTAGCAGCTGGTTAGCCTGGTATCAGCATAAACCA

GGGAAAGCCCCTAAGCTCCTGATCTATGCTGCATCCAGTTTGCAAAGTGGGGTCCCATCA

AGGTTCAGCGGCAGTGGATCTGGGACAGATTTCACTCTCACCATCAGCAGCCTGCAGCCT

GAAGATTTTGCAACTTACTATTGTCAACAGGCTAATAGTTTCCCGCTCACTTTCGGCGGA

GGGACCAAGGTGGAGATCAAA

>11C5 VL Amino acid sequence
                                                     (SEQ ID NO: 12)
DIQMTQPSSVSASVGDRVTITCRASQGISSWLAWYQHKPGKAPKLLIYAASSLQSGVPS

RFSGSGSGTDFTLTISSLQPEDFATYYCQQANSFPLTFGGGTKVEIK

>Non-mutated 11C5 VL Nucleic acid sequence
                                                    (SEQ ID NO: 102)
GACATCGTGATGACCCAGTCTCCATCTTCCGTGTCTGCATCTGTAGGAGACAGAGTCACC

ATCACTTGTCGGGCGAGTCAGGGTATTAGCAGCTGGTTAGCCTGGTATCAGCATAAACCA

GGGAAAGCCCCTAAGCTCCTGATCTATGCTGCATCCAGTTTGCAAAGTGGGGTCCCATCA

AGGTTCAGCGGCAGTGGATCTGGGACAGATTTCACTCTCACCATCAGCAGCCTGCAGCCT

GAAGATTTTGCAACTTACTATTGTCAACAGGCTAATAGTTTCCCGCTCACTTTCGGCGGA

GGGACCAAGGTGGAGATCAAA

>Non-mutated 11C5 VL Amino acid sequence
                                                    (SEQ ID NO: 103)
DIVMTQSPSSVSASVGDRVTITCRASQGISSWLAWYQHKPGKAPKLLIYAASSLQSGVPS

RFSGSGSGTDFTLTISSLQPEDFATYYCQQANSFPLTFGGGTKVEIK
```

The 21B10 antibody includes a heavy chain variable region (SEQ ID NO:14) encoded by the nucleic acid sequence shown in SEQ ID NO:13, and a light chain variable region (SEQ ID NO:16) encoded by the nucleic acid sequence shown in SEQ ID NO:15.

```
>21B10 VH Nucleic acid sequence
                                             (SEQ ID NO: 13)
GAGGTGCAGCTGGTGGAGTCTGGGGGAGGCTTGGTACAGCCTGGGGGGTCCCTGAGACTC

TCCTGTGCAGCCTCTGGATTCACCTTCAGTAGCTATAGCATGAACTGGGTCCGCCAGGCT

CCAGGGAAGGGGCTGGAGTGGGTTTCATACATTAGTGGTGGTAGTAGTACCATATACTAC

GCAGACTCTGTGAAGGGCCGATTCACCATCTCCAGAGACAATGCCAAGAACTCACTGTAT

CTGCAAATGAACAGCCTGAGAGACGAGGACACGGCTGTGTATTACTGTGCGAGAGAGGGC

TATGTTTCGGGGACCTATTACAACTACTACTACGGTATGGACGTCTGGGGCCAAGGGACC

ACGGTCACCGTCTCCTCA

>21B10 VH Amino acid sequence
                                             (SEQ ID NO: 14)
EVQLVESGGGLVQPGGSLRLSCAASGFTFSSYSMNWVRQAPGKGLEWVSYISGGSSTIYY

ADSVKGRFTISRDNAKNSLYLQMNSLRDEDTAVYYCAREGYVSGTYYNYYYGMDVWGQGT

TVTVSS

>21B10 VL Nucleic acid sequence
                                             (SEQ ID NO: 15)
GAAATTGTGTTGACCCAGTCTCCAGCCACCCTGTCTTTGTCTCCAGGGGAAAGAGCCACC

CTCTCCTGCAGGGCCAGTCAGAGTGTTAGCAGTTACTTAGCCTGGTACCAACAGAAACCT

GGCCAGGCTCCCAGGCTCCTCATCTATGATGCACCCAACAGGGCCACTGGCATCCCAGCC

AGGTTCAGTGGCAGTGGGTCTGGGACAGACTTCACTCTCACCATCAGCAGCCTAGAGCCT

GAAGATTTTGCAGTTTATTACTGTCAGCAGCGTAGCAACTGGTCGCTCACTTTCGGCGGA

GGGACCAAGGTGGAGATCAAA

>21B10 VL amino acid sequence
                                             (SEQ ID NO: 16)
EIVLTQSPATLSLSPGERATLSCRASQSVSSYLAWYQQKPGQAPRLLIYDAPNRATGIPA

RFSGSGSGTDFTLTISSLEPEDFAVYYCQQRSNWSLTFGGGTKVEIK
```

The 1F1 antibody includes a heavy chain variable region (SEQ ID NO:18) encoded by the nucleic acid sequence shown in SEQ ID NO:17, and a light chain variable region (SEQ ID NO 20) encoded by the nucleic acid sequence shown in SEQ ID NO:19. The amino acid sequence of the light chain variable region for the 1F1 antibody include mutations at the 5' end to convert the residues to the residues found in the corresponding human germline sequence. The non-mutated version of the light chain variable region amino acid sequence for the 1F1 antibody is shown in SEQ ID NO: 104, and the non-mutated version of the light chain variable region nucleic acid sequence for the 1F1 antibody is shown in SEQ ID NO: 105.

```
>1F1 VH Nucleic acid sequence
                                             (SEQ ID NO: 17)
GAGGTGCAGCTGTTGGAGTCTGGGGGAGGCTTGGTACAGCCTGGGGGGTCCCTGAGACTC

TCCTGTGCAGCCTCTGGATTCACCTTTAGCAGCTATGTCATGAGCTGGGTCCGCCAGGTT

CCAGGGAAGGGGCTGGAGTGGGTCTCAGCTATTAGTGGTCGTGGTGGTAACACATTCTAC

GCAGACTCCGTGAAGGGCCGGTTCACCATCTCCAGAGACAATTCCAAGAACACGCTGTAT

CTGCAAATGGACAGCCTGAGAGCCGAGGACACGGCCGTATATTACTGTGCGAAAGATGAT

CGGCGTATAGCAGCAGGTAGTTTTGACTATTGGGGCCAAGGGACCACGGTCACCGTCTCC

TCA
```

```
>1F1 VH Amino acid sequence
                                             (SEQ ID NO: 18)
EVQLLESGGGLVQPGGSLRLSCAASGFTFSSYVMSWVRQVPGKGLEWVSAISGRGGNTFY

ADSVKGRFTISRDNSKNTLYLQMDSLRAEDTAVYYCAKDDRRIAAGSFDYWGQGTTVTVSS

>1F1 VL Nucleic acid sequence
                                             (SEQ ID NO: 19)
GCCATCCAGTTGACCCAGTCTCCATCCTCCCTGTCTGCATCTGTAGGAGACAGAGTCACC

ATCACTTGCCGGGCAAGTCAGGGCATTAGCAGTGCTTTAGCCTGGTATCAGCAGAAACCA

GGGAAAGCTCCTAAGCTCCTGATCTATGATGTCTCCAGTTTGGAAAGTGGGGTCCCATCA

AGGTTCAGCGGCAGTGGATCTGGGACAGATTTCACTCTCACCATCAGCAGCCTGCAGCCT

GAAGATTTTGCAACTTATTACTGTCAACAGTTTAATAGTTACCCTCTCACTTTCGGCGGA

GGGACCAAGGTGGAGATCAAA

>1F1 VL Amino acid sequence
                                             (SEQ ID NO: 20)
AIQLTQSPSSLSASVGDRVTITCRASQGISSALAWYQQKPGKAPKLLIYDVSSLESGVPS

RFSGSGSGTDFTLTISSLQPEDFATYYCQQFNSYPLTFGGGTKVEIK

>Non-mutated 1F1 VL Nucleic acid sequence
                                             (SEQ ID NO: 104)
GACATCCAGATGACCCAGTCTCCATCCTCCCTGTCTGCATCTGTAGGAGACAGAGTCACC

ATCACTTGCCGGGCAAGTCAGGGCATTAGCAGTGCTTTAGCCTGGTATCAGCAGAAACCA

GGGAAAGCTCCTAAGCTCCTGATCTATGATGTCTCCAGTTTGGAAAGTGGGGTCCCATCA

AGGTTCAGCGGCAGTGGATCTGGGACAGATTTCACTCTCACCATCAGCAGCCTGCAGCCT

GAAGATTTTGCAACTTATTACTGTCAACAGTTTAATAGTTACCCTCTCACTTTCGGCGGA

GGGACCAAGGTGGAGATCAAA

>Non-mutated 1F1 VL Amino acid sequence
                                             (SEQ ID NO: 105)
DIQMTQSPSSLSASVGDRVTITCRASQGISSALAWYQQKPGKAPKLLIYDVSSLESGVPS

RFSGSGSGTDFTLTISSLQPEDFATYYCQQFNSYPLTFGGGTKVEIK
```

The 2E12 antibody includes a heavy chain variable region (SEQ ID NO:22) encoded by the nucleic acid sequence shown in SEQ ID NO:21, and a light chain variable region (SEQ ID NO 24) encoded by the nucleic acid sequence shown in SEQ ID NO:23.

```
>2E12 VH Nucleic acid sequence
                                             (SEQ ID NO: 21)
GAGGTGCAGCTGGTGGAGTCTGGGGGAGGCTTGGTACAGCGGGGGGGTCCCTGAGACTC

TCCTGTGCAGCCTCTGGATTCACCTTCAGTAGCTATAGCATGAACTGGGTCCGCCAGGCT

CCAGGGAAGGGGCTGGAGTGGATTTCATACATTAGTAGTAGTAGTAGTGCCATATACTAC

GCAGACTCTGTGAAGGGCCGATTCACCATCTCCAGAGACAATGCCAAGAACTCACTGTAT

CTGCAAATGAACAGCCTGAGAGACGAGGACACGGCTGTGTATTACTGTGCGAGAGAGGGC

TATGCTTCGGGGAGGTATTACAACTACTACTACGGTATGGACGTCTGGGGCCAAGGGACC

ACGGTCACCGTCTCCTCA

>2E12 VH Amino acid sequence
                                             (SEQ ID NO: 22)
EVQLVESGGGLVQRGGSLRLSCAASGFTFSSYSMNWVRQAPGKGLEWISYISSSSSAIYY

ADSVKGRFTISRDNAKNSLYLQMNSLRDEDTAVYYCAREGYASGRYYNYYYGMDVWGQGT

TVTVSS
```

>2E12 VL Nucleic acid sequence
(SEQ ID NO: 23)
GAAATTGTGTTGACGCAGTCTCCAGCCACCCTGTCTTTGTCTCCAGGGGAAAGAGCCACC

CTCTCCTGCAGGGCCAGTCAGAGTGTTAGCAGCTACTTGGCCTGGTACCAACAGAAACCT

GGCCAGGCTCCCAGGCTCCTCATCTATGATGCATCCAACAGGGCCACTGGCATCCCAGCC

AGGTTCAGTGTCAGTGGGTCTGGGACAGACTTCACTCTCACCATCAGCAGCCTAGAGCCT

GAAGATTTTGCGGTTTATTACTGTCAGCAGCGTAGCAGCTGGTCGCTCACTTTCGGCGGA

GGGACCAAGGTGGAGATCAAA

>2E12 VL Amino acid sequence
(SEQ ID NO: 24)
EIVLTQSPATLSLSPGERATLSCRASQSVSSYLAWYQQKPGQAPRLLIYDASNRATGIPA

RFSVSGSGTDFTLTISSLEPEDFAVYYCQQRSSWSLTFGGGTKVEIK

The 5D3 antibody includes a heavy chain variable region (SEQ ID NO:26) encoded by the nucleic acid sequence shown in SEQ ID NO:25, and a light chain variable region (SEQ ID NO:28) encoded by the nucleic acid sequence shown in SEQ ID NO:27.

>5D3 VH Nucleic acid sequence
(SEQ ID NO: 25)
GAAGTGCAGCTGGTGGAGTCTGGGGGAGGCTTGGTACAGCCTGGCAGGTCCCTGAGACTC

TCCTGTGCAGCCTCTGGATTCACCTTTGATGATTATGCCATGCACTGGGTCCGGCAAGCT

CCAGGGAAGGGCCTGGAGTGGGTCTCAGGTATTAGTTGGAATAGTGGTAGCAGAGGCTAT

GCGGACTCTGTGAAGGGCCGATTCACCATCTCCAGAGACAACGCCAAGAACTCCCTGTAT

CTGCAAATGAACAGTCTGAGAGCTGAGGACACGGCCTTGTATTACTGTGCAAAAGATATG

GTCTACGCTTTGGACGTCTGGGGCCAAGGGACCACGGTCACCGTCTCCTCA

>5D3 VH Amino acid sequence
(SEQ ID NO: 26)
EVQLVESGGGLVQPGRSLRLSCAASGFTFDDYAMHWVRQAPGKGLEWVSGISWNSGSRGY

ADSVKGRFTISRDNAKNSLYLQMNSLRAEDTALYYCAKDMVYALDVWGQGTTVTVSS

>5D3 VL Nucleic acid sequence
(SEQ ID NO: 27)
GAAATTGTGTTGACGCAGTCTCCAGGCACCCTGTCTTTGTCTCCAGGGGAAAGAGCCACC

CTCTCCTGCAGGGCCAGTCAGAGTTTTAGCGGCAGCTACTTAGCCTGGTACCAGCAGAAA

CCTGGCCAGGCTCCCAGGCTCCTCATCTATGATACATCCAGCAGGGCCACTGGCATCCCA

GACAGGTTCAGTGGCAGTGGGTCTGGGACAGACTTCACTCTCACCATCAGCAGACTGGAG

CCTGAAGATTTTGCAGTGTATTACTGTCAGCAGTATGGTACGTGGACGTTCGGCCAAGGG

ACCAAGGTGGAAATCAAA

>5D3 VL Nucleic acid sequence
(SEQ ID NO: 28)
EIVLTQSPGTLSLSPGERATLSCRASQSFSGSYLAWYQQKPGQAPRLLIYDTSSRATGIP

DRFSGSGSGTDFTLTISRLEPEDFAVYYCQQYGTWTFGQGTKVEIK

The 22F8 antibody includes a heavy chain variable region (SEQ ID NO:30) encoded by the nucleic acid sequence shown in SEQ ID NO:29, and a light chain variable region (SEQ ID NO:32) encoded by the nucleic acid sequence shown in SEQ ID NO:31.

```
>22F8 VH Nucleic acid sequence
                                             (SEQ ID NO: 29)
GAGGTGCAGTTGTTGGAGTCTGGGGGAGGCTTGGTACAGCCTGGGGGGTCCCTGAGACTC

TCCTGTGCAGCCTCTGGATTCACCTTTAGCAGCTATGCCATGAACTGGGTCCGCCAGGCT

CCAGGGAAGGGGCTGGAGTGGGTCTCAACTATTAGTGGTCGTGGTGGTAGCATATACTAC

GCAGACTCCGTGAAGGGCCGGTTCACCATCTCCAGAGACAATTCCAAGAACACGCTGTAT

CTGCAAATGAACAGCCTGAGAGCCGAGGACACGGCCGTATATTACTGTGCGAAAGAGGAG

GCTACCTGGGACTTTGACTACTGGGGCCAAGGGACCACGGTCACCGTCTCCTCA

>22F8 VH Amino acid sequence
                                             (SEQ ID NO: 30)
EVQLLESGGGLVQPGGSLRLSCAASGFTFSSYAMNWVRQAPGKGLEWVSTISGRGGSIYY

ADSVKGRFTISRDNSKNTLYLQMNSLRAEDTAVYYCAKEEATWDFDYWGQGTTVTVSS

>22F8 VL Nucleic acid sequence
                                             (SEQ ID NO: 31)
GAAATTGTGTTGACACAGTCTCCAGCCACCCTGTCTTTGTCTCCAGGGGAAAGAGCCACC

CTCTCCTGCAGGGCCAGTCAGAGTGTTAGCAGCTTCTTAGCCTGGTTCCAACAGAAACCT

GGCCAGGCTCCCAGGCTCCTCATCTATGATGCATCCAACAGGGCCACTGGCATCCCAGCC

AGGTTCAGTGGCAGTGGGTCTGGGACAGACTTCACTCTCACCATCAGCAGCCTAGAGCCT

GAAGATTTTGCAGTTTATTACTGTCAGCAGCGTAGCAACTGGCCTCCGACGTTCGGCCAA

GGGACCAAGGTGGAAATCAAA

>22F8 VL Amino acid sequence
                                             (SEQ ID NO: 32)
EIVLTQSPATLSLSPGERATLSCRASQSVSSFLAWFQQKPGQAPRLLIYDASNRATGIPA

RFSGSGSGTDFTLTISSLEPEDFAVYYCQQRSNWPPTFGQGTKVEIK
```

The 28B11 antibody includes a heavy chain variable region (SEQ ID NO:34) encoded by the nucleic acid sequence shown in SEQ ID NO:33, and a light chain variable region (SEQ ID NO:36) encoded by the nucleic acid sequence shown in SEQ ID NO:35.

```
>28B11 VH Nucleic acid sequence
                                             (SEQ ID NO: 33)
CAGGTGCAACTGGTGGAGTCTGGGGGAGGCTTGGTCAAGCCTGGAGGGTCCCTGAGACTC

TCCTGTGCAGCCTCTGGATTCACCTTCAGTAACTACTACATGACCTGGATCCGCCAGGCT

CCAGGGAAGGGGCTGGAGTGGATTTCATACATTAGTAGTACTGGTGGTAACATCTACTAC

GCAGACTCTGTGAAGGGCCGATTCACCATCTCCAGGGACAACGCCCAGAATTCACTGTAT

CTGCAAATGAACAGCCTGAGAGCCGAGGACACGGCTGTGTATTACTGTGCGAGAGATGGG

GGTGTAATAATCTCAACTGCTATGTTTGACTATTGGGGCCAAGGGACCACGGTCACCGTC

TCCTCA

>28B11 VH Amino acid sequence
                                             (SEQ ID NO: 34)
QVQLVESGGGLVKPGGSLRLSCAASGFTFSNYYMTWIRQAPGKGLEWISYISSTGGNIYY

ADSVKGRFTISRDNAQNSLYLQMNSLRAEDTAVYYCARDGGVIISTAMFDYWGQGTTVTV

SS
```

>28B11 VL Nucleic acid sequence
(SEQ ID NO: 35)
GCCATCCAGTTGACCCAGTCTCCCTCCTCCCTGTCTGCATCTGTAGGAGACAGAGTCACC

ATCACTTGCCGGGCAAGTCAGGGCATTAGCAGTGCTTTAGCCTGGTATCAGCAGAAACCA

GGGAAAGCTCCTAAGCTCCTGATCTATGATGCCTCCAGTTTGGAAAGTGGGGTCCCATCA

AGGCTCAGCGGCAGTGGATCTGGGACAGATTTCACTCTCACCATCAGCAGCCTGCAGCCT

GAAGATTTTGCAACTTATTACTGTCAACAGTTTAATAGTTACCCGCTCACTTTCGGCGGA

GGGACCAAGGTGGAGATCAAA

>28B11 VL Amino acid sequence
(SEQ ID NO: 36)
AIQLTQSPSSLSASVGDRVTITCRASQGISSALAWYQQKPGKAPKLLIYDASSLESGVPS

RLSGSGSGTDFTLTISSLQPEDFATYYCQQFNSYPLTFGGGTKVEIK

The 41A4 antibody includes a heavy chain variable region (SEQ ID NO:38) encoded by the nucleic acid sequence shown in SEQ ID NO:37, and a light chain variable region (SEQ ID NO:40) encoded by the nucleic acid sequence shown in SEQ ID NO:39.

>41A4 VH Nucleic acid sequence
(SEQ ID NO: 37)
GAAGTGCAGCTGGTGGAGTCTGGGGGAGGCTTGGTACAGCCTGGCAGGTCCCTGAGACTC

TCCTGTGCAGCCTCTGGATTCACCTTTGATGATTGTGCCATGCACTGGGTCCGGCAAGCT

CCAGGGAAGGGCCTGGAATGGGTCTCAGGTATTAGTTGGAATAGTGGTAGCGTATACTAT

GCGGACTCTGTGAAGGGCCGATTCACCATCTCCAGAGACAACGCCAAGAATTCCCTGTAT

CTGCAAATGAACAGTCTGAGAGCTGAGGACACGGCCTTGTATTACTGTACAAAAGAAAAA

TACAACTGGAACGACGAGGGGGAATACTTCTACGGAATGGACGTCTGGGGCCAAGGGACC

ACGGTCACCGTCTCCTCA

>41A4 VH Amino acid sequence
(SEQ ID NO: 38)
EVQLVESGGGLVQPGRSLRLSCAASGFTFDDCAMHWVRQAPGKGLEWVSGISWNSGSVYY

ADSVKGRFTISRDNAKNSLYLQMNSLRAEDTALYYCTKEKYNWNDEGEYFYGMDVWGQGT

TVTVSS

>41A4 VL Nucleic acid sequence
(SEQ ID NO: 39)
GAAATTGTGTTGACACAGTCTCCAGGCACCCTGTCTTTGTCTCCAGGGGAAAGAGCCACC

CTCTCCTGCAGGGCCAGTCAGAGTGTTAGCAGCAGCTACTTAGCCTGGTACCAGCAGAAA

CCTGGCCAGGCTCCCAGGCTCCTCATCTATGGTGCATCCAGCAGGGCCACTGGCATCCCA

GACAGGTTCAGTGGCAGTGGGTCTGGGACAGACTTCACTCTCACCATCAGCAGACTGGAG

CCTGAAGATTTTGCAGTGTATTACTGTCAGCAGTATGGTAGCTCTTTCGGCGGAGGGACC

AAGGTGGAGATCAAA

>41A4 VL Amino acid sequence
(SEQ ID NO: 40)
EIVLTQSPGTLSLSPGERATLSCRASQSVSSSYLAWYQQKPGQAPRLLIYGASSRATGIP

DRFSGSGSGTDFTLTISRLEPEDFAVYYCQQYGSSFGGGTKVEIK

The 43G6 antibody includes a heavy chain variable region (SEQ ID NO:42) encoded by the nucleic acid sequence shown in SEQ ID NO:41, and a light chain variable region (SEQ ID NO:44) encoded by the nucleic acid sequence shown in SEQ ID NO:43.

```
>43G6 VH3 Nucleic acid sequence
                                              (SEQ ID NO: 41)
GAGGTGCAGCTGGTGGAGTCTGGGGGAGGCTTGGTACAGCCTGGGGGGTCCCTGAGACTC

TCCTGTGCAGCCTCTGGATTCACCTTCAGTAGCTATAGCATGAACTGGGTCCGCCAGGCT

CCAGGGAAGGGGCTGGAGTGGGTTTCATACATTAGTAGTGGTAGTAGTACCATATACTAC

GCAGACTCTGTGAAGGGCCGATTCACCATCTCCAGAGACAATGCCAAGAACTCACTGTAT

CTGCAAATGAACAGCCTGAGAGACGAGGACACGGCTGTGTATTACTGTGCGAGAGAGGGC

TATGTTTCGGGGACCTATTACAACTACTACTACGGTATGGACGTCTGGGGCCAAGGGACC

ACGGTCACCGTCTCCTCA

>43G6 VH3 Amino acid sequence
                                              (SEQ ID NO: 42)
EVQLVESGGGLVQPGGSLRLSCAASGFTFSSYSMNWVRQAPGKGLEWVSYISSGSSTIYY

ADSVKGRFTISRDNAKNSLYLQMNSLRDEDTAVYYCAREGYVSGTYYNYYYGMDVWGQGT

TVTVSS

>43G6 VL3 Nucleic acid sequence
                                              (SEQ ID NO: 43)
GAAATTGTGTTGACGCAGTCTCCAGCCACCCTGTCTTTGTCTCCAGGGGAAAGAGCCACC

CTCTCCTGCAGGGCCAGTCAGAGTGTTAGCAGTTACTTAGCCTGGTACCAACAGAAACCT

GGCCAGGCTCCCAGGCTCCTCATCTATGATGCACCCAACAGGGCCACTGGCATCCCAGCC

AGGTTCAGTGGCAGTGGGTCTGGGACAGACTTCACTCTCACCATCAGCAGCCTAGAGCCT

GAAGATTTTGCAGTTTATTACTGTCAGCAGCGTAGCAACTGGTCGCTCACTTTCGGCGGA

GGGACCAAGGTGGAGATCAAA

>43G6 VL3 Amino acid sequence
                                              (SEQ ID NO: 44)
EIVLTQSPATLSLSPGERATLSCRASQSVSSYLAWYQQKPGQAPRLLIYDAPNRATGIPA

RFSGSGSGTDFTLTISSLEPEDFAVYYCQQRSNWSLTFGGGTKVEIK
``` huIL-17F antibodies of the invention also include, e.g., the heavy chain complementarity determining regions (VH CDRs) shown in Table 1, the light chain CDRs (VL CDRs) shown in Table 2, and combinations thereof.

TABLE 1

| \multicolumn{5}{c}{VH CDR sequences from antibody clones that bind and neutralize IL-17F biological activity} |
|---|---|---|---|---|
| Clone ID | Heavy CDR1 | Heavy CDR2 | Heavy CDR3 | Gene family |
| 11C5 | IYYLH (SEQ ID NO: 45) | IINPSGGRTNYAQFQG (SEQ ID NO: 46) | GEFSSGWLDY (SEQ ID NO: 47) | IGHV1-46 |
| 21B10 | SYSMN (SEQ ID NO: 48) | YISGGSSTIYYADSVKG (SEQ ID NO: 49) | EGYVSGTYYNYYYGMDV (SEQ ID NO: 50) | IGHV3-48 |
| 1F1 | SYVMS (SEQ ID NO: 51) | AISGRGGNTFYADSVKG (SEQ ID NO: 52) | DDRRIAAGSFDY (SEQ ID NO: 53) | IGHV3-23 |
| 2E12 | SYSMN (SEQ ID NO: 48) | YISSSSSAIYYADSVKG (SEQ ID NO: 54) | EGYASGRYYNYYYGMDV (SEQ ID NO: 55) | IGHV3-48 |
| 5E12 IgG4 | DYAMH (SEQ ID NO: 56) | GISWNSGTIGYADSVKG (SEQ ID NO: 57) | ELYISDWDSYSYGMDV (SEQ ID NO: 58) | IGHV3-9 |
| 41B10 IgG4 | NAWMS (SEQ ID NO: 59) | RIKSKTDGGTTDYVAPVKG (SEQ ID NO: 60) | SYSSYWFPYYFDY (SEQ ID NO: 61) | IGHV3-15 |

TABLE 1-continued

VH CDR sequences from antibody clones that bind and neutralize IL-17F biological activity

| Clone ID | Heavy CDR1 | Heavy CDR2 | Heavy CDR3 | Gene family |
|---|---|---|---|---|
| 5D3 | DYAMH (SEQ ID NO: 56) | GISWNSGSRGYADSVKG (SEQ ID NO: 62) | DMVYALDV (SEQ ID NO: 63) | IGHV3-9 |
| 22F8 | SYAMN (SEQ ID NO: 64) | TISGRGGSIYYADSVKG (SEQ ID NO: 65) | EEATWDFDY (SEQ ID NO: 66) | IGHV3-23 |
| 28B11 | NYYMT (SEQ ID NO: 67) | YISSTGGNIYYADSVKG (SEQ ID NO: 68) | DGGVIISTAMFDY (SEQ ID NO: 69) | IGHV3-11 |
| 41A4 | DCAMH (SEQ ID NO: 70) | GISWNSGSVYYADSVKG (SEQ ID NO: 71) | EKYNWNDEGEYFYGMDV (SEQ ID NO: 72) | IGHV3-9 |
| 43G6 | SYSMN (SEQ ID NO: 48) | YISSGSSTIYYADSVKG (SEQ ID NO: 73) | EGYVSGTYYNYYYGMDV (SEQ ID NO: 50) | IGHV3-48 |

TABLE 2

VL CDR sequences from antibody clones that bind and neutralize IL-17F

| Clone ID | Light CDR1 | Light CDR2 | Light CDR3 | Gene family |
|---|---|---|---|---|
| 11C5 | RASQGISSWLA (SEQ ID NO: 74) | AASSLQS (SEQ ID NO: 75) | ANSFPLT (SEQ ID NO: 76) | IGKV1-12 IGKJ4 |
| 21B10 | RASQSVSSYLA (SEQ ID NO: 77) | DAPNRAT (SEQ ID NO: 78) | RSNWSLT (SEQ ID NO: 79) | IGKV3-11 IGKJ4 |
| 1F1 | RASQGISSALA (SEQ ID NO: 80) | DVSSLES (SEQ ID NO: 81) | FNSYPLT (SEQ ID NO: 82) | IGKV1D-13 IGKJ4 |
| 2E12 | RASQSVSSYLA (SEQ ID NO: 77) | DASNRAT (SEQ ID NO: 83) | RSSWSLT (SEQ ID NO: 84) | IGKV3-11 IGKJ4 |
| 5E12 | RASQSVSSSYLA (SEQ ID NO: 85) | GASSRAT (SEQ ID NO: 86) | QQYGSSP (SEQ ID NO: 87) | IGKV3-20 |
| 41B10 | RASQGISSWLA (SEQ ID NO: 88) | AASSLQS (SEQ ID NO: 89) | QQYNSYPIT (SEQ ID NO: 90) | IGKV1D-16 |
| 5D3 | RASQSFSGSYLA (SEQ ID NO: 91) | DTSSRAT (SEQ ID NO: 92) | QQYGTWT (SEQ ID NO: 93) | IGKV3-20 |
| 22F8 | RASQSVSSFLA (SEQ ID NO: 94) | DASNRAT (SEQ ID NO: 83) | QQRSNWPPT (SEQ ID NO: 95) | IGKV3-11 |
| 28B11 | RASQGISSALA (SEQ ID NO: 80) | DASSLES (SEQ ID NO: 96) | QQFNSYPLT (SEQ ID NO: 97) | IGKV1D-13 |
| 41A4 | RASQSVSSSYLA (SEQ ID NO: 85) | GASSRAT (SEQ ID NO: 86) | QQYGSS (SEQ ID NO: 98) | IGKV3-20 |
| 43G6 | RASQSVSSYLA (SEQ ID NO: 77) | DAPNRAT (SEQ ID NO: 78) | QQRSNWSLT (SEQ ID NO: 99) | IGKV3-11 |

The amino acids encompassing the complementarity determining regions (CDR) are as defined by E. A. Kabat et al. (See Kabat, E A, et al., Sequences of Protein of immunological interest, Fifth Edition, US Department of Health and Human Services, US Government Printing Office (1991)).

Also included in the invention are antibodies that bind to the same epitope as the antibodies described herein. For example, antibodies of the invention specifically bind to IL-17F and/or the IL-17A/IL-17F heterodimeric complex, wherein the antibody binds to an epitope that includes one or more amino acid residues on human IL-17F (Accession No. AAH70124). In some embodiments, antibodies of the invention specifically bind IL-17F and the heterodimeric IL-17A/IL-17F complex, wherein the antibody binds to an epitope on human IL-17F (e.g., Accession No. AAH70124).

Those skilled in the art will recognize that it is possible to determine, without undue experimentation, if a monoclonal antibody (e.g., fully human monoclonal antibody) has the same specificity as a monoclonal antibody of the invention (e.g., clones 5E12, 41B10, 11C5, 21B10, 1F1, 2E12, 5D3, 22F8, 28B11, 41A4 and 43G6) by ascertaining whether the former prevents the latter from binding to IL-17F and/or the heterodimeric IL-17A/IL-17F complex. If the monoclonal antibody being tested competes with the monoclonal antibody of the invention, as shown by a decrease in binding by the monoclonal antibody of the invention, then the two monoclonal antibodies bind to the same, or a closely related, epitope.

An alternative method for determining whether a monoclonal antibody has the specificity of monoclonal antibody of the invention is to pre-incubate the monoclonal antibody of the invention with soluble IL-17F and/or soluble heterodimeric IL-17A/IL-17F complex proteins and then add the monoclonal antibody being tested to determine if the monoclonal antibody being tested is inhibited in its ability to bind IL-17F and/or the heterodimeric IL-17A/IL-17F complex. If the monoclonal antibody being tested is inhibited then, in all likelihood, it has the same, or functionally equivalent, epitopic specificity as the monoclonal antibody of the invention.

Screening of monoclonal antibodies of the invention, can be also carried out, e.g., by measuring IL-17F-induced cytokine and/or chemokine production (e.g., IL-6, IL-8, G-CSF, GM-CSF, GRO-α, GRO-b, LIX, GCP-2, MIG, IP10, I-TAC, and MCP-1, RANTES, Eotaxin, SDF-1, and MIP3a) and determining whether the test monoclonal antibody is able to modulate, block, inhibit, reduce, antagonize, neutralize or otherwise interfere with IL-17F-induced cytokine and/or chemokine production.

Various procedures known within the art may be used for the production of monoclonal antibodies directed against the IL-17F, or against derivatives, fragments, analogs homologs or orthologs thereof (See, e.g., Antibodies: A Laboratory Manual, Harlow E, and Lane D, 1988, Cold Spring Harbor Laboratory Press, Cold Spring Harbor, N.Y., incorporated herein by reference). Fully human antibodies are antibody molecules in which the entire sequence of both the light chain and the heavy chain, including the CDRs, arise from human genes. Such antibodies are termed "human antibodies", or "fully human antibodies" herein. Human monoclonal antibodies are prepared, for example, using the procedures described in the Examples provided below. Human monoclonal antibodies can be also prepared by using the trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

Antibodies are purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The antibodies of the invention (e.g., 5E12, 41B10, 11C5, 21B10, 1F1, 2E12, 5D3, 22F8, 28B11, 41A4 and 43G6) are fully human monoclonal antibodies. Monoclonal antibodies that modulate, block, inhibit, reduce, antagonize, neutralize or otherwise interfere with pro-inflammatory cytokine production mediated by IL-17F are generated, e.g., by immunizing an animal with IL-17F such as, for example, murine, rat or human IL-17F or an immunogenic fragment, derivative or variant thereof. Alternatively, the animal is immunized with cells transfected with a vector containing a nucleic acid molecule encoding IL-17F, such that IL-17F is expressed and associated with the surface of the transfected cells. Alternatively, the antibodies are obtained by screening a library that contains antibody or antigen binding domain sequences for binding to IL-17F. This library is prepared, e.g., in bacteriophage as protein or peptide fusions to a bacteriophage coat protein that is expressed on the surface of assembled phage particles and the encoding DNA sequences contained within the phage particles (i.e., "phage displayed library"). Hybridomas resulting from myeloma/B cell fusions are then screened for reactivity to IL-17F.

Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Human Antibodies and Humanization of Antibodies

Monoclonal antibodies of the invention include fully human antibodies or humanized antibodies. These antibodies are suitable for administration to humans without engendering an immune response by the human against the administered immunoglobulin.

A huIL-17F antibody is generated, for example, using the procedures described in the Examples provided below.

In other, alternative methods, a huIL-17F antibody is developed, for example, using phage-display methods using antibodies containing only human sequences. Such approaches are well-known in the art, e.g., in WO92/01047 and U.S. Pat. No. 6,521,404, which are hereby incorporated by reference. In this approach, a combinatorial library of phage carrying random pairs of light and heavy chains are screened using natural or recombinant source of IL-17F or fragments thereof. In another approach, a huIL-17F antibody can be produced by a process wherein at least one step of the process includes immunizing a transgenic, non-human animal with human IL-17F protein. In this approach, some of the endogenous heavy and/or kappa light chain loci of this xenogenic non-human animal have been disabled and are incapable of the rearrangement required to generate genes encoding immunoglobulins in response to an antigen. In addition, at least one human heavy chain locus and at least one human light chain locus have been stably transfected into the animal. Thus, in response to an administered antigen, the human loci rearrange to provide genes encoding human variable regions immunospecific for the antigen. Upon immunization, therefore, the xenomouse produces B-cells that secrete fully human immunoglobulins.

A variety of techniques are well-known in the art for producing xenogenic non-human animals. For example, see U.S. Pat. No. 6,075,181 and No. 6,150,584, which is hereby incorporated by reference in its entirety. This general strategy was demonstrated in connection with generation of the first XenoMouse™ strains as published in 1994. See Green et al. Nature Genetics 7:13-21 (1994), which is hereby incorporated by reference in its entirety. See also, U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2 and European Patent No., EP 0 463 151 B1 and International Patent Applications No. WO 94/02602, WO 96/34096, WO 98/24893, WO 00/76310 and related family members.

In an alternative approach, others have utilized a "minilocus" approach in which an exogenous Ig locus is mimicked through the inclusion of pieces (individual genes) from the Ig locus. Thus, one or more VH genes, one or more $D_H$ genes, one or more $J_H$ genes, a mu constant region, and a second constant region (preferably a gamma constant region) are formed into a construct for insertion into an animal. See e.g., U.S. Pat. Nos. 5,545,806; 5,545,807; 5,591,669; 5,612,205; 5,625,825; 5,625,126; 5,633,425; 5,643,763; 5,661,016; 5,721,367; 5,770,429; 5,789,215; 5,789,650; 5,814,318; 5,877; 397; 5,874,299; 6,023,010; and 6,255,458; and European Patent No. 0 546 073 B1; and International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and related family members.

Generation of human antibodies from mice in which, through microcell fusion, large pieces of chromosomes, or entire chromosomes, have been introduced, has also been demonstrated. See European Patent Application Nos. 773 288 and 843 961.

Human anti-mouse antibody (HAMA) responses have led the industry to prepare chimeric or otherwise humanized antibodies. While chimeric antibodies have a human constant region and a immune variable region, it is expected that certain human anti-chimeric antibody (HACA) responses will be observed, particularly in chronic or multi-dose utilizations of the antibody. Thus, it would be desirable to provide fully human antibodies against IL-17F and/or the heterodimeric IL-17A/IL-17F complex in order to vitiate or otherwise mitigate concerns and/or effects of HAMA or HACA response.

The production of antibodies with reduced immunogenicity is also accomplished via humanization, chimerization and display techniques using appropriate libraries. It will be appreciated that murine antibodies or antibodies from other species can be humanized or primatized using techniques well known in the art. See e.g., Winter and Harris Immunol Today 14:43 46 (1993) and Wright et al. Crit, Reviews in Immunol. 12125-168 (1992). The antibody of interest may be engineered by recombinant DNA techniques to substitute the CH1, CH2, CH3, hinge domains, and/or the framework domain with the corresponding human sequence (See WO 92/102190 and U.S. Pat. Nos. 5,530,101, 5,585,089, 5,693, 761, 5,693,792, 5,714,350, and 5,777,085). Also, the use of Ig cDNA for construction of chimeric immunoglobulin genes is known in the art (Liu et al. P.N.A.S. 84:3439 (1987) and J. Immunol. 139:3521 (1987)). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of immunological Interest, N.I.H. publication no. 91-3242. Human C region genes are readily available from known clones. The choice of isotype will be guided by the desired effecter functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g., by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g., SV-40 early promoter, (Okayama et al. Mol. Cell. Bio. 3:280 (1983)), Rous sarcoma virus LTR (Gorman et al. P.N.A.S. 79:6777 (1982)), and moloney murine leukemia virus LTR (Grosschedl et al. Cell 41:885 (1985)). Also, as will be appreciated, native Ig promoters and the like may be used.

Further, human antibodies or antibodies from other species can be generated through display type technologies, including, without limitation, phage display, retroviral display, ribosomal display, and other techniques, using techniques well known in the art and the resulting molecules can be subjected to additional maturation, such as affinity maturation, as such techniques are well known in the art. Wright et al. Crit, Reviews in Immunol. 12125-168 (1992), Hanes and Plückthun PNAS USA 94:4937-4942 (1997) (ribosomal display), Parmley and Smith Gene 73:305-318 (1988) (phage display), Scott, TIBS, vol. 17:241-245 (1992), Cwirla et al. PNAS USA 87:6378-6382 (1990), Russel et al. Nucl. Acids Research 21:1081-1085 (1993), Hoganboom et al. Immunol. Reviews 130:43-68 (1992), Chiswell and McCafferty TIBTECH; 10:80-8A (1992), and U.S. Pat. No. 5,733,743. If display technologies are utilized to produce antibodies that are not human, such antibodies can be humanized as described above.

Using these techniques, antibodies can be generated to IL-17F expressing cells expressing cells, IL-17F itself, forms of IL-17F epitopes or peptides thereof, and expression libraries thereto (See e.g., U.S. Pat. No. 5,703,057) which can thereafter be screened as described above for the activities described herein.

The huIL-17F antibodies of the invention can be expressed by a vector containing a DNA segment encoding the single chain antibody described above.

These can include vectors, liposomes, naked DNA, adjuvant-assisted DNA. gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci. USA 87:1149 (1990), Adenovirus Vectors (see LeGal LaSalle et al., Science, 259:988 (1993); Davidson, et al., Nat. Genet. 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, CaPO$_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icy) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266: 292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of IL-17F in a sample. The antibody can also be used to try to bind to and disrupt IL-17F related signaling.

Techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

The invention also includes $F_v$, $F_{ab}$, $F_{ab'}$ and $F_{(ab')2}$ anti-IL-17F fragments, single chain anti-IL-17F antibodies, bispecific anti-IL-17F antibodies, and heteroconjugate anti-IL-17F antibodies.

Bispecific antibodies are antibodies that have binding specificities for at least two different antigens. In the present case, one of the binding specificities is for IL-17F. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from *E. coli* and chemically coupled to form bispecific antibodies. Shalaby et al., J. Exp. Med. 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating diseases and disorders associated with IL-17F signaling. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies of the invention. (See, for example, "Conjugate Vaccines," Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238: 1098 (1987).

Preferred linkers are described in the literature. (See, for example, Ramakrishnan, S. et al., Cancer Res. 44; 201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS(N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfa-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985);

Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Antibodies Against IL-17F

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2): 210-8 (2000), Wang W. "Lyophilization and development of solid protein pharmaceuticals." Int. J. Pharm. 203(1-2):1-60 (2000), Charman WN "Lipids, lipophilic drugs, and oral drug delivery-some emerging concepts." J Pharm Sci.89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

In one embodiment, antibodies of the invention, which include a monoclonal antibody of the invention (e.g., a fully human monoclonal antibody), may be used as therapeutic agents. Such agents will generally be employed to diagnose, prognose, monitor, treat, alleviate, and/or prevent a disease or pathology associated with IL-17F signaling in a subject. A therapeutic regimen is carried out by identifying a subject, e.g., a human patient suffering from (or at risk of developing) an inflammatory disease or disorder, using standard methods. An antibody preparation, preferably one having high specificity and high affinity for its target antigen, is administered to the subject and will generally have an effect due to its binding with the target. Administration of the antibody may abrogate or inhibit or interfere with the signaling function of the target (e.g., IL-17F). Administration of the antibody may abrogate or inhibit or interfere with the binding of the target (e.g., IL-17F) with an endogenous ligand (e.g., IL-17R or IL-17RC) to which it naturally binds. For example, the antibody binds to the target and modulates, blocks, inhibits, reduces, antagonizes, neutralizes, or otherwise interferes with IL-17F-induced proinflammatory cytokine production.

Diseases or disorders related to IL-17F signaling include autoimmune diseases or inflammatory diseases or disorders, including but not limited to rheumatoid arthritis, Crohn's disease, psoriasis, multiple sclerosis chronic obstructive pulmonary disease, and asthma. IL-17F was found to be up-regulated in sputum of cystic fibrosis patients (see McAllister et al., J. Immunol. 175: 404-412 (2005)), and in the colon of patients suffering from inflammatory bowel disease (see Seiderer et al., Inflamm. Bowel Dis. Dec. 18 2007, Epub. ahead of print). IL-17A/IL-17F has been shown to play a role in the recruitment of airway neutrophilia, suggesting a role in the pathogenesis of respiratory disease (see Liang et al., J. Immunol. 179(11): 7791-9 (2007)).

Autoimmune diseases include, for example, Acquired Immunodeficiency Syndrome (AIDS, which is a viral disease with an autoimmune component), alopecia greata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barrè syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjögren's syndrome, stiffman syndrome, systemic lupus erythematosus, Takayasu arteritis, temporal arteritis/giant cell arteritis, ulcerative colitis, uveitis, vitiligo and Wegener's granulomatosis.

Inflammatory disorders include, for example, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

IL-17F has also been shown to be upregulated by IL-21 signaling, suggesting that the pro-inflammatory effects associated with IL-21 signaling are mediated by IL-17F, in addition to IL-17A and/or the IL-17F/IL17A complex (Wei et al., J Biol. Chem. 282(48):34605-10 (2007)). As such, the antibodies of the invention are also useful for diagnosing, prognosing, monitoring and/or treating disorders diseases mediated by IL-21 signaling, including but not limited to inflammatory/autoimmune disorders such as inflammatory bowel disease, rheumatoid arthritis, transplant rejection, and psoriasis.

The huIL-17F antibodies of the invention are useful in treating, ameliorating, delaying the onset and/or progression or otherwise reducing the severity of an arthritic condition or one or more symptoms thereof. Prior to the instant invention, studies had determined that IL-17F played little, if any role, in the development and/or progression of autoimmune arthritic conditions. (See Ishigame et al., Immunity, vol. 30: 108-119 (2009)). The experiments and data provided in the Examples herein demonstrate the unexpected and surprising result that modulating, e.g., inhibiting, neutralizing or otherwise blocking, the expression and/or activity of the IL-17F homodimer, but not the IL-17A/IL-17F heterodimeric complex, significantly delayed the progression of the arthritic condition and reduced the level of inflammatory mediators such as TNF-α, IL-6, IFN-γ, IL-1α, MCP-1 and IL-12/IL-23 (p40) in collagen-induced arthritis, an animal model for rheumatoid arthritis.

Accordingly, the invention includes methods of treating, ameliorating, delaying the onset and/or progression, and/or alleviating a symptom of an arthritic condition by administering to a subject in need thereof a huIL-17F antibody of the invention (e.g., 5E12, 41B10, 11C5, 21B10, 1F1, 2E12, 5D3, 22F8, 28B11, 41A4 and 43G6) or an antibody that binds to the same or similar epitope as a huIL-17F antibody of the invention. The huIL-17F antibody or antibody that binds to the same epitope as a huIL-17F antibody of the invention is administered in an amount sufficient to treat, ameliorate, delay the onset, delay the progression, and/or alleviate one or more symptoms of the arthritic condition. The subject is, for example, human. In some embodiments, the arthritic condition is an autoimmune arthritic condition. For example, in some embodiments, the arthritic condition is rheumatoid arthritis.

Symptoms associated with inflammatory-related disorders include, for example, inflammation, fever, general malaise, fever, pain, often localized to the inflamed area, rapid pulse rate, joint pain or aches (arthralgia), rapid breathing or other abnormal breathing patterns, chills, confusion, disorientation, agitation, dizziness, cough, dyspnea, pulmonary infections, cardiac failure, respiratory failure, edema, weight gain, mucopurulent relapses, cachexia, wheezing, headache, and abdominal symptoms such as, for example, abdominal pain, diarrhea or constipation. Symptoms associated with immune-related disorders include, for example, inflammation, fever, loss of appetite, weight loss, abdominal symptoms such as, for example, abdominal pain, diarrhea or constipation, joint pain or aches (arthralgia), fatigue, rash, anemia, extreme sensitivity to cold (Raynaud's phenomenon), muscle weakness, muscle fatigue, changes in skin or tissue tone, shortness of breath or other abnormal breathing patterns, chest pain or constriction of the chest muscles, abnormal heart rate (e.g., elevated or lowered), light sensitivity, blurry or otherwise abnormal vision, and reduced organ function.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Efficaciousness of treatment is determined in association with any known method for diagnosing or treating the particular inflammatory-related disorder. Alleviation of one or more symptoms of the inflammatory-related disorder indicates that the antibody confers a clinical benefit.

Methods for the screening of antibodies that possess the desired specificity include, but are not limited to, enzyme linked immunosorbent assay (ELISA) and other immunologically mediated techniques known within the art.

In another embodiment, antibodies directed against IL-17F and/or the IL-17F/IL17A complex may be used in methods known within the art relating to the localization and/or quantitation of IL-17F or the IL-17A/IL-17F complex (e.g., for use in measuring levels of the IL-17F and/or the IL-17A/IL-17F complex within appropriate physiological samples, for use in diagnostic methods, for use in imaging the protein, and the like). In a given embodiment, antibodies specific to IL-17F and/or the IL-17A/IL-17F complex, or derivative, fragment, analog or homolog thereof, that contain the antibody derived antigen binding domain, are utilized as pharmacologically active compounds (referred to hereinafter as "Therapeutics").

In another embodiment, an antibody specific for IL-17F and/or the heterodimeric IL-17A/IL-17F complex can be used to isolate an IL-17F polypeptide and/or a heterodimeric IL-17A/IL-17F complex polypeptide by standard techniques, such as immunoaffinity, chromatography or immunoprecipitation. Antibodies directed against the IL-17F protein and/or the heterodimeric IL-17A/IL-17F complex (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

In yet another embodiment, an antibody according to the invention can be used as an agent for detecting the presence of IL-17F (or a protein fragment thereof) in a sample. In some embodiments, the antibody contains a detectable label. Antibodies are polyclonal, or more preferably, monoclonal. An intact antibody, or a fragment thereof (e.g., $F_{ab}$, scFv, or $F_{(ab)2}$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Therapeutic Administration and Formulations of huIL-17F Antibodies

The antibodies of the invention (also referred to herein as "active compounds"), and derivatives, fragments, analogs and homologs thereof, can be incorporated into pharmaceutical compositions suitable for administration. Principles and considerations involved in preparing such compositions, as well as guidance in the choice of components are provided, far example, in *Remington's Pharmaceutical Sciences: The Science And Practice Of Pharmacy* 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Such compositions typically comprise the antibody and a pharmaceutically acceptable carrier. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)).

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated.

The formulations to be used for in vivo administration must be sterile. This is readily accomplished by filtration through sterile filtration membranes.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a sustained/controlled release formulations, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

For example, the active ingredients can be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The materials can also be obtained commercially from Alza Corporation and Nova Pharmaceuticals, Inc. Liposomal suspensions (including liposomes targeted to infected cells with monoclonal antibodies to viral antigens) and can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

In one embodiment, the active compounds are administered in combination therapy, i.e., combined with other agents, e.g., therapeutic agents, that are useful for treating pathological conditions or disorders, such as autoimmune disorders and inflammatory diseases. The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

For example, the combination therapy can include one or more antibodies of the invention coformulated with, and/or coadministered with, one or more additional therapeutic agents, e.g., one or more cytokine and growth factor inhibitors, immunosuppressants, anti-inflammatory agents, metabolic inhibitors, enzyme inhibitors, and/or cytotoxic or cytostatic agents, as described in more detail below. Furthermore, one or more antibodies described herein may be used in combination with two or more of the therapeutic agents described herein. Such combination therapies may advantageously utilize lower dosages of the administered therapeutic agents, thus avoiding possible toxicities or complications associated with the various monotherapies.

Preferred therapeutic agents used in combination with an antibody of the invention are those agents that interfere at different stages in an inflammatory response. In one embodiment, one or more antibodies described herein may be coformulated with, and/or coadministered with, one or more additional agents such as other cytokine or growth factor antagonists (e.g., soluble receptors, peptide inhibitors, small molecules, ligand fusions); or antibodies or antigen binding fragments thereof that bind to other targets (e.g., antibodies that bind to other cytokines or growth factors, their receptors, or other cell surface molecules); and anti-inflammatory cytokines or agonists thereof. Nonlimiting examples of the agents that can be used in combination with the antibodies described herein, include, but are not limited to, antagonists of one or more interleukins (ILs) or their receptors, e.g., antagonists of IL-1, IL-2, IL-6, IL-7, IL-8, IL-12, IL-13, IL-15, IL-16, IL-18, IL-21 and IL-22; antagonists of cytokines or growth factors or their receptors, such as tumor necrosis factor (TNF), LT, EMAP-II, GM-CSF, FGF and PDGF. Antibodies of the invention can also be combined with inhibitors of, e.g., antibodies to, cell surface molecules such as CD2, CD3, CD4, CD8, CD20 (e.g., the CD20 inhibitor rituximab (RITUXAN®)), CD25, CD28, CD30, CD40, CD45, CD69, CD80 (B7.1), CD86 (B7.2), CD90, or their ligands, including CD154 (gp39 or CD4OL), or LFA-1/ICAM-1 and VLA-4NCAM-1 (Yusuf-Makagiansar et al. (2002) Med. Res. Rev. 22:146-67). Preferred antagonists that can be used in combination with the antibodies described herein include antagonists of IL-1, IL-12, TNFα, IL-15, IL-18, and IL-22.

Examples of those agents include IL-12 antagonists, such as chimeric, humanized, human or in vitro-generated antibodies (or antigen binding fragments thereof) that bind to IL-12 (preferably human IL-12), e.g., the antibody disclosed in WO 00/56772; IL-12 receptor inhibitors, e.g., antibodies to human IL-12 receptor; and soluble fragments of the IL-12 receptor, e.g., human IL-12 receptor. Examples of IL-15 antagonists include antibodies (or antigen binding fragments thereof) against IL-15 or its receptor, e.g., chimeric, humanized, human or in vitro-generated antibodies to human IL-15 or its receptor, soluble fragments of the IL-15 receptor, and IL-15-binding proteins. Examples of IL-18 antagonists include antibodies, e.g., chimeric, humanized, human or in vitro-generated antibodies (or antigen binding fragments thereof), to human IL-18, soluble fragments of the IL-18 receptor, and IL-18 binding proteins (IL-18BP). Examples of IL-1 antagonists include Interleukin-1-converting enzyme (ICE) inhibitors, such as Vx740, IL-1 antagonists, e.g., IL-1RA (anikinra, KINERET™, Amgen), sIL1RII (Immunex), and anti-IL-1 receptor antibodies (or antigen binding fragments thereof).

Examples of TNF antagonists include chimeric, humanized, human or in vitro-generated antibodies (or antigen binding fragments thereof) to TNF (e.g., human TNFα), such as (HUMIRA™, D2E7, human TNFα antibody), CDP-571/CDP-870/BAY-10-3356 (humanized anti-TNFα antibody; Celltech/Pharmacia), cA2 (chimeric anti-TNFα antibody; REMICADE®, Centocor); anti-TNF antibody fragments (e.g., CPD870); soluble fragments of the TNF receptors, e.g., p55 or p75 human TNF receptors or derivatives thereof, e.g., 75 kdTNFR-IgG (75 kD TNF receptor-IgG fusion protein, ENBREL™; Immunex), p55 kdTNFR-IgG (55 kD TNF receptor-IgG fusion protein (LENERCEP®); enzyme antagonists, e.g., TNFα converting enzyme (TACE) inhibitors (e.g., an alpha-sulfonyl hydroxamic acid derivative, and N-hydroxyformamide TACE inhibitor GW 3333, -005, or -022); and TNF-bp/s-TNFR (soluble TNF binding protein). Preferred TNF antagonists are soluble fragments of the TNF receptors, e.g., p55 or p75 human TNF receptors or derivatives thereof, e.g., 75 kdTNFR-IgG, and TNFα converting enzyme (TACE) inhibitors.

In other embodiments, the antibodies described herein may be administered in combination with one or more of the following: IL-13 antagonists, e.g., soluble IL-13 receptors (sIL-13) and/or antibodies against IL-13; IL-2 antagonists, e.g., DAB 486-IL-2 and/or DAB 389-IL-2 (IL-2 fusion proteins, Seragen), and/or antibodies to IL-2R, e.g., anti-Tac (humanized anti-IL-2R, Protein Design Labs). Yet another combination includes antibodies of the invention, antagonistic small molecules, and/or inhibitory antibodies in combination with nondepleting anti-CD4 inhibitors (DEC-CE9.1/SB 210396; nondepleting primatized anti-CD4 antibody; IDEC/SmithKline). Yet other preferred combinations include antagonists of the costimulatory pathway CD80 (B7.1) or CD86 (B7.2), including antibodies, soluble receptors or antagonistic ligands; as well as p-selectin glycoprotein ligand (PSGL), anti-inflammatory cytokines, e.g., IL-4 (DNAX/Schering); IL-10 (SCH 52000; recombinant IL-10 DNAX/Schering); IL-13 and TGF-β, and agonists thereof (e.g., agonist antibodies).

In other embodiments, one or more antibodies of the invention can be coformulated with, and/or coadministered with, one or more anti-inflammatory drugs, immunosuppressants, or metabolic or enzymatic inhibitors. Nonlimiting examples of the drugs or inhibitors that can be used in combination with the antibodies described herein, include, but are not limited to, one or more of: nonsteroidal anti-inflammatory drug(s) (NSAIDs), e.g., ibuprofen, tenidap, naproxen, meloxicam, piroxicam, diclofenac, and indomethacin; sulfasalazine; corticosteroids such. as prednisolone; cytokine suppressive anti-inflammatory drug(s) (CSAIDs); inhibitors of nucleotide biosynthesis, e.g., inhibitors of purine biosynthesis, folate antagonists (e.g., methotrexate (N-[4-[[(2,4-diamino-6-pteridinyl)methyl]methylamino]benzoyl]-L-glutamic acid); and inhibitors of pyrimidine biosynthesis, e.g., dihydroorotate dehydrogenase (DHODH) inhibitors. Preferred therapeutic agents for use in combination with the antibodies of the invention include NSAIDs, CSAIDs, (DHODH) inhibitors (e.g., leflunomide), and folate antagonists (e.g., methotrexate).

Examples of additional inhibitors include one or more of: corticosteroids (oral, inhaled and local injection); immunosuppresants, e.g., cyclosporin, tacrolimus (FK-506); and mTOR inhibitors, e.g., sirolimus (rapamycin—RAPAMUNE™ or rapamycin derivatives, e.g., soluble rapamycin derivatives (e.g., ester rapamycin derivatives, e.g., CCI-779); agents which interfere with signaling by proinflammatory cytokines such as TNFα or IL-1 (e.g. IRAK, NIK, IKK, p38 or MAP kinase inhibitors); COX2 inhibitors, e.g., celecoxib, rofecoxib, and variants thereof; phosphodiesterase inhibitors, e.g., R973401 (phosphodiesterase Type IV inhibitor); phospholipase inhibitors, e.g., inhibitors of cytosolic phospholipase 2 (cPLA2) (e.g., trifluoromethyl ketone analogs); inhibitors of vascular endothelial cell growth factor or growth factor receptor, e.g., VEGF inhibitor and/or VEGF-R inhibitor; and inhibitors of angiogenesis. Preferred therapeutic agents for use in combination with the antibodies of the invention are immunosuppresants, e.g., cyclosporin, tacrolimus (FK-506); mTOR inhibitors, e.g., sirolimus (rapamycin) or rapamycin derivatives, e.g., soluble rapamycin derivatives (e.g., ester rapamycin derivatives, e.g., CCI-779); COX2 inhibitors, e.g., celecoxib and variants thereof; and phospholipase inhibitors, e.g., inhibitors of cytosolic phospholipase 2 (cPLA2), e.g., trifluoromethyl ketone analogs.

Additional examples of therapeutic agents that can be combined with an antibody of the invention include one or more of: 6-mercaptopurines (6-MP); azathioprine sulphasalazine; mesalazine; olsalazine; chloroquine/hydroxychloroquine (PLAQUENIL®); pencillamine; aurothiornalate (intramuscular and oral); azathioprine; coichicine; beta-2 adrenoreceptor agonists (salbutamol, terbutaline, salmeteral); xanthines (theophylline, aminophylline); cromoglycate; nedocromil; ketotifen; ipratropium and oxitropium; mycophenolate mofetil; adenosine agonists; antithrombotic agents; complement inhibitors; and adrenergic agents.

Nonlimiting examples of agents for treating or preventing arthritic disorders (e.g., rheumatoid arthritis, inflammatory arthritis, rheumatoid arthritis, juvenile rheumatoid arthritis, osteoarthritis and psoriatic arthritis), with which an antibody of the invention may be combined include one or more of the following: IL-12 antagonists as described herein; NSAIDs;

CSAIDs; TNFs, e.g., TNFα, antagonists as described herein; nondepleting anti-CD4 antibodies as described herein; IL-2 antagonists as described herein; anti-inflammatory cytokines, e.g., IL-4, IL-10, IL-13 and TGFα, or agonists thereof; IL-1 or IL-1 receptor antagonists as described herein; phosphodiesterase inhibitors as described herein; Cox-2 inhibitors as described herein; iloprost: methotrexate; thalidomide and thalidomide-related drugs (e.g., Celgen); leflunomide; inhibitor of plasminogen activation, e.g., tranexamic acid; cytokine inhibitor, e.g., T-614; prostaglandin E1; azathioprine; an inhibitor of interleukin-1 converting enzyme (ICE); zap-70 and/or lck inhibitor (inhibitor of the tyrosine kinase zap-70 or lck); an inhibitor of vascular endothelial cell growth factor or vascular endothelial cell growth factor receptor as described herein; an inhibitor of angiogenesis as described herein; corticosteroid anti-inflammatory drugs (e.g., SB203580); TNF-convertase inhibitors; IL-11; IL-13; IL-17 inhibitors; gold; penicillamine; chloroquine; hydroxychloroquine; chlorambucil; cyclophosphamide; cyclosporine; total lymphoid irradiation; antithymocyte globulin; CD5-toxins; orally administered peptides and collagen; lobenzarit disodium; cytokine regulating agents (CRAs) HP228 and HP466 (Houghten Pharmaceuticals, Inc.); ICAM-1 antisense phosphorothioate oligodeoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline (MINOCIN®); anti-IL2R antibodies; marine and botanical lipids (fish and plant seed fatty acids); auranofm; phenylbutazone; meclofenamic acid; flufenamic acid; intravenous immune globulin; zileuton; mycophenolic acid (RS-61443); tacrolimus (FK-506); sirolimus (rapamycin); amiprilose (therafectin); cladribine (2-chlorodeoxyadenosine); and azaribine. Preferred combinations include one or more antibodies of the invention in combination with methotrexate or leflunomide, and in moderate or severe rheumatoid arthritis cases, cyclosporine.

Preferred examples of inhibitors to use in combination with antibodies of the invention to treat arthritic disorders include TNF antagonists (e.g., chimeric, humanized, human or in vitro-generated antibodies, or antigen binding fragments thereof, that bind to TNF; soluble fragments of a TNF receptor, e.g., p55 or p75 human TNF receptor or derivatives thereof, e.g., 75 kdTNFR-IgG (75 kD TNF receptor-IgG fusion protein, ENBREL™), p55 kD TNF receptor-IgG fusion protein; TNF enzyme antagonists, e.g., TNFα converting enzyme (TACE) inhibitors); antagonists of IL-12, IL-15, IL-18, IL-22; T cell and B cell-depleting agents (e.g., anti-CD4 or anti-CD22 antibodies); small molecule inhibitors, e.g., methotrexate and leflunomide; sirolimus (rapamycin) and analogs thereof, e.g., CCI-779; cox-2 and cPLA2 inhibitors; NSAIDs; p38 inhibitors, TPL-2, Mk-2 and NFkb inhibitors; RAGE or soluble RAGE; P-selectin or PSGL-1 inhibitors (e.g., small molecule inhibitors, antibodies thereto, e.g., antibodies to P-selectin); estrogen receptor beta (ERB) agonists or ERB-NFkb antagonists. Most preferred additional therapeutic agents that can be coadministered and/or coformulated with one or more antibodies of the invention include one or more of a soluble fragment of a TNF receptor, e.g., p55 or p75 human TNF receptor or derivatives thereof, e.g., 75 kdTNFR-IgG (75 kD TNF receptor-IgG fusion protein, ENBREL™); methotrexate, leflunomide, or a sirolimus (rapamycin) or an analog thereof, e.g., CCI-779.

Nonlimiting examples of agents for treating or preventing multiple sclerosis with which antibodies of the invention can be combined include the following: interferons, e.g., interferon-alpha 1a (e.g., AVONEX™; Biogen) and interferon-1b (BETASERON™ Chiron/Berlex); Copolymer 1 (Cop-1; COPAXONE™ Teva Pharmaceutical Industries, Inc.); hyperbaric oxygen; intravenous immunoglobulin; cladribine; TNF antagonists as described herein; corticosteroids; prednisolone; methylprednisolone; azathioprine; cyclophosphamide; cyclosporine; cyclosporine A, methotrexate; 4-aminopyridine; and tizanidine. Additional antagonists that can be used in combination with antibodies of the invention include antibodies to or antagonists of other human cytokines or growth factors, for example, TNF, LT, IL-1, IL-2, IL-6, EL-7, IL-8, IL-12 IL-15, IL-16, IL-18, EMAP-11, GM-CSF, FGF, and PDGF. Antibodies as described herein can be combined with antibodies to cell surface molecules such as CD2, CD3, CD4, CD8, CD25, CD28, CD30, CD40, CD45, CD69, CD80, CD86, CD90 or their ligands. The antibodies of the invention may also be combined with agents, such as methotrexate, cyclosporine, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signaling by proinflammatory cytokines as described herein, IL-1b converting enzyme inhibitors (e.g., Vx740), anti-P7s, PSGL, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof, as described herein, and anti-inflammatory cytokines (e.g. IL-4, IL-10, IL-13 and TGF).

Preferred examples of therapeutic agents for multiple sclerosis with which the antibodies of the invention can be combined include interferon-β, for example, IFNβ-1a and IFNβ-1b; copaxone, corticosteroids, IL-1 inhibitors, TNF inhibitors, antibodies to CD40 ligand and CD80, IL-12 antagonists.

Nonlimiting examples of agents for treating or preventing inflammatory bowel disease (e.g., Crohn's disease, ulcerative colitis) with which an antibody of the invention can be combined include the following: budenoside; epidermal growth factor; corticosteroids; cyclosporine; sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1 monoclonal antibodies; anti-IL-6 monoclonal antibodies; growth factors; elastase inhibitors; pyridinyl-imidazole compounds; TNF antagonists as described herein; IL-4, IL-10, IL-13 and/or TGFβ cytokines or agonists thereof (e.g., agonist antibodies); IL-11; glucuronide- or dextran-conjugated prodrugs of prednisolone, dexamethasone or budesonide; ICAM-1 antisense phosphorothioate oligodeoxynucleotides (ISIS 2302; Isis Pharmaceuticals, Inc.); soluble complement receptor 1 (TP10; T Cell Sciences, Inc.); slow-release mesalazine; methotrexate; antagonists of platelet activating factor (PAF); ciprofloxacin; and lignocaine.

Nonlimiting examples of agents for treating or preventing psoriasis with which an antibody of the invention can be combined include the following: corticosteroids; vitamin $D_3$ and analogs thereof; retinoids (e.g., soriatane); methotrexate; cyclosporine, 6-thioguanine; Accutane; hydrea; hydroxyurea; sulfasalazine; mycophenolate mofetil; azathioprine; tacrolimus; fumaric acid esters; biologics such as Amevive, Enbrel, Humira, Raptiva and Remicade, Ustekinmab, and XP-828L; phototherapy; and photochemotherapy (e.g., psoralen and ultraviolet phototherapy combined).

Nonlimiting examples of agents for treating or preventing inflammatory airway/respiratory disease (e.g., chronic obstructive pulmonary disorder, asthma) with which an antibody of the invention can be combined include the following: beta2-adrenoceptor agonists (e.g., salbutamol (albuterol USAN), levalbuterol, terbutaline, bitolterol); long-acting beta2-adrenoceptor agonists (e.g., salmeterol, formoterol, bambuterol); adrenergic agonists (e.g., inhaled epinephrine and ephedrine tablets); anticholinergic medications (e.g., ipratropium bromide); Combinations of inhaled steroids and long-acting bronchodilators (e.g., fluticasone/salmeterol (Advair in the United States, and Seretide in the United Kingdom)) or. budesonide/formoterol (Symbicort)); inhaled glucocorticoids (e.g., ciclesonide, beclomethasone, budesonide, flunisolide, fluticasone, mometasone, triamcinolone); leukotriene modifiers (e.g., montelukast, zafirlukast, pranlukast, and zileuton); mast cell stabilizers (e.g., cromoglicate (cromolyn), and nedocromil); antimuscarinics/anticholinergics (e.g., ipratropium, oxitropium, tiotropium); methylxanthines (e.g., theophylline, aminophylline); antihistamines; IgE blockers (e.g., Omalizumab); $M_3$ muscarinic antagonists (anticholinergics) (e.g., ipratropium, tiotropium); cromones (e.g., chromoglicate, nedocromil); xanthines (e.g., theophylline); and TNF antagonists (e.g., infliximab, adalimumab and etanercept).

In one embodiment, an antibody of the invention can be used in combination with one or more antibodies directed at other targets involved in regulating immune responses, e.g., transplant rejection.

Nonlimiting examples of agents for treating or preventing immune responses with which an antibody of the invention can be combined include the following: antibodies against other cell surface molecules, including but not limited to CD25 (interleukin-2 receptor-a), CD11a (LFA-1), CD54 (ICAM-1), CD4, CD45, CD28/CTLA4 (CD80 (137.1), e.g., CTLA4 Ig—abatacept (ORENCIA®)), ICOSL, ICOS and/or CD86 (B7.2). In yet another embodiment, an antibody of the invention is used in combination with one or more general immunosuppressive agents, such as cyclosporin A or FK506.

In other embodiments, antibodies are used as vaccine adjuvants against autoimmune disorders, inflammatory diseases, etc. The combination of adjuvants for treatment of these types of disorders are suitable for use in combination with a wide variety of antigens from targeted self-antigens, i.e., autoantigens, involved in autoimmunity, e.g., myelin basic protein; inflammatory self-antigens, e.g., amyloid peptide protein, or transplant antigens, e.g., alloantigens. The antigen may comprise peptides or polypeptides derived from proteins, as well as fragments of any of the following: saccharides, proteins, polynucleotides or oligonucleotides, autoantigens, amyloid peptide protein, transplant antigens, allergens, or other macromolecular components. In some instances, more than one antigen is included in the antigenic composition.

For example, desirable vaccines for moderating responses to allergens in a vertebrate host, which contain the adjuvant combinations of this invention, include those containing an allergen or fragment thereof. Examples of such allergens are described in U.S. Pat. No. 5,830,877 and published International Patent Application No. WO 99/51259, which are hereby incorporated by reference in their entireties, and include pollen, insect venoms, animal dander, fungal spores and drugs (such as penicillin). The vaccines interfere with the production of IgE antibodies, a known cause of allergic reactions. In another example, desirable vaccines for preventing or treating disease characterized by amyloid deposition in a vertebrate host, which contain the adjuvant combinations of this invention, include those containing portions of amyloid peptide protein (APP). This disease is referred to variously as Alzheimer's disease, amyloidosis or amyloidogenic disease. Thus, the vaccines of this invention include the adjuvant combinations of this invention plus Aβ peptide, as well as fragments of Aβ peptide and antibodies to Aβ peptide or fragments thereof.

Design and Generation of Other Therapeutics

In accordance with the present invention and based on the activity of the antibodies that are produced and characterized herein with respect to IL-17F and/or the heterodimeric IL-17A/IL-17F complex, the design of other therapeutic modalities beyond antibody moieties is facilitated. Such modalities include, without limitation, advanced antibody therapeutics, such as bispecific antibodies, immunotoxins, and radiolabeled therapeutics, generation of peptide therapeutics, gene therapies, particularly intrabodies, antisense therapeutics, and small molecules.

For example, in connection with bispecific antibodies, bispecific antibodies can be generated that comprise (i) two antibodies one with a specificity to IL-17F and/or the heterodimeric IL-17A/IL-17F complex, and another to a second molecule that are conjugated together, (ii) a single antibody that has one chain specific to IL-17F and/or the heterodimeric IL-17A/IL-17F complex, and a second chain specific to a second molecule, or (iii) a single chain antibody that has specificity to IL-17F and/or the heterodimeric IL-17A/IL-17F complex, and a second molecule. Such bispecific antibodies are generated using techniques that are well known for example, in connection with (i) and (ii) See e.g., Fanger et al. Immunol Methods 4:72-81 (1994) and Wright et al. Crit, Reviews in Immunol. 12125-168 (1992), and in connection with (iii) See e.g., Traunecker et al. Int. J. Cancer (Suppl.) 7:51-52 (1992).

In connection with immunotoxins, antibodies can be modified to act as immunotoxins utilizing techniques that are well known in the art See e.g., Vitetta Immunol Today 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in Cancer Chemotherapy and Biotherapy 655-686 (2d edition, Chafner and Longo, eds., Lippincott Raven (1996)). See also U.S. Pat. Nos. 4,681,581, 4,735,210, 5,101,827, 5,102,990 (RE 35,500), U.S. Pat. Nos. 5,648,471, and 5,697,902. Each of immunotoxins and radiolabeled molecules would be likely to kill cells expressing IL-17F and/or the heterodimeric IL-17A/IL-17F complex.

In connection with the generation of therapeutic peptides, through the utilization of structural information related to IL-17F and/or the heterodimeric IL-17A/IL-17F complex and antibodies thereto, such as the antibodies of the invention or screening of peptide libraries, therapeutic peptides can be generated that are directed against IL-17F and/or the heterodimeric IL-17A/IL-17F complex. Design and screening of peptide therapeutics is discussed in connection with Houghten et al. Biotechniques 13:412-421 (1992), Houghten PNAS USA 82:5131-5135 (1985), Pinalla et al. Biotechniques 13:901-905 (1992), Blake and Litzi-Davis BioConjugate Chem. 3:510-513 (1992). Immunotoxins and radiolabeled molecules can also be prepared, and in a similar manner, in connection with peptidic moieties as discussed above in connection with antibodies. Assuming that the IL-17F and/or the heterodimeric IL-17A/IL-17F complex molecule (or a form, such as a splice variant or alternate form) is functionally active in a disease process, it will also be possible to design gene and antisense therapeutics thereto through conventional techniques. Such modalities can be utilized for modulating the function of IL-17F and/or the heterodimeric IL-17A/IL-17F complex. In connection therewith the antibodies of the present invention facilitate design and use of functional assays related thereto. A design and strategy for antisense therapeutics is discussed in detail in International Patent Application No. WO 94/29444. Design and strategies for gene therapy are well known. However, in particular, the use of gene therapeutic techniques involving intrabodies could prove to be particularly advantageous. See e.g., Chen et al. Human Gene Therapy 5:595-601 (1994) and Marasco Gene Therapy 4:11-15 (1997). General design of and considerations related to gene therapeutics is also discussed in International Patent Application No. WO 97/38137.

Knowledge gleaned from the structure of the IL-17F and/or the heterodimeric IL-17A/IL-17F complex molecule and its interactions with other molecules in accordance with the present invention, such as the antibodies of the invention, and others can be utilized to rationally design additional therapeutic modalities. In this regard, rational drug design techniques such as X-ray crystallography, computer-aided (or assisted) molecular modeling (CAMM), quantitative or qualitative structure-activity relationship (QSAR), and similar technologies can be utilized to focus drug discovery efforts. Rational design allows prediction of protein or synthetic structures which can interact with the molecule or specific forms thereof which can be used to modify or modulate the activity of IL-17F, and/or the heterodimeric IL-17A/IL-17F complex. Such structures can be synthesized chemically or expressed in biological systems. This approach has been reviewed in Capsey et al. Genetically Engineered Human Therapeutic Drugs (Stockton Press, NY (1988)). Further, combinatorial libraries can be designed and synthesized and used in screening programs, such as high throughput screening efforts.

Screening Methods

The invention provides methods (also referred to herein as "screening assays") for identifying modulators, i.e., candidate or test compounds or agents (e.g., peptides, peptidomimetics, small molecules or other drugs) that modulate, block, inhibit, reduce, antagonize, neutralize or otherwise interfere with binding of IL-17F and/or the heterodimeric IL-17A/IL-17F complex to their innate receptor, or candidate or test compounds or agents that modulate, block, inhibit, reduce, antagonize, neutralize or otherwise interfere with the signaling function of IL-17F and/or the heterodimeric IL-17A/IL-17F complex. Also provided are methods of identifying compounds useful to treat disorders associated with IL-17F and/or heterodimeric IL-17A/IL-17F complex signaling. The invention also includes compounds identified in the screening assays described herein.

In one embodiment, the invention provides assays for screening candidate or test compounds which modulate the signaling function of IL-17F and/or the heterodimeric IL-17A/IL-17F complex. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. (See, e.g., Lam, 1997. Anticancer Drug Design 12: 145).

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37: 1233.

Libraries of compounds may be presented in solution (see e.g., Houghten, 1992. Biotechniques 13: 412-421), or on beads (see Lam, 1991. Nature 354: 82-84), on chips (see Fodor, 1993. Nature 364: 555-556), bacteria (see U.S. Pat. No. 5,223,409), spores (see U.S. Pat. No. 5,233,409), plasmids (see Cull, et al., 1992. Proc. Natl. Acad. Sci. USA 89: 1865-1869) or on phage (see Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; and U.S. Pat. No. 5,233, 409.).

In one embodiment, a candidate compound is introduced to an antibody-antigen complex and determining whether the candidate compound disrupts the antibody-antigen complex, wherein a disruption of this complex indicates that the candidate compound modulates the signaling function of IL-17F and/or the heterodimeric IL-17A/IL-17F complex. For example, the antibody is monoclonal antibody 5E12 ("Mab05") and the antigen is IL-17F and/or the heterodimeric IL-17A/IL-17F complex.

In another embodiment, the IL-17F homodimer is provided and exposed to at least one neutralizing monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat disorders associated with IL-17F signaling.

In another embodiment, a soluble protein of IL-17F is provided and exposed to at least one neutralizing monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat disorders associated with IL-17F signaling.

Determining the ability of the test compound to interfere with or disrupt the antibody-antigen complex can be accomplished, for example, by coupling the test compound with a radioisotope or enzymatic label such that binding of the test compound to the antigen or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product.

In one embodiment, the assay comprises contacting an antibody-antigen complex with a test compound, and determining the ability of the test compound to interact with the antigen or otherwise disrupt the existing antibody-antigen complex. In this embodiment, determining the ability of the test compound to interact with the antigen and/or disrupt the antibody-antigen complex comprises determining the ability of the test compound to preferentially bind to the antigen or a biologically-active portion thereof, as compared to the antibody.

In another embodiment, the assay comprises contacting an antibody-antigen complex with a test compound and determining the ability of the test compound to modulate the antibody-antigen complex. Determining the ability of the test compound to modulate the antibody-antigen complex can be accomplished, for example, by determining the ability of the antigen to bind to or interact with the antibody, in the presence of the test compound.

Those skilled in the art will recognize that, in any of the screening methods disclosed herein, the antibody may be a neutralizing antibody, such as for example monoclonal antibody 5E12, 41B10, 11C5, 21B10, 1F1, 2E12, 5D3, 22F8, 28B11, 41A4, and 43G6, each of which modulates or otherwise interferes with proinflammatory cytokine production.

The screening methods disclosed herein may be performed as a cell-based assay or as a cell-free assay. The cell-free assays of the invention are amenable to use soluble IL-17F, soluble IL-17A/IL-17F complex and fragments thereof.

In more than one embodiment; it may be desirable to immobilize either the antibody or the antigen to facilitate separation of complexed from uncomplexed forms of one or both following introduction of the candidate compound, as well as to accommodate automation of the assay. Observation of the antibody-antigen complex in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-antibody fusion proteins or GST-antigen fusion proteins can be adsorbed onto glutathione sepharose beads (Sigma Chemical, St. Louis, Mo.) or glutathione derivatized microtiter plates, that are then combined with the test compound, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of antibody-antigen complex formation can be determined using standard techniques.

Other techniques for immobilizing proteins on matrices can also be used in the screening assays of the invention. For example, either the antibody (e.g. 5E12, 41B10, 11C5, 21B10, 1F1, 2E12, 5D3, 22F8, 28B11, 41A4, and 43G6) or the antigen (e.g. the IL-17F protein or the IL-17A/IL-17F complex) can be immobilized utilizing conjugation of biotin and streptavidin. Biotinylated antibody or antigen molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, other antibodies reactive with the antibody or antigen of interest, but which do not interfere with the formation of the antibody-antigen complex of interest, can be derivatized to the wells of the plate, and unbound antibody or antigen trapped in the wells by antibody conjugation. Methods for detecting such complexes, in addition to those described above for the GST-immobilized complexes, include immuno detection of complexes using such other antibodies reactive with the antibody or antigen.

The invention further pertains to novel agents identified by any of the aforementioned screening assays and uses thereof for treatments as described herein.

Diagnostic and Prophylactic Formulations

The huIL-17F MAbs of the invention are used in diagnostic and prophylactic formulations. In one embodiment, an IL-17F antagonist, such as a huIL-17F MAb of the invention, is administered to patients that are at risk of developing one or more of the aforementioned autoimmune or inflammatory diseases, such as for example, without limitation, rheumatoid arthritis and other autoimmune arthritic conditions, Crohn's disease, psoriasis, multiple sclerosis chronic obstructive pulmonary disease, asthma, osteoarthritis and cancer. A patient's or organ's predisposition to one or more of the aforementioned autoimmune or inflammatory diseases can be determined using genotypic, serological or biochemical markers.

In another embodiment of the invention, an IL-17F antagonist, such as a huIL-17F antibody is administered to human individuals diagnosed with a clinical indication associated with one or more of the aforementioned autoimmune or inflammatory diseases such as rheumatoid arthritis or other autoimmune arthritic conditions, Crohn's disease, psoriasis, multiple sclerosis chronic obstructive pulmonary disease, asthma, osteoarthritis, and cancer. Upon diagnosis, an IL-17F antagonist, such as a huIL-17F antibody is administered to mitigate or reverse the effects of the clinical indication associated with rheumatoid arthritis and other autoimmune arthritic conditions, Crohn's disease, psoriasis, multiple sclerosis chronic obstructive pulmonary disease, asthma, osteoarthritis and cancer.

Antibodies of the invention are also useful in the detection of IL-17F and/or the heterodimeric IL-17A/IL-17F complex in patient samples and accordingly are useful as diagnostics. For example, the huIL-17F antibodies of the invention are used in in vitro assays, e.g., ELISA, to detect IL-17F and/or heterodimeric IL-17A/IL-17F complex levels in a patient sample.

In one embodiment, a huIL-17F antibody of the invention is immobilized on a solid support (e.g., the well(s) of a microtiter plate). The immobilized antibody serves as a capture antibody for any IL-17F and/or any heterodimeric IL-17A/IL-17F complex that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of IL-17F and/or the heterodimeric IL-17A/IL-17F complex antigen in the test sample is determined by comparison with a standard curve developed from the standard samples.

It will be appreciated that based on the results obtained using the huIL-17F antibodies of the invention in an in vitro diagnostic assay, it is possible to stage a disease (e.g., a clinical indication associated with ischemia, an autoimmune or inflammatory disorder) in a subject based on expression levels of the IL-17F and/or the heterodimeric IL-17A/IL-17F complex antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

The following examples, including the experiments conducted and results achieved are provided for illustrative purposes only and are not to be construed as limiting upon the present invention.

Example 1

Cloning, Expression and Purification of Human IL-17F, Rat IL-17F, Cynomolgus IL-17F Cloning The cDNAs encoding the mature human IL-17F (AF384857, aa 31-163) rat IL-17F (AAH91568, aa 21-153) and cynomolgus IL-17F (identical to sequence XP_001106517 aa 31-163,) were amplified by PCR and cloned in PCR4TOPO vector (Invitrogen). Upon another PCR step, a His tag or a His tag followed by an AviTag (Avidity, Denver Colo.) were introduced at the N-terminus of the cytokine coding sequence. These constructs were then fused to a leader sequence and sub-cloned in a corresponding expression vectors.

Expression and Purification of Human IL-17F and Rat IL-17F from Baculovirus-Infected Cells His-tagged huIL-17F or rat IL-17F preceded by the GP67 leader sequence (MLLVNQSHQGFNKEHTSKMVSAIV-LYVLLAAAAHSAFA) (SEQ ID NO: 100) were sub-cloned into a baculovirus bacmid vector pFASTBAC Dual (Invitrogen). After transfection into Sf9 cells, recombinant virus was isolated and amplified. For protein production, Hi5 cells or SF9 cells were infected with baculovirus and incubated at 27° C. for 3 days. Cell culture medium was cleared by centrifugation, filtered and concentrated about 10 times in SartoFlow Slice 200 (Sartorius—Hydrosart cutoff 10 kD). After adjustment of pH to 7.0 and another centrifugation step, the concentrated protein was purified using standard procedures on Ni-NTA Superflow columns (Qiagen) or HiTrap Chelating HP columns (GE Healthcare) charged with $Ni^{2+}$ ions. IL-17F containing fractions were pooled and desalted on PD-10 columns (GE Healthcare).

Human IL-17F and rat IL-17F from baculovirus-infected cells were essentially free of contaminants after one purification step, and appeared predominantly as disulfide-linked homodimers as demonstrated by non-reducing SDS-PAGE. The biological activity of the His-tagged, baculovirus-expressed human IL-17F was comparable to the activity of commercial cytokines (*E. Coli* expressed huIL-17F, Peprotech EC or R&D Systems)

Expression and Purification of Human IL-17F and Rat IL-17F from CHOK1SV Cells huIL-17F or rat IL-17F coding sequences preceded by the CD33 leader sequence (MPLLLLLPLLWAGALAMD; SEQ ID NO:101), plus a His tag, and an AviTag (Avidity, Denver Colo.) were placed under the control of the hCMV promoter in the expression vector pEE14.4. IL-17F was expressed from a bicistronic mRNA containing a viral internal ribosome entry site (IRES) and the GFP coding sequence as the second cistron. The pEE14.4.vector contains the glutamine synthetase (GS) gene, essential for the survival of transfected cells in selection medium containing methionine sulphoximine (MSX). Stable transfectants were generated in the CHOK1 SV cell line, property of Lonza Biologics. After four weeks of culture in the presence of MSX high-expressing clones were identified, expanded and used for the production of human or rat IL-17F.

CHOK1SV—expressed human IL-17F and rat IL-17F were purified by $Ni^{2+}$ affinity chromatography. They were essentially free of contaminants and appeared as disulfide-linked homodimers on non-reducing SDS-PAGE gels. The biological activity of the His+Avi-tagged, CHO-expressed human IL-17F was significantly decreased as compared to the activity of the commercial huIL-17F, probably due to the presence of a bulky, double tag at the N-terminus.

Expression and Purification of Human IL-17F cnIL-17F from PEAK Cells

His-tagged huIL-17F or cnIL-17F coding sequences were fused to the *Gaussia princeps* luciferase leader sequence (AF015993) and placed under the control of the EF1 promoter in the episomal expression vector pEAK8. The cytokine-coding sequence was followed by a viral internal ribosome entry site (IRES) and a second cistron (GFP). The pEAK8 vector contains the puromycin resistance gene, the EBV nuclear antigen 1 (EBNA1) and the oriP origin of replication. EBNA1 and oriP are necessary for the propagation of the pEAK8 vector as episomal DNA in human cells and the generation of stable transfectants. Stably transfected cells were obtained after 7-10 days of culture in the presence of 2 ug/mL of puromycine. The populations of puromycine resistant cells were expanded and used for cytokine production.

PEAK—expressed purified by $Ni^{2+}$ affinity chromatography were >95% pure and were found predominantly in the form of disulfide-linked homodimers, as demonstrated by non-reducing SDS-PAGE. The biological activity of the His-tagged, PEAK-expressed human IL-17F was similar to the activity of the huIL-17F from commercial sources.

Example 2

Immunizations

Fully human monoclonal antibodies were generated using transgenic strains of mice in which mouse antibody gene expression was suppressed and replaced with human antibody gene expression. Three strains of transgenic mice were used:
1) HuMab® mouse (Medarex, Princeton N.J.)
2) KM™ mouse, a crossbred between HuMAb Mouse and Kirin's TC Mouse (Kirin Pharma Company, Japan)
3) KM (FCγRIIb-KO) mouse, a strain derived from KM™ mouse, in which the gene Fcgr2b coding for the inhibitory Fc gamma Receptor IIB has been inactivated.

Mice were immunized either with human IL-17F or both human IL-17F and rat IL-17F. Two forms of antigen were used for immunizations: non-conjugated IL-17F or IL-17F conjugated to Keyhole Limpet Hemocyanin (KLH). Immunization strategies followed standard protocols from the literature.

Sera of immunized animals were screened periodically by ELISA for the presence of human IgG directed against huIL-17F and rat IL-17F. Most of the animals developed high-titer responses to human IL-17F. When both rat IL-17F and huIL-17 were used for immunizations, most of the animals developed high-titer responses to both antigens. Antibodies cross-reactive to huIL-17A were sporadically generated in KM and KM (FCγRIIb-KO) mice immunized with huIL-17F as the only antigen (i.e., without rat IL-17F). Contrary to the KM and KM (FCγRIIb-KO) mice, HuMAb mice did not develop cross-reactive titers to IL-17A, irrespective of the immunization protocol employed.

Example 3

Generation of Hybridomas

Fusion of Lymph Node Cells with SP2/0 Myeloma Cells

To obtain hybridomas, popliteal, inguinal, para-aortic, submandibular, cervical, axial, and brachial lymph nodes were removed from the mice and digested with collagenase and DNAse. Single cells suspension of lymph node cells was mixed at 1:1 ratio with SP2/0 myeloma cells and suspended in Cytofusion Low Conductivity Medium (CPS-LCMC, CytoPulse Sciences, Inc.). Fusions were done with 30 to 60 million splenocytes in the CytoPulse CEEF50 Electrofusion apparatus as indicated by the manufacturer (Cyto Pulse Sciences, Inc). After electrofusion, cells were incubated for approximately 1 hour at 37° C. to allow recovery before distributing into 96-well plates.

Culture of Hybridomas

Fused cells were resuspended in HAT selection medium and plated in 44 to 52 96-well plates at a cell concentration of $0.1-0.2 \times 10^5$ splenocytes per well in 200 μl medium. Hybridoma selection proceeded for 14 days. Fusion of lymph nodes of immunized mice resulted in the generation of hybridomas producing antibodies specific to huIL-17F or cross-reactive antibodies specific to both huIL-17F and IL-17A.

Hybridoma Screening

Fourteen days after the fusion, hybridoma-containing plates were screened for the presence of human IgG binding to human IL-17F and/or human IL-17A by FLISA (Fluorescence-Linked Immunosorbent Assay). In brief, 6 micron beads (Polybeads, cat. No 07312, Polysciences Inc.) were coated with huIL-17F (both from Peprotech EC) or BSA (Sigma) and were distributed into FMAT® 384-well optical plates (Applied Biosystems) at a density of 5,000 beads per well. The beads were mixed with a small volume of hybridoma culture supernatants (30 μl per well) and incubated overnight before addition of goat anti-human IgG Fc (Jackson Immunoresearch No 109-005-098) conjugated to FMAT Blue® dye (Applied Biosystems). After an incubation period of 2 to 8 hours the fluorescence of the beads was measured in an 8200 Cellular Detection System analyzer (Applied Biosystems). Hybridomas producing human IgGs that bound to huIL-17F, but not to BSA, were expanded and subjected to further analysis.

Example 4

Recombinant Antibody Generation

Antibody Sequence Cloning from Hybridoma

To isolate antibody variable heavy and light chain sequences, RNA was first extracted from selected hybridoma and subjected to reverse transcription. Then, VH and VL sequences were amplified by PCR, cloned and further analyzed by DNA sequencing. In brief, template RNA was extracted from hybridoma using RNeasy Plus kit (QIAGEN) and cDNA were generated using ready-to-go you-prime first-strand beads (GE Healthcare, No 27-9264-01) with oligo dT primers for the reverse transcription. VH and VL sequences were then amplified by PCR using primer sets recognizing families of human variable heavy and light chains. Amplified sequences were cloned into pCR®4 vector using TOPO® TA Cloning Kit for Sequencing (Invitrogen). Selected clones were then subject to DNA sequencing.

Antibody Reformatting, Germlining and Expression

Variable heavy and light chain sequences were reformatted into mammalian expression vectors for antibody production and characterization. In brief, sequence analysis was performed with isolated VH and VL to determine their germline. Due to primer mismatches, mutations were introduced in 5' of 1F1 and 11C5 VLs during the PCR amplification step. Therefore, site directed mutagenesis, conducted with the Quikchange kit (Strategene), was used to convert these mutations back to the Human germline sequence. Afterward, VH and VL sequences were sub-cloned into mammalian expression system in frame of Human IgG1 and IgKappa backbones. Antibody heavy and light chains corresponding vectors were then transfected in PEAK cells using TransIT®-LT1 transfection reagent (Mirus Bio) and cultured in DMEM+IgG-depleted serum+Glutamine. PEAK-expressed antibodies were then purified from the supernatant using MabSelectSure slurry (GE Healthcare).

Example 5

Cross-Reactivity of huIL-17F Antibodies

Binding assay: huIL-17F antibodies were tested for their ability to bind to the other members of the IL-17 family of cytokines, as well as to IL-17A and IL-17F from other species. The assay was performed in the FLISA format, as described above. The following recombinant cytokines were bound to polystyrene beads and tested for their ability to bind huIL-17F antibodies: huIL17B (PeprotechEC, cat No 200-28), huIL-17C (R&D Systems, cat No), huIL-17D (PeprotechEC, cat No 200-27), huIL-17E (huIL-25, PeprotechEC, cat No 200-24), muIL-17A (PeprotechEC, cat No 210-17), muIL-17F (PeprotechEC, cat No 200-17F), rat IL-17F (His-tagged, produced in house in insect cells), rat IL-17A (His-tagged, produced in house in PEAK cells), cyIL-17F (His-tagged, produced in house in PEAK cells), and cyIL-17A (His-tagged, produced in house in PEAK cells). The ability of the individual the huIL-17F antibodies to bind these different cytokines is summarized in Table 3 below:

TABLE 3

Cross-reactivity of huIL-17F antibodies as determined by FLISA (n.t. = not tested)

| | | | | species | | | | | | | | | | |
|---|---|---|---|---|---|---|---|---|---|---|---|---|---|---|
| | human | | | | | | | cynomolgus | | | mouse | | | rat |
| | | | | | | | dimer: | | | | | | | |
| clone name | IL-17F | IL-17A | IL-17A/F | IL-17B | IL-17C | IL-17D | IL-17E | IL-17F | IL-17A | IL-17A/F | IL-17F | IL-17A | IL-17A/F | IL-17F | IL-17A |
| 5E12 | + | − | − | − | − | − | − | + | − | − | − | − | − | − | − |
| 41B10 | + | − | + | − | − | − | − | + | − | + | − | − | − | − | − |
| 11C5 | + | − | + | − | − | − | − | + | − | + | − | − | − | − | − |
| 21B10 | + | − | + | − | − | − | − | + | − | + | − | − | − | − | − |
| 1F1 | + | − | + | − | − | − | − | + | − | + | − | − | − | − | − |
| 2E12 | + | − | + | − | − | − | − | + | − | + | − | − | − | − | − |
| 5D3 | + | − | + | − | − | − | − | + | − | + | − | − | − | − | − |
| 22F8 | + | − | + | − | − | − | − | + | − | + | − | − | − | − | − |
| 28B11 | + | − | + | − | − | − | − | + | − | + | − | − | − | − | − |
| 41A4 | + | − | + | − | − | − | − | + | − | +/− | − | − | − | − | − |
| 43G6 | + | − | + | − | − | − | − | + | − | + | − | − | − | − | − |

Example 6

Neutralization Potency of huIL-17F Antibodies

IL-6 Secretion by IL-17-stimulated Mouse Embryonic Fibroblasts

Human and cynomolgus IL-17A and IL-17F bind the corresponding mouse IL-17 receptor complex. As a consequence, mouse fibroblasts respond to human or cynomolgus IL-17A and IL-17F by secreting IL-6. Co-stimulation with mouse TNF was shown to synergize with IL-17 signaling (Ruddy et al. 2004, J. Biol. Chem. 279:2559) significantly increasing the sensitivity of the mouse fibroblasts to IL-17 cytokines. Mouse C57BL/6 embryonic fibroblasts (MEF, ATCC No SCRC-1008) were therefore used to assay for the neutralization capacity of huIL-17F antibodies to neutralize huIL-17F, cyIL-17F, huIL-17A/F heterodimer and cyIL-17A/F heterodimer biological activity.

Briefly, MEF cells seeded in 96-well plates in DMEM+ Glutamine+10% Fetal Bovine Serum (PBS) were cultured for 48 h before the addition of IL-17 cytokines and mouse TNFα at 10 ng/ml (Peprotech EC, cat No 315-01A). In assays for MAb neutralizing activity, the IL-17 cytokines were pre-incubated with the antibody for 1 hour before adding to the cells. After 24 hours of stimulation in the presence of human or cynomolgus IL-17A/F heterodimers (50 ng/ml) or after 40 hours of stimulation in the presence of human or cynomolgus IL-17F (5 ng/ml), supernatants were collected and the concentration of mouse IL-6 was measured by sandwich ELISA using rat anti mouse IL6 antibody (BD cat No 554400) for capture and a second, biotinylated, rat anti mouse IL6 antibody (BD 554402) plus streptavidin HRP (Jackson Immunoresearch 016-030-084) for detection. No inhibition of huIL-17A/F heterodimer or cyIL-17A/F heterodimer was observed with any of the anti IL-17F antibodies tested. The values of $IC_{50}$ obtained with human and cynomolgus IL-17F homodimers are summarized in Table 4 below and were obtained from IL-6 calibration curves using standard statistical techniques.

TABLE 4

Neutralization potency ($IC_{50}$ values) of huIL-17F antibodies in MEF cells stimulated with huIL-17F or cy IL-17F homodimers and mTNF-α

| species | human | cynomolgus |
|---|---|---|
| IL-17 dimer: | IL-17F | IL-17F |
| IL-17 conc. | 5 ng/ml | 5 ng/ml |
| clone name | IC50 (nM) | |
| 5E12 | 1.8 | 22 |
| 41B10 | 3.9 | 18 |
| 11C5 | 0.4 | 2.9 |
| 21B10 | 2.0 | 8.7 |
| 1F1 | 1.1 | 11 |
| 2E12 | 5.9 | 26 |
| 5D3 | 0.5 | 12 |
| 22F8 | 2.0 | 10 |
| 28B11 | 1.2 | 6.3 |
| 41A4 | 0.6 | 7.2 |
| 43G6 | 1.1 | 8.4 |

Example 7

Experimental Model of Disease: Collagen-induced Arthritis (CIA)

IL-17A plays an important role in the pathogenesis of arthritis, promoting the release of mediators of inflammation and cartilage destruction. The neutralization of IL-17A has been demonstrated to attenuate arthritis in various experimental models, including CIA (Collagen-Induced Arthritis). Given that IL-17F is closely related to IL-17A, and the fact that it is overexpressed in the synovia of rheumatoid arthritis (RA) patients, the effect of neutralizing this cytokine was explored in a model of RA. To this goal, an anti mIL-17F (mouse IL-17F) antibody that potently neutralized mouse IL-17F homodimers—but not IL-17A/F heterodimers—was generated, and the effects of this anti-mIL-17F antibody in the CIA animal model for RA were tested.

In brief, 8-10 week-old male DBA-1J mice were immunized with 100 micrograms bovine collagen type II in Complete Freund Adjuvant (CFA). Collagen type II in CFA was injected intradermally at the base of the tail. Three weeks later, 100 micrograms of collagen type II in Incomplete Freund Adjuvant (IFA) was injected intradermally to induce disease. The first signs of disease usually appeared 4 to 10 days after the collagen-IFA boost. Animals that started to develop arthritis were recruited to the study and distributed into the following treatment groups:

1) Isotype control (mouse IgG1k), two times per week for three weeks at 300 micrograms per injection (n=10)
2) Hamster murine chimeric anti TNF-alpha, once a week for three weeks at 300 micrograms per injection (n=10)
3) Anti mouse IL-17F antibody (mouse IgG1k) two times per week for three weeks at 300 micrograms per injection (n=11)

The three treatment groups were balanced to contain equivalent number of animals recruited at different clinical severity scores (1 to 3). Clinical scoring of the disease was performed three times per week using standard arthritis scoring methods. Scoring was 0-4 per paw (where 0 means no disease and 4 represents edema that involves the entire paw) with a theoretical maximum cumulative score of 16 scores per animal. In addition to clinical severity scoring, serum levels of key proinflammatory cytokines were determined by Luminex at termination (day 22 after recruitment).

Figure 2:
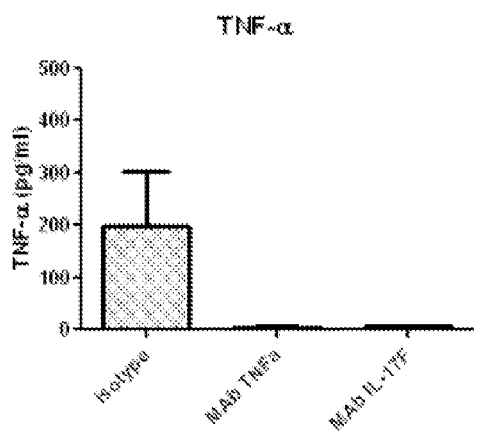
FIGS. 2A-2F are a series of graphs that depict various cytokine serum levels in mice immunized with bovine collagen type II as determined at termination (day 22).
Figure 2:
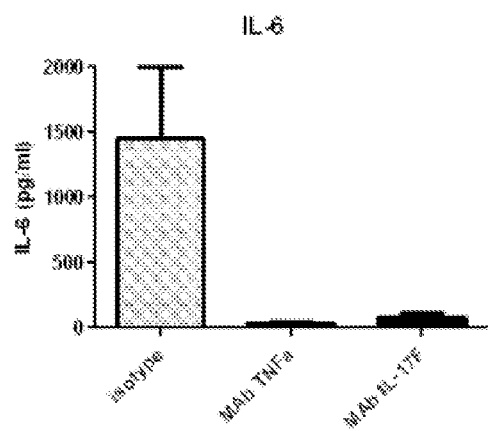
Figure 2:
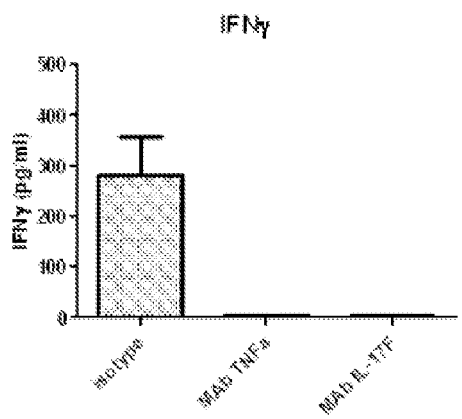
Figure 2:
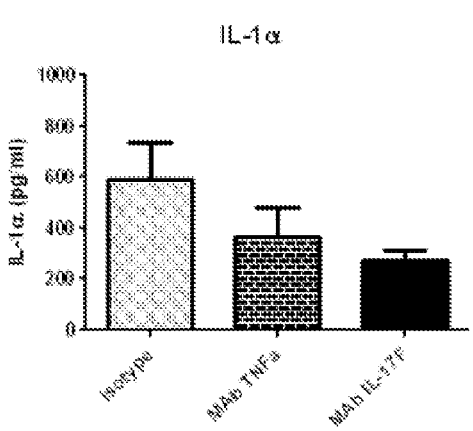
Figure 2:
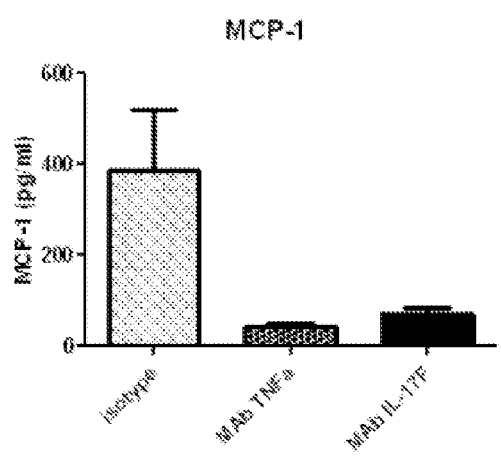
Figure 2:
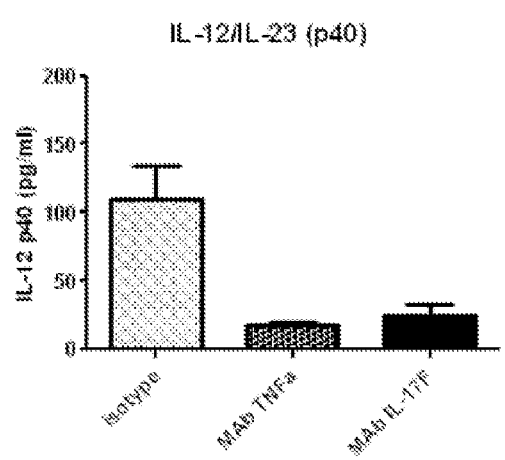

The progression of clinical scores and the cytokine serum levels are shown in FIGS. 1 and 2, respectively. The neutralization of IL-17F homodimers was sufficient to significantly delay the progression of the disease and reduced the levels of inflammatory mediators. These findings suggest that IL-17F is a candidate target for the therapy of autoimmune diseases such as rheumatoid arthritis.

The invention having now been described by way of written description and example, those of skill in the art will recognize that the invention can be practiced in a variety of embodiments and that the description and examples above are for purposes of illustration and not limitation of the following claims.

What is claimed is:

1. An isolated fully human monoclonal anti-IL-17F antibody, or fragment thereof, wherein said antibody comprises:
    (a) a VH CDR1 region comprising the amino acid sequence of SEQ ID NO:45,
    (b) a VH CDR2 region comprising the amino acid sequence of SEQ ID NO:46,
    (c) a VH CDR3 region comprising the amino acid sequence of SEQ ID NO:47,
    (d) a VL CDR1 region comprising the amino acid sequence of SEQ ID NO:74,
    (e) a VL CDR2 region comprising the amino acid sequence of SEQ ID NO:75, and
    (f) a VL CDR3 region comprising the amino acid sequence of SEQ ID NO:76, wherein said antibody binds IL-17F.

2. The antibody of claim 1, wherein said antibody does not bind the IL-17A homodimer.

3. The antibody of claim 1, wherein said antibody is an IgG isotype.

4. The antibody of claim 1, wherein said antibody is an IgG1 isotype.

5. The antibody of claim 1, wherein said antibody comprises a heavy chain variable region comprising the amino acid sequence of SEQ ID NO:10, and a light chain variable region comprising the amino acid sequence of SEQ ID NO:12 or 103.

6. A pharmaceutical composition comprising the antibody of claim 1 and a carrier.

* * * * *

UNITED STATES PATENT AND TRADEMARK OFFICE
CERTIFICATE OF CORRECTION

PATENT NO. : 8,137,671 B2
APPLICATION NO. : 12/774188
DATED : March 20, 2012
INVENTOR(S) : Masternak et al.

Page 1 of 1

It is certified that error appears in the above-identified patent and that said Letters Patent is hereby corrected as shown below:

On the title page item (73)

Please delete "Genentech, Inc,. South San Francisco, CA (US)" and substitute

-- Novimmune, SA (Geneva, CH) --.

Signed and Sealed this
Eighth Day of July, 2014

Michelle K. Lee
*Deputy Director of the United States Patent and Trademark Office*